United States Patent [19]
Fernandez et al.

[11] Patent Number: 5,916,920
[45] Date of Patent: *Jun. 29, 1999

[54] 3-SUBSTITUTED BICYCLO[3.1.0]HEXANE-6-CARBOXYLIC ACIDS

[75] Inventors: Carmen Dominguez Fernandez, Madrid, Spain; David Reed Helton, Greenfield, Ind.; Steven Marc Massey; James Allen Monn, both of Indianapolis, Ind.

[73] Assignee: Eli Lilly and Company, Indianapolis, Ind.

[*] Notice: This patent is subject to a terminal disclaimer.

[21] Appl. No.: 08/749,301

[22] Filed: Nov. 14, 1996

Related U.S. Application Data

[60] Provisional application No. 60/006,871, Nov. 16, 1995.

[51] Int. Cl.$^6$ .......................... A61K 31/19; A61K 31/21; C07C 61/13; C07C 69/74
[52] U.S. Cl. .......................... 514/561; 560/119; 562/501; 514/510
[58] Field of Search ............................. 560/119; 562/501; 514/510, 561

[56] References Cited

U.S. PATENT DOCUMENTS

| | | | |
|---|---|---|---|
| 3,981,880 | 9/1976 | Schneider | 260/468 |
| 4,976,891 | 12/1990 | Narisada et al. | 260/401 |
| 5,750,566 | 5/1998 | Monn et al. | 514/510 |

FOREIGN PATENT DOCUMENTS

| | | |
|---|---|---|
| 696 577 | 2/1996 | European Pat. Off. . |
| WO 95/15940 | 6/1995 | WIPO . |
| WO 96/04900 | 2/1996 | WIPO . |
| WO 96/04901 | 2/1996 | WIPO . |
| WO 96/05175 | 2/1996 | WIPO . |
| WO 96/07405 | 3/1996 | WIPO . |

OTHER PUBLICATIONS

D. Schoepp, et al., "Selective Inhibition of Forskolin–stimulated Cyclic AMP Formation in Rat Hippocampus by a Novel mGlur Agonist, 2R,4R–4–aminopyrrolidine–2,4–dicarboxylate", *Neuropharmacology*, 34(8), 843–850 (1995).

D. Schoepp, et al., "Pharmacological and fuctional characteristics of metabotropic excitatory amino acid receptors", *TiPS*, 11(12), 508–515 (1990).

D. Schoepp, et al., "Metabotropic glutamate receptors in brain function and pathology", *TiPS*, 14, 13–20 (1993).

*Primary Examiner*—Laura L. Stockton
*Attorney, Agent, or Firm*—Martin A. Hay

[57] ABSTRACT

Compounds of the formula

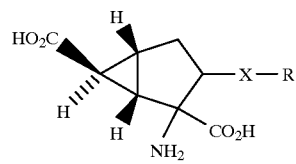

in which X represents a bond, S, O or $NR^a$; and R is as defined in the specification are useful as modulators of metabotropic glutamate receptor function.

13 Claims, No Drawings

3-SUBSTITUTED BICYCLO[3.1.0]HEXANE-6-CARBOXYLIC ACIDS

This application claims the benefit of U.S. Provisional Application No. 60/006,871, filed Nov. 16, 1995.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

The present invention provides a compound of formula

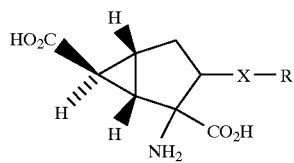

I in which X represents a bond, S, O or NRa; R represents a (1–6C) alkyl group; a (2–6C)alkenyl group; a (2–6C)alkynyl group or an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C)alkenyl or (2–6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_nR^b$; n is 0 or 1; and $R^b$ is as described for R; or a non-toxic metabolically labile ester or amide thereof; or a pharmaceutically acceptable salt thereof.

It will be appreciated that the compounds of formula I contain at least four asymmetric carbon atoms; three being in the cyclopropane ring and two being in the cyclopentane ring. The present invention includes all stereoisomeric forms of the compounds of formula I, including each of the individual enantiomers and mixtures thereof.

Preferably the compounds of formula I have the configuration shown below

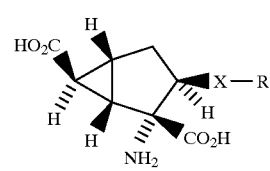

Ia

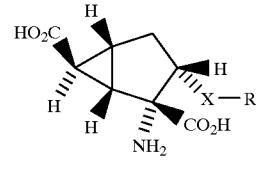

Ib

The configuration of formula Ib is most preferred.

As used herein, the term "alkyl" means a straight chain or branched group. Examples of values for a (1–6C) alkyl group include (1–4C) alkyl such as methyl, ethyl, propyl, isopropyl, butyl and isobutyl.

The term (2–6C) alkenyl includes (2–4C) alkenyl such as allyl.

The term (2–6C) alkynyl includes (2–4C) alkynyl such as propynyl.

The term heteroaromatic group includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl.

The term aromatic group includes phenyl and a polycyclic aromatic carbocyclic ring such as naphthyl.

The term "optionally substituted", as used in the term "optionally substituted heteroaromatic or aromatic group", herein signifies that one or more (for example one, two or three) substituents may be present, said substituents being selected from atoms and groups which, when present in the compound of formula I, do not prevent the compound of formula I from functioning as a modulator of metabotropic glutamate receptor function.

Examples of atoms and groups which may be present in an optionally substituted heteroaromatic or aromatic group are amino, hydroxy, nitro, halogeno, (1–6C) alkyl, (1–6C) alkoxy, (1–6C)alkylthio, carboxy, (1–6C) alkoxycarbonyl, carbamoyl, (1–6C) alkanoylamino, (1–6C)alkylsulphonyl, (1–6C) alkylsulphonylamino, optionally substituted phenyl, optionally substituted phenoxy, phenylthio, phenylsulphonyl, phenylsulphonylamino, toluenesulphonylamino, (1–6C)fluoroalkyl and (1–6C) fluoroalkoxy. Examples of particular values are amino, hydroxy, fluoro, chloro, bromo, iodo, methyl, methoxy, methylthio, carboxy, acetylamino, methanesulphonyl, nitro, acetyl, phenoxy, 3-trifluoromethylphenoxy, 4-chlorophenoxy, phenylthio, phenylsulphonyl, methanesulphonylamino, trifluoromethyl, trifluoromethoxy, and tetrafluoroethoxy.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,3-difluorophenyl, 2,4-difluorophenyl, 2,5-difluorophenyl, 3,4-difluorophenyl, 3,5-difluorophenyl, 2,3,4-trifluorophenyl, pentafluorophenyl, 2-chlorophenyl, 3-chlorophenyl, 4-chlorophenyl, 2,3-dichlorophenyl, 2,4-dichlorophenyl, 3,4-dichlorophenyl, 3,5-dichlorophenyl, 3-chloro-4-fluorophenyl, 2-bromophenyl, 3-bromophenyl, 4-bromophenyl, 2-methylphenyl, 3-methylphenyl, 4-methylphenyl, 3,5-dimethylphenyl, 4-fluoro-3-methylphenyl, 3-fluoro-2-methylphenyl, 2-methoxyphenyl, 3-methoxyphenyl, 4-methoxyphenyl, 3,5-dimethylphenyl, 2,3-dimethoxyphenyl, 2,5-dimethoxyphenyl, 3,4-dimethoxyphenyl, 3,5-dimethoxyphenyl, 3-fluoro-4-methoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-chloro-5-trifluoromethylphenyl, 2-fluoro-5-trifluoromethylphenyl, 3-trifluoromethoxyphenyl, 3-tetrafluoroethoxyphenyl, 2-phenoxyphenyl, 3-phenoxyphenyl, 3-carboxyphenyl, and 4-carboxyphenyl.

The term "non-aromatic carbocyclic group" includes a monocyclic group, for example a (3–10C)cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3.3.1]non-1-yl,-2-yl,-3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3–10C)cycloalkyl group fused with a benzene ring or a an aromatic 5–6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5, 6,7-tetrahydrobenzothiophen-4-yl, - 5-yl, -6-yl or -7-yl, dibenzo[2,3,6,7]cycloheptan-1-yl or - 4-yl, dibenzo[2,3,6,7] cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5–6 membered ring containing from one to four heteroatoms selected from oxygen, sulfur and nitrogen, such as 2,3-dihydrobenzopyran-2-yl, -3-yl or -4-yl, xanthen-9-yl, 1,2,3, 4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

Examples of values for R when it represents a (1–6C) alkyl group are methyl, ethyl and propyl.

An example of a value for R when it represents a (2–6C) alkenyl group is allyl.

An example of a value for R when it represents a (2–6C) alkynyl group is a propynyl.

An example of a value for R when it represents an optionally substituted heteroaromatic group is 2-pyrimidyl.

When R represents an optionally substituted aromatic group, it preferably represents a 2-naphthyl group or a phenyl group which is unsubstituted or substituted by one or two substituents selected independently from halogen, (1–4C) alkyl, (1–4C) alkoxy and phenyl.

Examples of values for R when it represents an optionally substituted aromatic group are 2-naphthyl, phenyl, 2-fluorophenyl, 3-fluorophenyl, 4-fluorophenyl, 3,4-difluorophenyl, pentafluorophenyl, 2-chlorophenyl, 3-chlorophenyl, 4-chlorophenyl, 3,4-dichlorophenyl, 2,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 3-trifluoromethylphenyl and 4-trifluoromethylphenyl.

Examples of values for R when it represents a substituted (1–6C) alkyl, (2–6C)alkenyl or (2–6C)alkynyl group are phenyl (1–4C) alkyl and diphenyl (1–4C) alkyl, especially benzyl and diphenylmethyl groups, which are unsubstituted or substituted on phenyl by one, two or three substituents selected independently from halogen, (1–4C) alkyl, (1–4C) alkoxy, (1–4C)fluoroalkyl, (1–4C)fluoroalkoxy, phenyl, phenoxy, 3-trifluoromethylphenoxy and 4-chlorophenoxy.

R preferably represents a phenyl(1–4C)alkyl or diphenyl (1–4C) alkyl group, especially a benzyl or diphenylmethyl group, in which any phenyl ring is unsubstituted or substituted by one, two or three substituents selected independently from fluoro, chloro, methyl, isopropyl, methoxy, trifluoromethyl, trifluoromethoxy, tetrafluoroethoxy, phenyl, phenoxy, 3-trifluoromethylphenoxy and 4-chlorophenoxy.

Particular values for R are methyl, phenylpropyl, benzyl, 2-fluorobenzyl, 3-fluorobenzyl, 4-fluorobenzyl, 2,3-difluorobenzyl, 2,4-difluorobenzyl, 2,5-difluorobenzyl, 3,5-difluorobenzyl, 3,4-difluorobenzyl, 2,3,4-trifluorobenzyl, 2-chlorobenzyl, 3-chlorobenzyl, 4-chlorobenzyl, 2,3-dichlorobenzyl, 2-chloro-5-trifluoromethylbenzyl, 3-chloro-4-fluorobenzyl, 2-methylbenzyl, 3-methylbenzyl, 4-methylbenzyl, 4-fluoro-3-methylbenzyl, 3-fluoro-2-methylbenzyl, 3,5-dimethylbenzyl, 4-isopropylbenzyl, 2,4-dimethylbenzyl, 2,5-dimethylbenzyl, 2-methoxybenzyl, 3-methoxybenzyl, 4-methoxybenzyl, 3-fluoro-4-methoxybenzyl, 3-methyl-4-methoxybenzyl, 4-trifluoromethylbenzyl, 3-fluoro-5-trifluoromethylbenzyl, 3-trifluoromethoxybenzyl, 3-tetrafluoroethoxybenzyl, 4-phenylbenzyl, 3-phenoxybenzyl, 3-(3-trifluoromethylphenoxy)benzyl, 3-(4-chloro-phenoxy)benzyl, and diphenylmethyl.

A preferred value for $R^a$ is hydrogen.

X preferably represents a bond.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylammonium, sodium, methylammonium, calcium, and the like salts.

Pharmaceutically acceptable metabolically labile ester and amide of compounds of formula I are ester or amide derivatives of compounds of formula I that are hydrolyzed in vivo to afford said compound of formula I and a pharmaceutically acceptable alcohol or amine. Examples of metabolically labile esters include esters formed with (1–6C) alkanols in which the alkanol moiety may be optionally substituted by a (1–8C) alkoxy group, for example methanol, ethanol, propanol and methoxyethanol. Example of metabolically labile amides include amides formed with amines such as methylamine.

According to another aspect, the present invention provides a process for the preparation of a compound of formula I which comprises (a) hydrolyzing a compound of formula

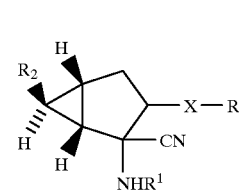

II in which $R^1$ represents a hydrogen atom or an acyl group and $R^2$ represents a carboxyl group or an esterified carboxyl group, or a salt thereof;

(b) hydrolyzing a compound of formula

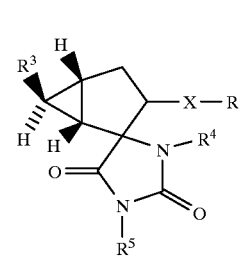

III in which $R^3$ represents a carboxyl group or an esterified carboxyl group, and $R^4$ and $R^5$ each independently represent a hydrogen atom, a (2–6C) alkanoyl group, a (1–4C) alkyl group, a (3–4C) alkenyl group or a phenyl (1–4C) alkyl group in which the phenyl is unsubstituted or substituted by halogen, (1–4C) alkyl or (1–4C) alkoxy, or a salt thereof; or (c) deprotecting a compound of formula

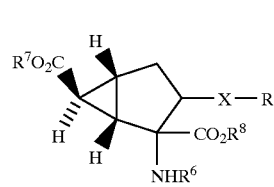

IV in which $R^6$ represents a hydrogen atom or a nitrogen protecting group and each of $R^7$ and $R^8$ independently represent a hydrogen atom or a carboxyl protecting group, or a salt thereof;

whereafter, if necessary and/or desired (i) resolving the compound of formula I;

(ii) converting the compound of formula I into a non-toxic metabolically labile ester or amide thereof; and/or;

(iii) converting the compound of formula I or a non-toxic metabolically labile ester or amide thereof into a pharmaceutically acceptable salt thereof.

The protection of carboxylic acid and amine groups is generally described in McOmie, Protecting Groups in Organic Chemistry, Plenum Press, N.Y., 1973, and Greene and Wuts, Protecting Groups in Organic Synthesis, 2nd. Ed., John Wiley & Sons, N.Y., 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula $R^{11}CO$ in which $R^{11}$ represents (1–6C) alkyl, (3–10C) cycloalkyl, phenyl(1–6C) alkyl, phenyl, (1–6C) alkoxy, phenyl(1–6C)alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonylamino, and (1–6C) fluoroalkyl.

The compounds of formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range of from 50 to 200° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50 to 150° C.

Preferred values for $R^1$ are hydrogen and (2–6C)alkanoyl groups, such as acetyl.

Preferred values for $R^2$ when it represents an esterified carboxyl group are (1–6C)alkoxycarbonyl groups such as ethoxycarbonyl.

The compounds of formula IV may be deprotected by a conventional method. Thus, an alkyl carboxyl protecting group may be removed by hydrolysis. The hydrolysis may conveniently be performed by heating the compound of formula IV in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from 10 to 300° C. An aralkyl carboxyl protecting group may conveniently be removed by hydrogenation. The hydrogenation may conveniently be effected by reacting the compound of formula IV with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0 to 100° C. An acyl, amine protecting group is also conveniently removed by hydrolysis, for example as described for the removal of an alkyl carboxyl protecting group.

The compounds of formula II may be prepared by reacting a compound of formula V

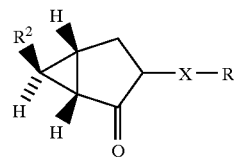

with an alkali metal cyanide, such as lithium, sodium or potassium cyanide, and an ammonium halide, such as ammonium chloride. It has been found advantageous to perform the reaction in the presence of ultrasound. Thus, the ammonium halide is advantageously mixed with chromatography grade alumina in the presence of a suitable diluent such as acetonitrile. The mixture is then irradiated with ultrasound, whereafter the compound of formula V is added, and the mixture is again irradiated. The alkali metal cyanide is then added, followed by further irradiation with ultrasound.

The resultant mixture of diastereoisomeric aminonitriles may then be reacted with an acylating agent, such as acetyl chloride in the presence of a suitable base, for example an amine such as ethyl diisopropylamine and in the presence of a suitable solvent such as dichloromethane, to afford a mixture of diastereomeric acylamino nitriles. The desired diastereoisomer may conveniently be separated from this mixture, for example by chromatography.

The compounds of formula III may be prepared by reacting a compound of formula V with an alkali metal cyanide, such as lithium, sodium or potassium cyanide, and ammonium carbonate in an aqueous alcohol, such as aqueous ethanol. Conveniently the reaction is performed at a temperature in the range of from 35 to 150° C. If desired, the compounds of formula III may then be alkylated, for example using an appropriate compound of formula $R^4Cl$ and/or $R^5Cl$.

The compounds of formula V in which X represents a bond and R represents a (1–6C) alkyl or substituted (1–6c) alkyl group may be prepared by hydrogenating a compound of formula

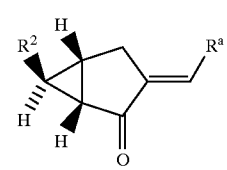

in which $R^a$—= represents a group hydrogenatable to a group R. For example, when RX represents an unsubstituted or substituted benzyl group, $R^a$ represents an unsubstituted or substituted phenyl group. Alternatively, compounds of formula VI may be reached with a suitable organometallic reagent such as an organozinc reagent, for example phenyl zinc bromide, to afford a compound of formula V.

The resultant compound of formula V may be epimerised, for example, by treatment with a strong base such as sodium ethoxide in ethanol.

The hydrogenation is conveniently performed in the presence of a group VIII metal catalyst, such as Raney-nickel. Suitable solvents include esters such as ethyl acetate. The temperature is conveniently in the range of from 0 to 100° C.

The compounds of formula VI may be prepared by dehydrating a compound of formula VII

VII

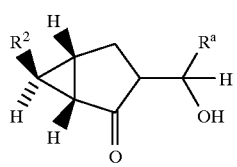

The dehydration is conveniently performed in the presence of a dehydrating agent, for example, a sulfonyl chloride such as p-toluenesulfonyl chloride or methanesulfonyl chloride.

Alternatively, the compounds of formula V may be prepared by hydrogenating a compound of formula VII in the presence of a palladium catalyst, for example, palladium on carbon.

The compounds of formula VII may be prepared by reacting a compound of formula

VIII

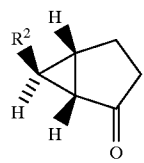

with a strong base (for example lithium bis(trimethylsilyl) amide to afford an enolate salt. The enolate salt is then reacted with an aldehyde of formula R$^a$CHO in the presence of a Lewis acid, such as BF$_3$ etherate. Suitable solvents for the reaction include ethers, such as tetrahydrofuran.

Alternatively, the compounds of formula VI may be prepared by reacting a compound of formula VIII with an aldehyde of formula R$^a$CHO in the presence of pyrrolidine. Suitable solvents for the reaction include alchols, such as ethanol. The reaction is conveniently performed at a temperature in the range of from 0 to 100° C.

The compounds of formula VI may also be prepared by reacting a compound of formula VIII with an aldehyde of formula R$^a$CHO in the presence of a base such as sodium hydroxide and in an aqueous reaction medium such as water. Under the conditions of this reaction, a protecting group R$^2$ may be removed by hydrolysis. This may be reintroduced, For example, an ethyl protecting group may be reintroduced by reacting the compound of formula VI with ethyl chloroformate in the presence of a base, such as triethylamine.

The compounds of formula VIII are known and may be prepared by reacting cyclopenten-1-one with a carboxy protected (dimethyl sulfuranylidene) acetate. Suitable solvents for the reaction include aromatic hydrocarbons, such as toluene. The desired diastereomeric product may be isolated by chromatography. The preparation of 1S, 5R, 6S-2-oxabicyclo[3.1.0]hexane-6-carboxylic acid is described in Example 19 of European Patent Application Publication No. EP-A1-0696577.

Compounds of formula V in which X represents a bond may also be prepared by alkylating an enol salt of a compound of formula VIII. Suitable alkylating agents include compounds of formula RZ in which Z represents a leaving atom or group, for example, a halogen atom such as bromine. Thus a compound of formula VIII is conveniently converted into an enol salt by reaction with a strong base, such as lithium (trimethylsilyl) amide, then it is reacted with the alkylating agent. Suitable solvents for the reaction include ethers such as diethyl ether and tetrahydrofuran.

Alternatively, compounds of formula V may be prepared by reacting a compound of formula

IX

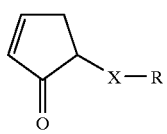

with a carboxy protected (dimethyl sulfuranylidene) acetate. Suitable solvents for the reaction include aromatic hydrocarbons, such as toluene.

The compounds of formula V in which X represents NH may be prepared by alkylating a compound of formula

X

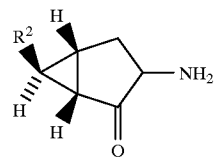

The alkylation may be effected using a conventional method, for example by reacting the compound of formula X with a compound of formula RZ in which Z represents a leaving atom or group such as a halogen atom, in the presence of a base.

The compounds of formula X may be prepared by several methods from a compound of formula VIII.

According to one method, a compound of formula VIII is reacted with a compound of formula RONO in the presence of a base, such as an alkali metal alkoxide, to afford an oxime. The reaction is generally conducted according to the method described in Williams, J. R. et al., J. Org. Chem., 1982, 47, 2536 and Wheeler, T. N. and Meinwald., J. Org. Synth. VI, 1988, 840. The oxime is then reduced, for example by hydrogenation in the presence of a palladium catalyst or using zinc in acetic acid. The procedures for the reductions generally follow the respective methods described in J. Med. Chem., 1984, 27, 20 and Fischer, H. Org. Synth III, 1955, 513.

According to another method, a compound of formula VIII is reacted with an arylsulfonylazide in the presence of a base, such as lithium diisopropylamide or lithium bis (trimethylsilyl)amide to afford an azide. The reaction is generally performed according to the method described in Evans, D. A.; et al.; J. Am. Chem. Soc., 1990, 112, 4011–4030. The azide is then reduced, for example by hydrogenation in the presence of palladium on carbon, or using stannous chloride. The reduction is generally performed according to the method described by Evans, et. al. (above).

According to yet another method, a compound of formula VIII is reacted with a compound of formula C(NO$_2$)$_4$ in the presence of a base, such as lithium diisopropylamide or lithium bis(trimethylsilyl)amide to afford a nitro compound. The reaction is generally performed according to the method described in Rathore, R.; et al., Tetrahedron Lett., 1993, 49, 1859–1862. The nitro compound is then reduced, for example using ammonium formate in the presence of a palladium catalyst. The reduction is generally performed according to the method demonstrated in Ram, S. et. al.; Tetrahedron Lett.; 1984, 25, 3415–3418.

The compounds of formula V in which X represents S may be prepared by reacting a compound of formula VIII with a compound of formula R-S-S-R in the presence of a base. The reaction is generally performed according to the method described in Trost, B. M. et. al., J. Am. Chem. Soc., 1975, 97, 438–440.

The compounds of formula V in which X represents O may be prepared by alkylating a compound of formula

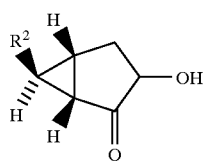

XI

The alkylation may be effected using a conventional method. For example, the compound of formula XI may be reacted with a compound of formula R-Z, in which Z represents a leaving atom or group, such as a halogen atom in the presence of a base. Alternatively, compounds of formula V in which R represents an aromatic group may be prepared by reacting the corresponding phenol of formula ROH with the compound of formula XI according to the method of the well known Mitsunobu reaction. Thus a phenol of formula ROH is reacted with a compound of formula XI in the presence of a triarylphosphine and diethyl azodicarboxylate.

The compounds of formula XI may be prepared by reacting a compound of formula VIII with dimethyldioxirane in the presence of a base. The reaction is generally performed according to the method described in Guertin, K. R., et. al.; Tetrahedron Lett.; 1991, 32, 715.

Many of the intermediates described herein, for example the compounds of formula II, III and IV, are believed to be novel and are provided as further aspects of the invention.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

Experiments were performed to demonstrate the ability of the formula I compounds to affect the excitatory amino acid receptors. The affinity for metabotropic glutamate receptors was demonstrated by the selective displacement of 1S,3R-ACPD-sensitive [$^3$H]glutamate binding to rat brain cell membranes. The binding of [$^3$H]glutamate was conducted with crude membranes of rat forebrain as described by Schoepp and True. Schoepp and True, *Neuroscience Lett.,* 145, 100–104 (1992) and Wright et al., J. Neurochemisty 63: 938–945 (1994). The products of the Examples herein have been found to give an $IC_{50}$ of less than 10 μM in this test. For example, the product of Example 1 was found to have an $IC_{50}$ of 0.32 μM.

Based on studies of receptor mediated changes in intracellar second messengers, metabotropic glutamate receptor are either coupled to enhanced phosphoinositide hydrolysis or decreases in forskolin-stimulated cAMP formation. Compounds may also be tested for ability to prevent inhibition of forskolin (30 μM)-stimulated cAMP formation by an mGluR agonist (1S,3R-ACPD, 20 μM) using slices of the rat hippocampus as described by D. D. Schoepp and B. G. Johnson, *Neurochemistry International* 22: 277–283 (1993) and human mGluR2 expressing non-neuronal cells (D. D. Schoepp et al., *Neuropharmacology,* 34: 843–850, 1995).

The product of Example 4 herein has been tested and found to exhibit as anxiolytic effect in the mouse elevated plus maze model (Lister, Psychopharmacology, 92:180–185; 1987).

The product of Example 25 herein has been tested and found to exhibit neuroleptic properties in the mouse conditioned active avoidance response model. (Pfeiffer & Jenney, Ann. N.Y. Acad. Sci., 66:293–246, 1957; Maffii, J. Pharm. Pharmacol., 11: 129–139, 1959; Cook & Weidley, Ann; N.Y. Acad. Sci., 66: 790–752, 1957; Janke, Handbook of Experimental Pharmacology, Vol. 55/I, New York: Plenum Press, 1978).

According to another aspect, the present invention provides a method of modulating one or more metabotropic glutamate receptor function in a warm blooded mammal, which comprises administering an effecting amount of a compound of formula I or a non-toxic metabolically labile ester or amide thereof, or a pharmaceutically acceptable salt thereof.

The compounds of the present invention are preferably formulated prior to administration. Therefore, another aspect of the present invention is a pharmaceutical formulation comprising a compound of formula I and a pharmaceutically-acceptable carrier, diluent, or excipient.

The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 | 70.00 |
| (Chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| Active Ingredient | 100 mg |
| Mannitol | 100 mg |
| 5 N Sodium hydroxide | 200 ml |
| Purified water to total | 5 ml |

The following Examples illustrate the invention.

The following abbreviations are used in the following: EtOAc, ethyl acetate; THF, tetrahydrofuran; EtOH, ethanol; IPA, isopropyl alcohol; DBU, 1,8-diazabicyclo[5.4.0]undec-7-ene; Et$_2$O, diethyl ether; DMAP, 4-dimethylaminopyridine; TsOH, p-toluenesulfonic acid; GC, Gas Chromatography; nOe, Nuclear Overhauser effect; TLC, thin layer chromatography; HPLC, high pressure liquid chromatography; m-CPBA, m-chloroperbenzoic acid; FDMS, Field Desorption Mass Spectrometry.

PREPARATION 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88–90° C.

PREPARATION 2

(1SR,5RS,6SR) Ethyl 2-Oxobicyclo[3.1.0]hexane-6-carboxylate

A suspension of carboethoxymethyl dimethylsulfonium bromide (45.5 g) in toluene (350 mL) was treated with 1,8-diazabicyclo[5.4.0]undec-7-ene (30.2 g). The resulting mixture was stirred at room temperature. After one hour, the reaction mixture was treated with 2-cyclopenten-1-one (19.57 g). After an additional 18 hours, the reaction mixture was added to a 1 N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g of the title compound. Melting point: 36–38° C.

FDMS: m/z=168 (M+).

Analysis calculated for $C_9H_{12}O_3$: C, 64.27; H, 7.19. Found: C, 64.54; H, 7.11.

EXAMPLE 1

Mixture of 1SR,2SR,3RS,5RS,6SR-2-amino-3-(3-phenylpropyl)bicyclo[3.1.0]-hexane-2,6-dicarboxylic acid and 1SR, 2RS, 3RS, 5RS, 6SR-2-amino-3-(3-phenylpropyl)bicyclo[3.1.0]hexane-2,6-dicarboxylic acid (a) 1SR,5RS,6SR-ethyl-2-oxo-3-(3-phenyl-1-hydroxypropyl)bicyclo[3.1.0]hexane-6-carboxylate. To a solution of the product of Preparation 2 (2.0 g, 11.9 mmol) in anhydrous THF (200 mL) under N$_2$ at −78° C. was added lithium bis(trimethylsilyl)amide (1 M in THF, 13.1 mL, 13.1 mmol). To this solution was added via cannula a pre-mixed solution of hydrocinnamaldehyde (2.0 g, 14.3 mmol) and BF$_3$.Et$_2$O (2.0 g, 14 mmol) in anhydrous THF (100 mL). After 3 h, the reaction mixture was quenched with saturated NH$_4$Cl. The reaction mixture was partitioned between Et$_2$O and H$_2$O, the organic phase was separated, dried (MgSO$_4$) and concentrated under reduced pressure. The product was purified by chromatography (10% EtOAc/hexane) yielding 2.9 g (79%) of the title compound: FDMS: M$^+$=302.

(b) 1SR,5RS,6SR-Ethyl-2-oxo-3-((3-phenyl)propen-1-yl)bicyclo[3.1.0]hexane-6-carboxylate. To a cooled solution of the product of step (a) (1.9 g, 6.3 mmol) in CH$_2$Cl$_2$ (15 mL) under N$_2$ was added DBU (1.9 g, 12.6 mmol) and methanesulfonyl chloride (0.9 g, 6.3 mmol). The reaction was allowed to proceed at ambient temperature for 16 h, then additional DBU (1.9 g, 12.6 mmol) was added, and the reaction was warmed under reflux for 4 h. The reaction mixture was washed with 1 N HCl, the organic phase was dried (MgSO$_4$) and concentrated under reduced pressure. The crude product was purified by HPLC (20%EtOAc/hexane) to afford 1.2 g (66%) of the title compound. FDMS: M$^+$=284; Anal. calcd. for $C_{18}H_{20}O_3$: C, 76.05; H, 7.09. Found: C, 75.74; H, 7.08.

(c) 1SR,3SR,5RS,6SR-Ethyl-2-oxo-3-(3-phenylpropyl) bicylo [3.1.0]hexane-6-carboxylate. The product of step (b) (0.97 g, 3.4 mmol) and Raney Ni (0.25 g) were combined in EtOAc and subjected to H$_2$ (60 psi) from 5 to 30 minutes. The catalyst was filtered and the filtrate was concentrated under reduced pressure to afford 0.95 g (97%) of the title compound. FDMS: M$^+$=286. Anal. calcd. for $C_{18}H_{22}O_3$.0.25 H$_2$O: C, 74.33; H, 7.80. Found: C, 74.33; H, 7.73.

(d) To a solution of the product of step (c) (0.8 g, 2.8 mmol) in EtOH (40 mL) was added a solution of (NH$_4$)$_2$CO$_3$ (0.95 g, 12.2 mmol) and KCN (0.26 g, 4.0 mmol) in H$_2$O (40 mL). The reaction mixture was stirred at 60° C. for 96 h, then cooled to ambient temperature and partially concentrated. The hydantoin intermediate was collected by filtration, then reconstituted in acetonitrile (25 mL) and treated with DMAP (0.054 g, 0.4 mmol) and a solution of di-tert-butyldicarbonate (1.6 g, 7.6 mmol) in CH$_3$CN (5 mL). The reaction mixture was stirred overnight, then partitioned between aqeous NaHSO$_4$ and Et$_2$O. The isolated organic phase was dried (MgSO$_4$) and concentrated to collect 1.0 g of bis-di-tert-butyl carbamate protected hydantoin. This product was combined with 2N sodium hydroxide (5 mL) and stirred for 24 h. Aqueous HCl (6 N, 6 mL) was added, and the mixture was stirred for an additional 72 h. The reaction mixture was concentrated, and subsequently reconstituted in 20 mL of EtOH/H$_2$O (1:1) mixture. The pH was adjusted to 3, and the solution was cooled to 0° C. The solids were filtered and washed with H$_2$O and acetone to collect 0.212 g of the title compound. An additional 0.064 g of the title compound was obtained by cation exchange chromatography of the filtrate (Dowex 50WX8-100 cation exchange resin). In total, 0.276 g (33%) of the title compound was obtained. mp=248–249° C.; FDMS: M$^+$=303; Anal. calcd. for C$_{17}$H$_{21}$NO$_4$: C, 67.30; H, 6.99; N, 4.62. Found: C, 67.09; H, 6.78; N, 4.66.

EXAMPLE 2

1SR,2SR,3SR,5RS,6SR-2-amino-3-((2,5-dimethyl) benzyl)bicyclo-[3.1.0]hexane-2,6-dicarboxylic acid a) 1SR,3SR,5RS,6SR-Ethyl-2-oxo-3-((2,5-dimethyl) phenylhydroxymethyl)bicyclo[3.1.0]hexane-6-carboxylate. The title compound was prepared by the methods of Examples 1(a) and 1(b) employing the product of Preparation 2 (5.0 g, 29.8 mmol) and 2,5-dimethylbenzaldehyde (4.8 g, 35.8 mmol). The title compound (4.7 g, 52%) was obtained after HPLC purification (5% EtOAc/hexane to 50% EtOAc/hexane). FDMS: M$^+$=302. Anal. calcd. for C$_{18}$H$_{22}$O$_4$: C, 70.66; H, 7.38. Found: C, 70.53; H, 7.38.

(b) 1SR,3SR,5RS,6SR-Ethyl-2-oxo-3-((2,5-dimethyl) benzyl) bicyclo[3.1.0]hexane-6-carboxylate. The title compound was prepared by hydrogenolysis of the produce of step (a) (4.1 g, 13.6 mmol) employing 5% Pd on carbon (1.0 g) at 60 psi H$_2$ for 24 h at ambient temperature. Filtration of the catalyst and evaporation of the solvent gave 3.6 g (93%) of the title compound. FDMS: M$^+$=286. Anal. calcd. for C$_{18}$H$_{22}$O$_3$: C, 75.50; H, 7.74. Found: C, 75.71; H, 7.78.

(c) 1SR,2SR,3SR,5RS,6SR-Ethyl-2-aminoacetyl-2-cyano-3-((2,5-dimethyl)benzyl)bicyclo[3.1.0]hexane-6-carboxylate and 1SR,2RS,3SR,5RS,6SR-Ethyl-2-aminoacetyl-2-cyano-3-((2,5-dimethyl)benzyl)bicyclo [3.1.0]hexane-6-carboxylate. A mixture of KCN (3.7 g, 56 mmol), NH$_4$Cl (3.0 g, 56 mmol) and Al$_2$O$_3$ (37 g) in CH$_3$CN were sonicated under N$_2$ in a Branson 3200 ultrasonic bath for 1 hr. Then the product of step (b) (0.6 g, 5.6 mmol) was added and sonicated for 72 hrs at 45° C. The reaction mixture was filtered through Celite® and the filtrate was concentrated to dryness. The intermediate amino nitrile so obtained was dissolved in CH$_2$Cl$_2$, cooled to 0° C., and treated with acetyl chloride (1.5 g, 19.2 mmol) and N,N-diisopropylethylamine (2.5 g, 19.2 mmol) in CH$_2$Cl$_2$. The reaction was allowed to proceed at ambient temperature for 1 h, then the mixture was partitioned between CH$_2$Cl$_2$ and H$_2$O. The organic phase was separated, dried (MgSO$_4$) and concentrated under reduced pressure. The crude product was purified by HPLC (10% EtOAc/hexane to 80% EtOAc/hexane). From this was obtained 1.0 g (50%) 1SR, 2SR, 3SR, 5RS, 6SR-ethyl-2-aminoacetyl-2-cyano-3-((2,5-dimethyl)benzylbicyclo[3.1.0]hexane-6-carboxylate (A) and 0.70 g (35%) of 1SR,2SR,3SR,5RS,6SR-ethyl-2-aminoacetyl-2-cyano-3-((2,5-dimethyl)benzylbicyclo [3.1.0]hexane-6-carboxylate (B). (A) mp=177–178° C. FDMS: M$^+$=354. Anal. calcd. for C$_{21}$H$_{26}$N$_2$O$_3$.0.4 H$_2$O: C, 69.74; H, 7.47; N, 7.75. Found: C, 69.62; H, 7.33; N, 7.92. (B): mp=184–186° C. FDMS: M$^+$+1=355. Anal. calcd. for C$_{21}$H$_{26}$N$_2$O$_3$: C, 71.16; H, 7.39; N, 7.90. Found: C, 71.86; H, 7.14; N, 8.33. nOe Confirmation of stereochemistry.

(d) 1SR,2SR,3SR,5RS,6SR-ethyl-2-aminoacetyl-2-cyano-3-((2,5-dimethyl)benzyl)bicyclo[3.1.0]hexane-6-carboxylate from step(c) (0.8 g, 2.4 mmol) was heated under reflux in 5N HCl overnight. The reaction mixture was then concentrated to dryness and purified by anion exchange chromatography (Bio-Rad AG® 1-X8, eluted with aqueous pyridine). Concentration of the eluent gave a white solid which was washed with H$_2$O to yield 0.11 g (15%) of the title compound. mp>250°. Anal. calcd. for C$_{17}$H$_{21}$N$_1$O$_4$-0.2 H$_2$O: C, 67.31; H, 7.03; N, 4.56. Found: C, 66.63; H, 6.99; N, 4.62.

EXAMPLE 3

1SR,2SR,3SR,5RS,6SR-2-Amino-3-((4-phenyl) benzyl)bicyclo[3.1.0]hexane-2,6-dicarboxylic acid (a) 1SR,5RS,6SR-Ethyl-2-oxo-3-(4-phenylbenzylidenyl) bicyclo[3.1.0]hexane-6-carboxylate. The title compound was prepared according to the method of Example 1(a) employing the product of Preparation (2) (5.0 g, 29.7 mmol) and 4-biphenylcarboxaldehyde (6.5 g, 35.8 mmol) followed by dehydration of the intermediate carbinol with catalytic TsOH and refluxing toluene. The crude product was purified by HPLC (10% EtOAc/hexane to 50% EtOAc/hexane) and recrystallized using EtOAc/hexane to give 3.7 g (37%) of the title compound: mp=167–169° C.; FDMS: M$^+$+1=333; Anal. calcd. for C$_{22}$H$_{20}$O$_3$.0.5H$_2$O: C, 78.43; H, 6.13. Found: C, 78.67; H, 6.20

(b) 1SR,3RS,5RS,6SR-Ethyl-2-oxo-3-((4-phenyl) benzyl)-bicylo[3.1.0]hexane-6-carboxylate. The title compound was prepared according to the method of Example 1(c) employing the product of step (a) (3.5 g, 10.5 mmol) and Raney Ni (0.9 g). The product was purified by HPLC (5% EtOAc/hexane to 40% EtOAc/hexane) to give 2.4 g (69%) of the title compound. FDMS: M$^+$=334. Anal. calcd. for C$_{22}$H$_{22}$O$_3$-0.4 H$_2$O: C, 77.35; H, 6.73. Found: C, 72.24; H, 6.55.

(c) 1SR,3SR,5RS,6SR-Ethyl-2-oxo-3-((4-phenyl)benzyl) bicyclo[3.1.0]hexane-6-carboxylate. To a solution of Na ethoxide (prepared by dissolving Na spheres (0.2 g, 8.7 g-atom) in EtOH (100 mL)) was added the product of step (b) (2.4 g, 7.2 mmol) at ambient temperature. The reaction mixture was allowed to stir at ambient temperature until judged complete by GC, then was acidified with 1 N HCl. The product was partitioned between Et$_2$O and aqueous NaHCO$_3$. The organic phase was separated, dried over MgSO$_4$ and concentrated to dryness affording the title compound (2.2 g, 92%). mp=140–142° C. FDMS: M$^+$=334. Anal. calcd. for C$_{22}$H$_{22}$O$_3$: C, 79.02; H, 6.63. Found: C, 80.18; H, 7.14.

(d) 1SR,2SR,3SR,5RS,6SR-Ethyl-2-aminoacetyl-2-cyano-3-((4-phenyl)benzyl)bicyclo[3.1.0]hexane-6-carboxylate. The title compound was prepared using the method Example 1(d) and employing the product of step (c) (2.1 g, 6.3 mmol), KCN (4.1 g, 63 mmol), NH$_4$Cl (3.0 g, 63 mmol) and Al$_2$O$_3$ (41 g) followed by acetylation with acetyl chloride (1.3 g, 16.8 mmol) and N,N-diisopropylethylamine (2.2 g, 16.8 mmol) in CH$_2$Cl$_2$. The title compound (0.6 g, 26%) was obtained by crystallization from CH$_2$Cl$_2$.

(e) The title compound was prepared by the method of Example 2(d) employing the product of step (d) (0.6 g, 1.5 mmol) in refluxing 2 or 5N HCl. The reaction mixture was evaporated to dryness. The crude product was then dissolved in H$_2$O at pH 10 and filtered. The product was precipitated at pH 3, filtered and washed with H$_2$O, IPA and EtOAc, yielding.0.06 g (11%) of the title compound as a white solid. mp=260–261° C., FDMS: M$^+$–1=350. Anal. calcd. for C$_{21}$H$_{21}$NO$_4$.0.25 NH$_4$Cl: C, 69.65; H, 6.07; N, 4.64. Found: C, 69.92; H, 6.21; N, 4.37.

EXAMPLE 4

1SR,2SR,3SR,5RS,6SR-Amino-3-((3-methyl) benzyl)bicyclo[3.1.0]hexane-2,6-dicarboxylic acid (a) 1SR,5RS,6SR-Ethyl-2-oxo-3-((3-methyl) benzylidenyl)-bicyclo[3.1.0]hexane-6-carboxylate. The title compound was obtained employing the methods of Examples 1(a) and 1(b) using the product of Preparation 2 (6.0 g, 35.7 mmol) and 3-methyl benzaldehyde (5.1 g, 42.8 mmol) followed by dehydration of the intermediate carbinol with catalytic TsOH and refluxing toluene. The crude product was purified by HPLC (5% EtOAc/hexane to 50% EtOAc/hexanes) to yield 7.3 g (76%) of the title compound: mp=105–107° C., FDMS: $M^+$=270. Anal. calcd. for $C_{17}H_{18}O_3$: C, 75.53; H, 6.71. Found: C, 76.61; H, 6.75.

(b) 1SR,3RS,5RS,6SR-Ethyl-2-oxo-3-((3-methyl)benzyl) bicyclo[3.1.0]hexane-6-carboxylate. The title compound was prepared using the method of Example 1(c) employing the product of step (a) (5.8 g, 21.5 mmol) and Raney Ni (1.5 g). Purification by HPLC (5% EtOAc/hexane to 50% EtOAc/hexane) afforded 4.5 g (77%) of the title compound. FDMS: $M^+$=272. Anal. calcd. for $C_{17}H_{20}O_3$: C, 74.97; H, 7.40. Found: C, 75.18; H, 7.44.

(c) 1SR,2SR,3SR,5RS,6SR-Ethyl-2-aminoacetyl-2-cyano-3-((3-methyl)benzyl)bicyclo[3.1.0]hexane-6-carboxylate and 1SR,2RS,3SR,5RS,6SR-Ethyl-2-aminoacetyl-2-cyano-3-((3-methyl)benzyl)bicyclo[3.1.0] hexane-6-carboxylate. The title compounds were prepared using the method of Example 2(c) employing the product of step (b) (3.0 g, 11.0 mmol), KCN (7.2 g, 110 mmol), $NH_4Cl$ (5.9 g, 110 mmol) and $Al_2O_3$ (40 g) folled by acylation with acetyl chloride (2.4 g, 30.3 mmol) and N,N-diisopropylethylamine (3.9 g, 30.3 mmol). The crude product was purified by HPLC (10% EtOAc/hexane to 80% EtOAc/hexane). From this was obtained 2.2 g (58%) of 1SR, 2SR, 3SR, 5RS, 6SR-ethyl-2-aminoacetyl-2-cyano-3-((3-methyl)benzyl)bicyclo[3.1.0]hexane-6-carboxylate (A) and 0.90 g, (24%) of 1SR, 2RS, 3SR, 5RS, 6SR-ethyl-2-aminoacetyl-2-cyano-3-((3-methyl)benzyl)bicyclo[3.1.0] hexane-6-carboxylate (B). (A): mp=166–168° C. FDMS: $M^+$=340. Anal. calcd. for $C_{20}H_{24}O_3N_2$: C, 70.57; H, 7.11; N, 8.23. Found: C, 70.35; H, 7.17; N, 8.39. (B): mp=58–62° C. FDMS: $M^++1$=341. Anal. calcd. for $C_{20}H_{24}O_3N_2$: C, 70.57; H, 7.11; N, 8.23. Found: C, 70.80; H, 7.19; N, 8.23. nOE confirmation of stereochemistry.

(d) The title compound was prepared using the method of Example 3(e) employing the product of step (c) (1.0 g, 2.9 mmol) in refluxing 5N HCl. 0.64 g (75%) of the title compound was collected. mp>250° C., FDMS: $M^++1$=290. Anal. calcd. for $C_{16}H_{19}N_1O_4$: C, 66.42; H, 6.62; N, 4.84. Found: C, 66.58; H, 6.52; N, 4.59.

EXAMPLE 5

1SR,2SR,3SR,5RS,6SR-2-Amino-3-((2,4-dimethyl) benzyl)bicyclo[3.1.0]hexane-2,6-dicarboxylie acid (a) 1SR,5RS,6SR-Ethyl-2-oxo-3-(2,4-dimethylbenzylidenyl)bicyclo[3.1.0]hexane-6-carboxylate. The title compound was prepared by the method of Example 1(a) employing the product of Preparation 2 (8.1 g, 48.1 mmol) and 2,4-dimethylbenzaldehyde (7.74 g, 57.8 mmol). Dehydration of the intermediate carbinol was achieved by refluxing with TsOH in toluene. The crude product was purified by HPLC (10% EtOAc/hexane to 50% EtoAc/hexane) affording 1.6 g (12%) of the title compound: mp=67–69° C.; FDMS: $M^+$=284; Anal. calcd. for $C_{18}H_{20}O_3$: C, 76.03; H, 7.09. Found: C, 76.13; H, 7.18.

(b) 1SR,3RS,5RS,6SR-Ethyl-2-oxo-3-(2,4-dimethyl) benzyl)bicyclo[3.1.0]hexane-6-carboxylate. The title compound was prepared using the method of Example 1(c), but employing the product of step(a) (1.6 g, 5.6 mmol) and Raney Ni (0.4 g). The product was purified by HPLC (5% EtOAc/hexane to 50% EtOAc/hexane) yielding 1.0 g (62%) of the title compound.

(c) 1SR,3SR,5RS,6SR-Ethyl-2-oxo-3-(2,4-dimethyl) benzyl)bicyclo[3.1.0]hexane-6-carboxylate. The title compound was prepared using the method of Example 3(c) employing the product of step(b) (1.0 g, 3.5 mmol) and Na metal (0.1 g, 4.3 g-atom). Extractive workup gave 1.0 g (99%) of the title compound. FDMS: $M^+$=286. Anal. calcd. for $C_{18}H_{22}O_3$: C, 75.50; H, 7.74. Found: C, 75.61; H, 7.51.

(d) 1SR,2SR,3SR,5RS,6SR-Ethyl-2-aminoacetyl-2-cyano-3-((2,4-dimethyl)benzyl)bicyclo[3.1.0]hexane-6-carboxylate and 1SR,2RS,3SR,5RS, 6SR-Ethyl-2-aminoacetyl-2-cyano-3-((2,4-dimethyl)benzyl)bicyclo [3.1.0]hexane-6-carboxylate. The title compounds were prepared by the method of Example 2(c) employing the product of step (c) (1.2 g, 4.2 mmol), $NH_4Cl$ (2.2 g, 42 mmol), KCN (2.7 g, 42 mmol), $Al_2O_3$ (48 g). The crude amino nitrile was acetylated with acetyl chloride (0.4 g, 5 mmol) and N,N-diisopropyl ethylamine (0.6 g, 5 mmol). Purification by HPLC (10% EtOAc/hexane to 80% EtOAc/hexane) afforded 0.5 g (34%) of 1SR, 2SR, 3SR, 5RS, 6SR-ethyl-2-aminoacetyl-2-cyano-3-((2,4-dimethyl)benzyl) bicyclo[3.1.0]hexane-6-carboxylate (A) and 0.4 g (27%) of and 1SR, 2RS, 3SR, 5RS, 6SR-ethyl-2-aminoacetyl-2-cyano-3-((2,4-dimethyl)benzyl)bicyclo[3.1.0]hexane-6-carboxylate (B). (A): mp=207–208° C., FDMS: $M^+$=354 Anal. calcd. for $C_{21}H_{26}N_2O_3$: C, 71.16; H, 7.39; N, 7.90. Found: C, 71.34; H, 7.44; N, 7.67. (B): mp=103–105° C., FDMS: $M^+$=354 Anal. calcd. for $C_{21}H_{26}N_2O_3 \cdot 0.7$ EtOAc: C, 68.70; H, 7.65; N, 6.73. Found: C, 68.82; H, 7.48; N, 6.94.

(e) The title compound was prepared by the method of Example 3(e) employing 1SR,2SR,3SR,5RS,6SR-ethyl-2-aminoacetyl-2-cyano-3-((2,4-dimethyl)benzyl)bicyclo [3.1.0]hexane-6-carboxylate from step (d) (0.32 g, 0.9 mmol) in refluxing 5N HCl, yielding 0.235 g (86%) of the title compound mp>250° C., FDMS: $M^+$=303; Anal. calcd. for $C_{17}H_{21}NO_4$: C, 67.31; H, 6.98; N, 4.62. Found: C, 67.10; H, 7.07; N, 4.89.

EXAMPLE 6

1SR,2SR,3SR,5RS,6SR-Amino-3-((4-(2-propyl)) benzyl)bicyclo[3.1.0]hexane-6-carboxylic acid (a) 1SR,5RS,6SR-Ethyl-2-oxo-3-((4-(2-propyl)) benzylidenyl)bicyclo[3.1.0]hexane-6-carboxylate. The title compound was prepared using the method of Example 1(a) employing the product of Preparation 2 (4.2 g, 25 mmol), and 4-isopropylbenzaldehyde (4.4 g, 30 mmol). Dehydration of the intermediate carbinol was effected with catalytic TsOH in refluxing toluene. The crude product was purified by HPLC (5% EtOAc/hexane to 50% EtOAc/hexane) yielding 2.7 g (36%) of the title compound: FDMS: $M^+$=298. Anal. calcd. for $C_{19}H_{22}O_3$: C, 76.48; H, 7.43. Found: C, 76.43; H, 7.41.

(b) 1SR,3RS,5RS,6SR-Ethyl-2-oxo-3-((4-(2-propyl)) benzyl)bicyclo[3.1.0]hexane-6-carboxylate. The title compound was prepared using the method of Example 1(c) employing the product of step (a) (2.1 g, 7 mmol) and Raney Ni (0.5 g). The crude product was purified by HPLC (5% EtOAc/hexane to 50% EtOAc/hexane) yielding 1.8 g (85%)

of the title compound. FDMS: M$^+$=300. Anal. calcd. for C$_{19}$H$_{24}$O$_3$: C, 75.97; H, 8.05. Found: C, 75.87; H, 8.05.

(c) 1SR,3SR,5RS,6SR-Ethyl-2-oxo-3-((4-(2-propyl))benzyl)bicyclo[3.1.0]hexane-6-carboxylate. The title compound was prepared using the method of Example 3(c) employing the product of step (b) (1.8 g, 5.9 mmol) and Na (0.15 g, 6.5 g-atom). Extractive workup afforded 1.8 g (99%) of the title compound. FDMS: M$^+$=300. Anal. calcd. for C$_{19}$H$_{24}$O$_3$: C, 75.97; H,8.05. Found: C, 76.19; H, 7.80.

(d). 1SR,2SR,3SR,5RS,6SR-Ethyl-2-aminoacetyl-2-cyano-3-((4-(2-propyl))benzyl)bicyclo[3.1.0]hexane-6-carboxylate and 1SR,2RS,3SR,5RS,6SR-Ethyl-2-aminoacetyl-2-cyano-3-((4-(2-propyl))benzyl)bicyclo[3.1.0]hexane-6-carboxylate. The title compounds were prepared by the method of Example 2(c) employing the product of step (c) (1.7 g, 5.7 mmol), KCN (3.7 g, 57 mmol), NH$_4$Cl (3.1 g, 57 mmol) and Al$_2$O$_3$ (50 g). The intermediate amino nitrile was acylated using acetyl chloride (0.6 g, 7 mmol) and N,N-diisopropylethylamine (0.9 g, 7 mmol). The crude product was purified by HPLC (10% EtOAc/hexane to 90% EtOAc/hexane) yielding 0.8 g (38%) of 1SR, 2SR, 3SR, 5RS, 6SR-ethyl-2-aminoacetyl-2-cyano-3-((4-(2-propyl))benzyl)bicyclo[3.1.0]hexane-6-carboxylate (A) and 0.3 g (14%) of 1SR, 2RS, 3SR, 5RS, 6SR-ethyl-2-aminoacetyl-2-cyano-3-((4-(2-propyl))benzyl)bicyclo[3.1.0]hexane-6-carboxylate (B). (A): mp=225–227° C. FDMS: M$^+$=368. Anal. calcd. for C$_{22}$H$_{28}$N$_2$O$_3$: C, 71.71; H, 7.66; N, 7.60. Found: C, 71.56; H, 7.59; N, 7.62. (B): mp=71–80° C. FDMS: M$^+$=368. Anal. calcd. for C$_{22}$H$_{28}$N$_2$O$_3$: C, 71.71; H, 7.66; N, 7.60. Found: C, 71.76; H, 7.62; N, 7.58.

(e) The title compound was prepared by employing the 2SR diastereomer product of step (d) (0.6 g, 1.6 mmol) in refluxing 5N HCl (50 mL) overnight. The reaction mixture was concentrated to dryness yielding 0.53 g (89%) of the title compound without further purification. mp=>250° C. FDMS: M$^+$=317; Anal. calcd. for C$_{18}$H$_{24}$ClNO$_4$.0.25 NH$_4$Cl: C, 58.87; H, 6.86; N, 4.77. Found: C, 58.74; H, 6.93; N, 5.54.

EXAMPLE 7

1SR,2SR,3SR,5RS,6SR-2-Amino-3-((3-methyl-4-methoxy)benzyl)bicyclo[3.1.0]hexane-6-carboxylic acid (a) 1SR,5RS,6SR-Ethyl-2-oxo-3-((3-methyl-4-methoxy)benzylidenyl)bicyclo[3.1.0]hexane-6-carboxylate. The title compound was prepared using the method described in Examples 1(a) and 1(b) employing the product of Preparation 2 (4.2 g, 25 mmol) and 3-methyl-p-anisaldehyde (4.5 g, 30 mmol). Dehydration of the intermediate carbinol was effected with catalytic TsOH in refluxing toluene. The crude product was purified by HPLC (5% EtOAc/hexane to 50% EtOAc/hexane) yielding 5.2 g (69%) of the title compound: mp=126–128° C., FDMS: M$^+$=300; Anal. calcd. for C$_{18}$H$_{20}$O$_4$: C, 71.98; H, 6.71. Found: C, 71.99; H, 6.77.

(b) 1SR,3RS,5RS,6SR-Ethyl-2-oxo-3-((3-methyl-4-methoxy)benzyl)bicyclo[3.1.0]hexane-6-carboxylate. The title compound was prepared by the method of Example 1(c) employing the product of step (a) (3.5 g, 11.7 mmol) and Raney Ni (0.88 g) yielding 3.4 g (96%) of the title compound. FDMS: M$^+$=302; Anal. calcd. for C$_{18}$H$_{22}$O$_4$-0.2 H$_2$O: C, 70.66; H, 7.37. Found: C, 70.59; H, 7.42.

(c) 1SR,3SR,5RS,6SR-Ethyl-2-oxo-3-((3-methyl-4-methoxy)benzyl)bicyclo[3.1.0]hexane-6-carboxylate. The title compound was prepared by the method of Example 3(c) employing the product of step (b) (2.9 g, 9.6 mmol) and Na (0.23 g, 10.1 g-atom). Work up yielded 1.8 g (62%) of the title compound. FDMS: M$^+$=302; Anal. calcd. for C$_{18}$H$_{22}$O$_4$: C, 71.50; H, 7.33. Found: C, 71.20; H, 7.06.

(d) 1SR,2SR,3SR,5RS,6SR-Ethyl-2-aminoacetyl-2-cyano-3-((3-methyl-4-methoxy)benzyl)bicyclo[3.1.0]hexane-6-carboxylate and 1SR,2SR,3SR,5RS,6SR-Ethyl-2-aminoacetyl-2-cyano-3-((3-methyl-4-methoxy)benzyl)bicyclo[3.1.0]hexane-6-carboxylate. The title compounds were prepared according to the method of Example 2(c) employing the product of step (c) (1.7 g, 5.6 mmol), NH$_4$Cl (3.0 g, 56.2 mmol), KCN (3.7 g, 56.2 mmol) and Al$_2$O$_3$ (40 g). The intermediate amino nitrile was acetylated with acetyl chloride (0.6 g, 7.8 mmol) and N,N-diisopropylethylamine (1.0 g, 7.8 mmol). The crude product was purified by HPLC (10% EtOAc/hexane to 80% EtOAc/hexane) yielding 1.0 g (48%) of 1SR,2SR,3SR,5RS,6SR-ethyl-2-aminoacetyl-2-cyano-3-((3-methyl-4-methoxy)benzyl)bicyclo[3.1.0]hexane-6-carboxylate (A) and 0.6 g (29%) of 1SR,2RS,3SR,5RS,6SR-ethyl-2-aminoacetyl-2-cyano-3-((3-methyl-4-methoxy)benzyl)bicyclo[3.1.0]hexane-6-carboxylate (B). (A): mp=211–212° C., FDMS: M$^+$=370; Anal. calcd. for C$_{21}$H$_{26}$N$_2$O$_4$: C, 68.09; H, 7.07; N, 7.56. Found: C, 68.07; H, 7.13; N, 7.62. (B): mp=147–149° C.; FDMS: M$^+$=370; Anal. calcd. for C$_{21}$H$_{26}$N$_2$O$_4$.0.25 EtOAc: C, 67.33; H, 7.19; N, 7.14. Found: C, 67.57; H, 7.17; N, 6.82.

(e) 1SR,2SR,3SR,5RS,6SR-2-Amino-3-((3-methyl-4-methoxy)benzyl)bicyclo[3.1.0]hexane-2,6-dicarboxylate. The title compound was prepared by the method of Example 3(e) employing the product of step (d) (0.25 g, 0.65 mmol). After work up, acidification with CH$_3$CO$_2$H, 0.165 g (77%) of the title compound was obtained. mp>275° C., FDMS: M$^+$=319. Anal. calcd. for C$_{17}$H$_{21}$NO$_5$.0.33CH$_3$CO$_2$H: C, 60.07; H, 5.58; N, 4.47. Found: C, 63.13; H, 6.59; N, 4.43.

EXAMPLE 8

1SR,2SR,3SR,5RS,6SR-2-Amino-3-((2-methyl)benzyl)bicyclo[3.1.0]hexane-2,6-dicarboxylic acid (a) 1SR,5RS,6SR-Ethyl-2-oxo-3-((2-methyl)benzylidenyl)bicyclo[3.1.0]hexane-6-carboxylate. The title compound was obtained by the method of Example 1(a) employing the product of Preparation 2 (4.0 g, 23.8 mmol) and 2-methylbenzaldehyde (3.4 g, 28.6 mmol). Dehydration of the intermediate carbinol was effected with catalytic TsOH in refluxing toluene. The crude product was purified by HPLC (10% EtOAc/hexane to 50% EtOAc/hexane) yielding 4.0 g (62%) of the title compound. mp=73–74° C.; FDMS: M$^+$=270; Anal. calcd. for C$_{17}$H$_{18}$O$_3$: C, 75.52; H, 6.72. Found: C, 75.61; H, 6.89.

(b) 1SR,3RS,5RS,6SR-Ethyl-2-oxo-3-((2-methyl)benzyl)bicyclo[3.1.0]hexane-6-carboxylate. The title compound was prepared by the method of Example 1(c) employing the product of step (a) (3.0 g, 11.1 mmol) and Raney Ni (0.75 g). Filtration of the catalyst and evaporation gave 2.5 g (81%) of the title compound. FDMS: M$^+$=272. Anal. calcd. for C$_{17}$H$_{20}$O$_3$: C, 74.97; H, 7.40. Found: C, 74.94; H, 7.54.

(c) 1SR,3SR,5RS,6SR-Ethyl-2-oxo-3-((2-methyl)benzyl)bicyclo[3.1.0]hexane-6-carboxylate. The title compound was prepared by the method of Example 3(c) employing the product of step (b) (2.5 g, 9.2 mmol). Extractive workup afforded 2.4 g (96%) of the title compound. mp=67–69° C., FDMS: M$^+$=272; Anal. calcd. for C$_{17}$H$_{20}$O$_3$: C, 74.97; H, 7.40. Found: C; 75.23; H, 7.29.

(d) 1SR,2SR,3SR,5RS,6SR-Ethyl-2-aminoacetyl-2-cyano-3-((2-methyl)benzyl)bicyclo[3.1.0]hexane-6- carboxylate and 1SR,2RS,3SR,5RS,6SR-Ethyl-2-aminoacetyl-2-cyano-3-((2-methyl)benzyl)bicyclo[3.1.0]hexane-6-carboxylate. The title compounds were prepared according to the method of Example 2(c) employing the product of step (c) (2.2 g, 8.1 mmol), $NH_4Cl$ (4.3 g, 80.7 mmol), KCN (5.3 g, 80.7 mmol) and $Al_2O_3$ (41 g). Acetylation of the intermediate amino nitrile (2 g, 6.75 mmol) with acetyl chloride (0.8 g, 10 mmol) and N,N-diisopropylethylamine (1.3 g, 10 mmol). Purification of the crude product by HPLC (10% EtOAc/hexane to 90%EtOAc/hexane) yielded 0.78 g (28%) of 1SR,2SR,3SR,5RS,6SR-Ethyl-2-aminoacetyl-2-cyano-3-((2-methyl)benzyl)bicyclo [3.1.0]hexane-6-carboxylate (A) and 0.50 g (18%) of 1SR,2RS,3SR,5RS,6SR-Ethyl-2-aminoacetyl-2-cyano-3-((2-methyl)benzyl)bicyclo [3.1.0]-hexane-6-carboxylate (B). (A): mp=212–213° C. FDMS: $M^+$=340. Anal. calcd. for $C_{20}H_{24}N_2O_3$: C, 70.57; H, 7.11; N, 8.23. Found: C, 70.86; H, 6.95; N, 8.45. (B): FDMS: $M^+$=340. Anal. calcd. for $C_{20}H_{24}N_2O_3$: C, 70.57; H, 7.11; N, 8.23. Found: C, 70.33; H, 7.16; N, 8.46.

(e) 1SR,2SR,3SR,5RS,6SR-2-Amino-3-((2-methyl)benzyl)bicyclo[3.1.0]hexane-2,6-dicarboxylate. The title compound was prepared by employing 1SR,2SR,3SR,5RS,6SR-ethyl-2-aminoacetyl-2-cyano-3-((2-methyl)benzylbicyclo[3.1.0]hexane-6-carboxylate from step (d) (0.65 g, 2 mmol) in refluxing 5N HCl (35 mL) overnight. Concentration of the reaction mixture to dryness yielded 0.6 g (85%) of the title compound. mp=>250° C., FDMS: $M^+$=289; Anal. calcd. for $C_{16}H_{19}NO_4.HCl.0.9\ NH_4Cl$: C, 51.39; H, 6.36; N, 7.12. Found: C, 51.38; H, 6.37; N, 7.27.

EXAMPLE 9

1SR,2SR,3SR,5RS,6SR-2-Amino-3-benzylbicyclo[3.1.0]hexane-2,6-carboxylic acid (a) 1SR,5RS,6SR-2-Oxo-3-benzylidenylbicyclo[3.1.0]hexane-6-carboxylate. A solution of the product of Preparation 2 (1.68 g, 10.0 mmol) and benzaldehyde (1.17 g, 11.0 mmol) in 1 N NaOH (25 mL) was vigorously stirred at ambient temperature for 72 h. The reaction mixture was partitioned between 1N NaOH and Et2O and the organic phase was discarded. The aqueous phase was acidified with 5 N HCl and extracted with $Et_2O$. The organic phase was dried ($MgSO_4$) and concentrated under reduced pressure to afford 2.24 g (98%) of the title compound: FDMS: $M^+$=228; Anal. calcd. for $C_{14}H_{12}O_3$: C, 73.67; H, 73.49. Found: C, 73.49; H, 5.39.

(b) 1SR,3SR,5RS,6SR-Ethyl-2-oxo-3-(phenylhydroxymethyl)bicyclo[3.1.0]hexane-6-carboxylate. Prepared essentially as in the method of Example 1(a) employing the product of Preparation 2 (5.24 g, 31.2 mmol) and benzaldehyde (5.06 g, 46.8 mmol) in the absence of $BF_3.Et_2O$. The crude carbinol product was purified by HPLC (10% EtOAc/hexane to 50% EtOAc/hexane) yielding 5.02 g (59%) of the title compound. FDMS: $M^+$=274; Anal. calcd. for $C_{16}H_{18}O_4$: C, 70.06; H, 6.61. Found: C, 70.85; H, 6.53.

(c) 1SR,3SR,5RS,6SR-Ethyl-2-oxo-3-benzylbicyclo [3.1.0]-hexane-6-carboxylate. The title compound was prepared by hydrogenolysis of the product of step (b) (1.3 g, 4.7 mmol) in THF (50 mL) employing 5% Pd on carbon (0.33 g) at 60 psi $H_2$ for 24 h. The product was purified by HPLC (10% EtOAc/hexane to 33% EtOAc/hexane) to yield 0.76 g (63%) of the title compound: FDMS: $M^+$=258; Anal. calcd. for $C_{16}H_{18}O_3$: C, 74.40; H, 7.02. Found: C, 74.60; H, 7.12.

(d) 1SR,2SR,3SR,5RS,6SR-Ethyl-2-aminoacetyl-2-cyano-3-benzylbicyclo[3.1.0]hexane-6-carboxylate. The title compound was prepared by the method of Example 2(c) employing the product of step (c) (0.52 g, 2.0 mmol), KCN (1.3 g, 20 mmol), $NH_4Cl$ (1.1 g, 20 mmol) and $Al_2O_3$ (13 g). The intermediate amino nitrile was acylated using acetyl chloride (0.5 g, 6.3 mmol) and N,N-diisopropylethylamine (1.3 g, 1.0 mmol). The crude product was purified by HPLC (33% EtOAc/hexane to 67% EtOAc/hexane) yielding 0.1 g (15%) of the title compound. mp=202–204° C.; FDMS: $M^+$=326. Anal. calcd. for $C_{19}H_{22}N_2O_3$: C, 69.92; H, 6.79; N, 8.58. Found: C, 69.76; H, 7.06; N, 8.29. nOe confirmation of stereochemistry.

(e) 1SR,2SR,3SR,5RS,6SR-2-Amino-3-benzylbicyclo [3.1.0]hexane-2,6-dicarboxylate. The title compound prepared by the method of Example 2(d) employing the product of step (d) (0.07 g, 0.2 mmol. Purification was achieved by cation exchange chromatography (Dowex 50WX8-100 cation exchange resin) yielding 0.045 g (76%) of the title compound. mp=252–253° C., FDMS: $M^++1$=276. Anal. calcd. for $C_{15}H_{17}NO_4$-0.4 $H_2O$: C, 63.77; H, 6.35; N, 4.96. Found: C, 63.76; H, 6.29; N, 4.81.

EXAMPLE 10

1SR,2RS,3SR,5RS,6SR-2-Amino-3-((2-chloro)benzyl)bicyclohexane[3.1.0]hexane-2,6-dicarboxylic acid (a) 1SR,5RS,6SR-2-Oxo-3-((2-chloro)benzylidenyl)bicyclo[3.1.0]hexane-6-carboxylic acid. The title compound was prepared by the method of Example 1(a) employing the product of Preparation 2 (8.41 g, 50.0 mmol) and 2-chlorobenzaldehyde (8.0 g, 57 mmol). The product was isolated by filtering the precipitate which occurred on acidification of the aqueous phase, yielding 13.1 g, 99%) of the title compound: mp=183–185° C.; FDMS: $M^+$=262; Anal. calcd. for $C_{14}H_{11}ClO_3$: C, 64.01, H, 4.22. Found: C, 64.26; H, 4.31. $^{13}$C-NMR (DMSO) 25.17, 28.06, 30.17, 35.36, 128.00, 128.99, 130.41, 130.47, 131.52, 132.77, 135.14, 136.39, 171.73, 200.75.

(b) 1SR,5RS,6SR-Ethyl-2-oxo-3-((2-chloro)benzylidenyl)bicyclo[3.1.0]hexane-6-carboxylate. To a solution of the product of step(a)(12.2 g, 46.5 mmol), $Et_3N$ (5.18 g, 51.1 mmol) and DMAP (0.57 g, 4.65 mmol) in $CH_2Cl_2$ (250 mL) at 5° C. was added ethyl chloroformate (8.23 g, 51.2 mmol) in $CH_2Cl_2$ (25 mL) dropwise over a period of 10 minutes. After stirring at ambient temperature overnight, the reaction mixture was partitioned between $CH_2Cl_2$ and saturated aqueous $NaHCO_3$. The organic phase was separated, washed with 1 N HCl, dried ($MgSO_4$) and concentrated under reduced pressure to give 13.2 g (98%) of the title compound: mp=95–96° C.; FDMS: $M^+$=290; Anal. calcd. for $C_{16}H_{15}ClO_3$: C, 66.10, H, 5.20. Found: C, 66.08; H, 5.27.

(c) 1SR,3RS,5RS,6SR-Ethyl-2-oxo-3-((2-chloro)benzyl)bicyclo[3.1.0]hexane-6-carboxylate. The title compound was prepared by the method of Example 1(c) employing the product of step (b) (6.0 g, 20.7 mmol) and Raney Ni (1.5 g). The crude product was purified by HPLC (5% EtOAc/hexane to 50% EtOAc/hexane) yielding 5.6 g (93%) of the title compound. FDMS: $M^+$=292; Anal. calcd. for $C_{16}H_{17}ClO_3$: C, 65.64; H, 5.85. Found: C, 65.34; H, 5.56.

(d) 1SR,3SR,5RS,6SR-Ethyl-2-oxo-3-((2-chloro)benzyl) bicyclo [3.1.0]hexane-6-carboxylate. The title compound was prepared by the method of Example 3(c) employing the product of step (c) (5.3 g, 18.1 mmol) and Na (0.44 g, 19 g-atom). Work up yielded 3.0 g (57%) of the title compound.

(e) 1SR,2SR,3SR,5RS,6SR-Ethyl-2-aminoacetyl-2-cyano-3-((2-chloro)benzyl)bicyclo[3.1.0]hexane-6- carboxylate and 1SR,2RS,3RS,5RS,6SR-Ethyl-2-aminoacetyl-2-cyano-3-((2-chloro)benzyl)bicyclo[3.1.0]hexane-6-carboxylate. The title compounds were prepared by the method of Example 2(c) employing the product of step (d) (3.0 g, 10.2 mmol), $NH_4Cl$ (5.5 g, 103 mmol), KCN (6.7 g, 103 mmol) and $Al_2O_3$ (50 g). The intermediate amino nitrile was acetylated with acetyl chloride (1.2 g, 15.1 mmol) and N,N-diisopropylethylamine (2.0 g, 15.1 mmol). The crude product was purified by HPLC (10% EtOAc/hexane to 80% EtOAc/hexane) yielding 1.0 g (27%) of 1SR,2SR,3SR,5RS,6SR-ethyl-2-aminoacetyl-2-cyano-3-((2-chloro)benzyl)bicyclo[3.1.0]hexane-6-carboxylate (A) and 1.2 g (33%) of a mixture of (A) and 1SR,2RS,3SR,5RS,6SR-ethyl- 2-aminoacetyl-2-cyano-3-((2-chloro)benzyl)bicyclo[3.1.0]hexane-6-carboxylate (B). (A): mp=229–232° C.; FDMS: $M^+$=360. Anal. calcd. for $C_{19}H_{21}ClN_2O_3$: C, 63.24; H, 5.87; N, 7.76. Found: C, 62.74; H, 6.15; N, 7.82. (B): mp=67–82° C.; FDMS: $M^+$=360. Anal. calcd. for $C_{19}H_{21}ClN_2O_3$: C, 63.24; H, 5.87; N, 7.76. Found: C, 63.28; H, 5.97; N, 7.55.

(f) The title compound was prepared by the method of Example 3(e) employing 1SR,2SR,3SR,5RS,6SR-ethyl-2-aminoacetyl-2-cyano-3-((2-chloro)benzyl)bicyclo[3.1.0]hexane-6-carboxylate from step (e) (0.20 g, 0.55 mmol). After work up, 0.12 g (70%) of the title compound was obtained. mp=145–146° C., FDMS: $M^+$+1=310. Anal. calcd. for $C_{16}H_{19}NO_5$: C, 56.52; H, 5.38; N, 4.39. Found: C, 56.33; H, 5.32; N, 4.42.

EXAMPLE 11

1SR,2SR,3SR,5RS,6SR-2-Amino-3-((3-chloro)benzyl)bicyclo[3.1.0]hexane-2,6-carboxylic acid a) 1SR,5RS,6SR-2-Oxo-3-((3-chloro)benzylidenyl)bicyclo[3.1.0]hexane-6-carboxylic acid. The title compound was prepared by the method of Example 9(a) employing the product of Preparation 2 (8.41 g, 50.0 mmol) and 3-chlorobenzaldehyde (8.0 g, 57 mmol). The product was isolated by filtering the precipitate obtained after acidification of the aqueous phase, yielding 13.2 g (100%) of the title compound. FDMS: $M^+$=262; Anal. calcd. for $C_{14}H_{11}ClO_3$: C, 64.01, H, 4.22. Found: C, 64.23; H, 4.30. $^{13}$C-NMR (DMSO) 25.62, 28.53, 30.96, 35.80, 129.62, 130.18, 130.76, 131.52, 132.72, 134.47, 135.81, 137.71, 172.18, 201.25.

(b) 1SR, 5RS, 6SR-Ethyl-2-oxo-3-((3-chloro)benzylidenyl)bicyclo[3.1.0]hexane-6-carboxylate. The title compound was prepared by the method of Example 10(b) employing the product of step (a) (11.6 g, 44.2 mmol), $Et_3N$ (4.92 g, 48.6 mmol), DMAP (0.54 g, 4.42 mmol) and ethyl chloroformate (7.58 g, 48.6 mmol). The crude product (11.1 g) was purified by HPLC (10% EtOAc/hexane to 50% EtOAc/hexane) affording 9.5 g (74%) of the title compound: mp=79–81° C.; FDMS: $M^+$=290; Anal. calcd. for $C_{16}H_{15}ClO_3$: C, 66.10, H, 5.20. Found: C, 66.10; H, 5.20.

(c) 1SR,3RS,5RS,6SR-Ethyl-2-oxo-3-((3-chloro)benzyl)bicyclo[3.1.0]hexane-6-carboxylate. The title compound was prepared according to the method of Example 1(c) employing the product of step (b) (7.0 g, 24.1 mmol) and Raney Ni (1.75 g) Evaporation of the solvent yielded 6.8 g (96%) of the title compound. FDMS: $M^+$=292; Anal. calcd. for $C_{16}H_{17}ClO_3$: C, 65.64; H, 5.85; N. Found: C, 65.98; H, 5.95.

(d) 1SR,3SR,5RS,6SR-Ethyl-2-oxo-3-((3-chloro)benzyl)bicyclo [3.1.0]hexane-6-carboxylate. The title compound was prepared according to the method of Example 3(c) employing the product of step (c) (6.5 g, 22.2 mmol) and Na (0.51 g, 22.1 g-atom). The crude product was purified by HPLC (10% EtOAc/hexane to 50% EtOAc/hexane) yielding 3.8 g (58%) of the title compound. FDMS: $M^+$=292; Anal. calcd. for $C_{16}H_{17}ClO_3$: C, 65.64; H, 5.85; N. Found: C, 65.90; H, 5.84.

(e) 1SR,2SR,3SR,5RS,6SR-Ethyl-2-aminoacetyl-2-cyano-3-((3-chloro)benzyl)bicyclo[3.1.0]hexane-6-carboxylate and 1SR,2RS,3SR,5RS,6SR-ethyl-2-aminoacetyl-2-cyano-3-((3-chloro)benzyl)bicyclo[3.1.0]hexane-6-carboxylate. The title compounds were prepared according to the method of Example 2(c) employing the product of step (d) (3.6 g, 12.3 mmol), $NH_4Cl$ (6.5 g, 123 mmol), KCN (8.0 g, 123 mmol) and $Al_2O_3$ (40 g). The resulting amino nitrile was acetylated using acetyl chloride (1.9 g, 24.6 mmol) and N,N-diisopropylethylamine (3.2 g, 24.6 mmol). The crude product was purified by HPLC (10% EtOAc/hexane to 80% EtOAc/hexane) affording 2.2 g (50%) of 1SR,2SR,3SR,5RS,6SR-ethyl-2-aminoacetyl-2-cyano-3-((3-chloro)benzyl)bicyclo[3.1.0]hexane-6-carboxylate (A) and 0.9 g (20%) of 1SR,2RS,3SR,5RS,6SR-ethyl-2-aminoacetyl-2-cyano-3-((3-chloro)benzyl)bicyclo[3.1.0]hexane-6-carboxylate (B). (A): mp;=174–182° C.; FDMS: $M^+$=360; Anal. calcd. for $C_{19}H_{21}ClN_2O_3$: C, 63.24; H, 5.87; N, 7.76. Found: C, 62.95; H, 5.97; N, 8.01. (B): FDMS: $M^+$=360; Anal. calcd. for $C_{19}H_{21}ClN_2O_3$: C, 63.24; H, 5.87; N, 7.76. Found: C, 58.83; H, 6.25; N, 10.57.

(f) The title compound was prepared by the method of Example 3(e) employing the 2SR product of step (e) (1.0 g, 27 mmol). The product was isolated by precipitation at pH 3 yielding 0.535 g (62%) of the title compound. mp=243–244° C., FDMS: $M^+$+1=310. Anal. calcd. for $C_{15}H_{16}ClNO_4$: C, 58.16; H, 5.21; N, 4.52. Found: C, 57.87; H, 5.20; N, 4.40.

EXAMPLE 12

1SR,2SR,3SR,5RS,6SR-2-Amino-3-((2-methoxy)benzylbicyclo[3.1.0]hexane-2,6-dicarboxylic acid (a) 1SR,5RS,6SR-2-Oxo-3-((2-methoxy)benzylidenyl)bicyclo[3.1.0]hexane-6-carboxylic acid. The title compound was prepared by the method of Example 9(a) employing the product of Preparation 2 (8.41 g, 50.0 mmol) and 2-methoxybenzaldehyde (7.49 g, 55.0 mmol). The product was isolated by filtering the precipitate obtained on acidification of the aqueous phase, yielding 12.7 g (98%) of the title compound: mp=180–182° C.; FDMS: $M^+$=258; Anal. calcd. for $C_{15}H_{14}O_4$: C, 69.76, H, 5.46. Found: C, 70.03; H, 5.41.

(b) 1SR,5RS,6SR-Ethyl-2-oxo-3-((2-methoxy)benzylidenyl) bicyclo[3.1.0]hexane-6-carboxylate. The title compound was prepared by the method of Example 10(b) employing the product of step (a) (12.2 g, 47.2 mmol), $Et_3N$ (5.3 g, 52 mmol), DMAP (0.6 g, 4.7 mmol) and ethyl chloroformate (5.6 g, 52 mmol), yielding 13.1 g (97%) of the title compound: mp=72–74° C. FDMS: $M^+$=286; Anal. calcd. for $C_{17}H_{18}O_4$: C, 71.30; H, 6.35. Found: C, 71.40; H, 6.35.

(c) 1SR,3RS,5RS,6SR-Ethyl-2-oxo-3-((2-methoxy)benzyl)bicyclo[3.1.0]hexane-6-carboxylate. The title compound was prepared by the method of Example 1(c) employing the product of step (b) (7.0 g, 24.4 mmol). Evaporation of the solvent yielded 6.9 g (98%) of the product of the title compound. FDMS: $M^+$=288; Anal. calcd. for $C_{17}H_{20}O_4$: C, 70.81; H, 6.99. Found: C, 70.57; H, 7.13.

(d) 1SR,3SR,5RS,6SR-Ethyl-2-oxo-3-((2-methoxy)benzyl)bicyclo[3.1.0]hexane-6-carboxylate. The title compound was prepared using the method of Example 3(c) employing the product of step (c) (6.3 g, 21.9 mmol) and Na (0.53 g, 22.4 g-atom). Work up yielded 6.2 g (98%) of the title compound. mp=76–81° C., FDMS: M+=288; Anal. calcd. for $C_{17}H_{20}O_4$: C, 70.81; H, 6.99. Found: C, 70.75; H, 7.16.

(e) 1SR,2SR,3SR,5RS,6SR-Ethyl-2-aminoacetyl-2-cyano-3-((2-methoxy)benzyl)bicyclo[3.1.0]hexane-6-carboxylate and 1SR,2RS,3SR,5RS,6SR-Ethyl-2-aminoacetyl-2-cyano-3-((2-methoxy)benzyl)bicyclo[3.1.0]hexane-6-carboxylate. The title compounds were prepared by the method of Example 2(c) employing the product of step (d) (3.0 g, 10.4 mmol), $NH_4Cl$ (5.6 g, 104 mmol), KCN (6.8 g, 104 mmol) and $Al_2O_3$ (50 g). The resulting amino nitrile was acetylated using (1.1 g, 13.8 mmol) and N,N-diisopropylethylamine (1.8 g, 13.8 mmol). Purification of the crude product by HPLC (10% EtOAc/hexane to 80% EtOAc/hexane) yielded 1.0 g (27%) of 1SR,2SR,3SR,5RS,6SR-ethyl-2-aminoacetyl-2-cyano-3-((2-methoxy)benzyl)bicyclo[3.1.0]hexane-6-carboxylate (A) and 0.5 g (14%) of a mixture of (A) and 1SR,2RS,3SR,5RS,6SR-ethyl-2-aminoacetyl-2-cyano-3-((2-methoxy)benzyl)bicyclo[3.1.0]hexane-6-carboxylate (B). (A): mp=87–89° C.; FDMS: M+=356; Anal. calcd. for $C_{20}H_{24}N_2O_4$: C, 67.40; H, 6.79; N, 7.86. Found: C, 67.61; H, 6.86; N, 7.80. (B): mp=68–70; FDMS: M+=356; Anal. calcd. for $C_{20}H_{24}N_2O_4$: C, 67.40; H, 6.79; N, 7.86. Found: C, 67.22; H, 6.81; N, 7.70.

(f) The title compound was prepared by the method of Example 3(e) employing 1SR,2SR,3SR,5RS,6SR-ethyl-2-aminoacetyl-2-cyano-3-((2-methoxy)benzyl)bicyclo[3.1.0]hexane-6-carboxylate (0.25 g, 0.7 mmol) from step (e). After work up, 0.18 g (86%) the title compound was obtained. mp=238–239° C.; FDMS: M+=305 Anal. calcd. for $C_{16}H_{19}NO_5$: C, 62.94; H, 6.27; N, 4.59. Found: C, 62.69; H, 6.39; N, 4.32.

EXAMPLE 13

1SR,2SR,3SR,5RS,6SR-2-Amino-3-((3-methoxy)benzylbicyclo[3.1.0]hexane-2,6-dicarboxylic acid (a) 1SR,5RS,6SR-2-Oxo-3-((3-methoxy)benzylidenyl)bicyclo[3.1.0]hexane-6-carboxylic acid. The title compound was prepared by the method of Example 9(a) employing the product of Preparation 2 (8.41 g, 50.0 mmol) and 3-methoxybenzaldehyde (7.49 g, 55.0 mmol). The product was isolated by filtering the precipitate which occurred on acidification of the aqueous phase, yielding 12.2 g (94%) of the title compound: mp=179–181° C.; FDMS: M+=258; Anal. calcd. for $C_{15}H_{14}O_4$: C, 69.76, H, 5.46. Found: C, 70.00; H, 5.45.

(b) 1SR,5RS,6SR-Ethyl-2-oxo-3-((3-methoxy)benzylidenyl)bicyclo[3.1.0]hexane-6-carboxylate. The title compound was prepared by the method of Example 10(b) employing the product of step (a) (11.9 g, 46 mmol) $Et_3N$ (5.1 g, 50.7 mmol), DMAP (0.6 g, 4.6 mmol) and ethyl chloroformate (5.0 g, 46 mmol), yielding 13.1 g (99%) of the title compound: mp=102–104° C. FDMS: M+=286; Anal. calcd. for $C_{17}H_{18}O_4$: C, 71.30, H, 6.35. Found: C, 71.40; H, 6.35.

(c) 1SR,3RS,5RS,6SR-Ethyl-2-oxo-3-((3-methoxy)benzyl)bicyclo-[3.1.0]hexane-6-carboxylate. The title compound was prepared by the method of Example 1(c) employing the product of step (b) (8.0 g, 27.9 mmol) and Raney Ni (2.0 g). Evaporation of the solvent yielded 6.0 g (75%) of the title compound. FDMS: M+=288; Anal. calcd. for $C_{17}H_{20}O_4$: C, 70.81; H, 6.99. Found: C, 70.84; H, 7.20.

(d) 1SR,3SR,5RS,6SR-Ethyl-2-oxo-3-((3-methoxy)benzyl)bicyclo-[3.1.0]hexane-6-carboxylate. The title compound was prepared by the method of Example 3(c) employing the product of step (c) (6.0 g, 20.8 mmol) and Na (0.48 g, 21 g-atom). The crude product was purified by HPLC (5% EtOAc/hexane to 50% EtOAc/hexane) affording 3.1 g (50%) of the title compound. FDMS: M+=288. Anal. calcd. for $C_{17}H_{20}O_4$: C, 70.81; H, 6.99. Found: C, 71.09; H, 7.23.

(e) 1SR,2SR,3SR,5RS,6SR-Ethyl-2-aminoacetyl-2-cyano-3-((3-methoxy)benzyl)bicyclo[3.1.0]hexane-6-carboxylate and 1SR,2RS,3SR,5RS,6SR-Ethyl-2-aminoacetyl-2-cyano-3-((3-methoxy)benzyl)bicyclo[3.1.0]hexane-6-carboxylate. The title compounds were prepared by the method of Example 2(c) employing the product of step (d) (3.1 g, 10.8 mmol), $NH_4Cl$ (5.8 g, 108 mmol), KCN (7.0g, 108 mmol) and $Al_2O_3$ (50 g) in 100 mL acetonitrile. After 72 h, the solids were filtered and the filtrate evaporated to afford the amino nitrile which was acetylated with acetyl chloride (1.2 g, 15 mmol) and N,N-diisopropylethylamine (1.9 g, 15 mmol). The crude product was purified by HPLC (10% EtOAc/hexane to 80% EtOAc/hexane) yielding 1.5 g (38%) of 1SR,2SR,3SR,5RS,6SR-ethyl-2-aminoacetyl-2-cyano-3-((3-methoxy)benzyl)bicyclo [3.1.0]hexane-6-carboxylate (A) and 1.0 g (26%) of a mixture of (A) and 1SR,2RS,3SR,5RS,6SR-ethyl-2-aminoacetyl-2-cyano-3-((3-methoxy)benzyl)bicyclo[3.1.0]hexane-6-carboxylate (B). (A): mp=171–172° C. FDMS: M+=356. Anal. calcd. for $C_{20}H_{24}N_2O_4$: C, 67.40; H, 6.79; N, 7.86. Found: C, 67.66; H, 6.81; N, 7.82. (B): mp=52–58° C.; FDMS: M+=356. Anal. calcd. for $C_{20}H_{24}N_2O_4$: C, 67.40; H, 6.79; N, 7.86. Found: C, 67.12; H, 6.81; N, 7.67. nOe confirmation.

(f) The title compound was prepared by the method of Example 3(e) employing the 2SR product of step (e) (1.2 g, 3.4 mmol). After work up, 0.78 g (76%) of the title compound was obtained. mp=235–236° C.; FDMS: M+=305. Anal. calcd. for $C_{16}H_{19}NO_5.0.1\ H_2O$: C, 62.57; H, 6.30; N, 4.56. Found: C, 62.41; H, 6.16; N, 4.67.

EXAMPLE 14

1SR,2SR,3SR,5RS,6SR-2-Amino-3-((4-methoxy)benzyl)bicyclo[3.1.0]hexane-2,6-dicarboxylic acid (a) 1SR,5RS,6SR-2-Oxo-3-((4-methoxy)benzylidenyl)bicyclo[3.1.0]hexane-6-carboxylic acid. The title compound was prepared by the method of Example 9(a) employing the product of Preparation 2 (8.41 g, 50.0 mmol) and 4-methoxybenzaldehyde (7.49 g, 55.0 mmol). The product was isolated by filtering the precipitate obtained on acidification of the aqueous phase, yielding 12.5 g (97%) of the title compound: mp=192–194° C.; FDMS: M+=258; Anal. calcd. for $C_{15}H_{14}O_4$: C, 69.76, H, 5.46. Found: C, 70.78; H, 5.51. $^{13}$C-NMR (DMSO): 24.17, 27.25, 29.77, 34.57, 54.90, 114.02, 126.81, 130.05, 131.95, 133.03, 160.05, 171.07, 199.94.

(b) 1SR,5RS,6SR-Ethyl-2-oxo-3-((4-methoxy)benzylidenyl)bicyclo[3.1.0]hexane-6-carboxylate. The title compound was prepared by the method of Example 10(b) employing the product of step (a) (11.7 g, 45.3 mmol) $Et_3N$ (5.0 g, 49.4 mmol), DMAP (0.55 g, 4.5 mmol) and ethyl chloroformate (4.9 g, 45.3 mmol), yielding 11.6 g (89%) the title compound. mp=115–117° C. FDMS: M+=286; Anal. calcd. for $C_{17}H_{18}O_4$: C, 71.31; H, 6.34. Found: C, 71.40; H, 6.41.

(c) 1SR,3RS,5RS,6SR-Ethyl-2-oxo-3-((4-methoxy)benzyl)bicyclo-[3.1.0]hexane-6-carboxylate. The title compound was prepared by the method of Example 1(c) employing the product of step (b) (7.0 g, 24.5 mmol) and Raney Ni (2.0 g). Evaporation of the solvent and purification by HPLC (5% EtOAc/hexane to 50% EtOAc/hexane) yielded 6.5 g (92%) of the title compound. FDMS: M$^+$=288; Anal. calcd. for $C_{17}H_{20}O_4$: C, 70.81; H, 6.99. Found: C, 71.00; H, 7.02.

(d) 1SR,3SR,5RS,6SR-Ethyl-2-oxo-3-((4-methoxy)benzyl)bicyclo-[3.1.0]hexane-6-carboxylate. The title compound was prepared by the method of Example 3(c) employing the product of step (c) (6.3 g, 21.9 mmol) and Na (0.50 g, 21.9 g-atom) to afford 4.5 g (71%) of the title compound. FDMS: M$^+$=288. Anal. calcd. for $C_{17}H_{20}O_4$: C, 70.81; H, 6.99. Found: C, 71.04; H, 7.03.

(e) 1SR,2SR,3SR,5RS,6SR-Ethyl-2-aminoacetyl-2-cyano-3-((4-methoxy)benzyl)bicyclo[3.1.0]hexane-6-carboxylate and 1SR,2RS,3SR,5RS,6SR-Ethyl-2-aminoacetyl-2-cyano-3-((4-methoxy)benzyl)bicyclo[3.1.0]hexane-6-carboxylate. The title compounds were prepared by the method of Example 2(c) employing the product of step (d) (3.9 g, 13.9 mmol), NH$_4$Cl (7.4 g, 138 mmol), KCN (9.0 g, 138 mmol) and Al$_2$O$_3$ (50 g) in 100 mL acetonitrile. After 72 h, the solids were filtered and the filtrate evaporated to afford the amino nitrile which was acetylated with acetyl chloride (1.5 g, 19.0 mmol) and N,N-diisopropylethylamine (2.5 g, 19.0 mmol). The crude product was purified by HPLC (10% EtOAc/hexane to 80% EtOAc/hexane) yielding 1.55 g (31%) of 1SR,2SR,3SR,5RS,6SR-ethyl-2-aminoacetyl-2-cyano-3-((4-methoxy)benzyl)bicyclo [3.1.0] hexane-6-carboxylate (A) and 0.7 g (14%) of 1SR,2RS,3SR,5RS,6SR-ethyl-2-aminoacetyl-2-cyano-3-((4-methoxy)benzyl)bicyclo[3.1.0]hexane-6-carboxylate (B). (A): mp=201–203° C. FDMS: M$^+$=356. Anal. calcd. for $C_{20}H_{24}N_2O_4$: C, 67.40; H, 6.79; N, 7.86. Found: C, 67.24; H, 6.81; N, 7.95. (B): mp=58–67° C.; FDMS: M$^+$+1=357. Anal. calcd. for $C_{20}H_{24}N_2O_4$: C, 67.40; H, 6.79; N, 7.86. Found: C, 67.23; H, 6.64; N, 7.68.

(f) The title compound was prepared by the method of Example 3(e) employing the 2SR isomeric product of step (e) (0.5 g, 1.4 mmol). After workup, 0.373 g (87%) of the title compound was obtained. mp>250° C., FDMS: M$^+$=305. Anal. calcd. for $C_{16}H_{19}NO_5$: C, 62.94; H, 6.27; N, 4.59. Found: C, 63.03; H, 6.13; N, 4.32.

EXAMPLE 15

1SR,2SR,3SR,5RS,6SR-2-Amino-3-((4-fluoro)benzyl)bicyclo[3.1.0]hexane-2,6-dicarboxylic acid (a) 1SR,5RS,6SR-2-Oxo-3-((4-fluoro)benzylidenyl)bicyclo[3.1.0]hexane-6-carboxylic acid. The title compound was prepared by the method of Example 9(a) employing the product of Preparation 2 (4.2 g, 25 mmol) and 4-fluorobenzaldehyde (3.4 g, 27.5 mmol). The product was isolated by filtering the precipitate obtained on acidification of the aqueous phase, yielding 5.9 g (96%) of the title compound: mp=205–206° C. FDMS: M$^+$=246; Anal. calcd. for $C_{14}H_{11}FO_3$: C, 68.29, H, 4.50. Found: C, 68.48; H, 4.47.

(b) 1SR,5RS,6SR-Ethyl-2-oxo-3-((4-fluoro)benzylidenyl)bicyclo[3.1.0]hexane-6-carboxylate. The title compound was prepared by the method of Example 10(b) employing the product of step (a) (5.7 g, 23.0 mmol) Et$_3$N (2.6 g, 25.0 mmol), DMAP (0.30 g, 2.5 mmol) and ethyl chloroformate (2.5 g, 23.0 mmol), yielding 5.9 g (94%) of the title compound: mp=132–133° C., FDMS: M$^+$=274; Anal. calcd. for $C_{16}H_{15}FO_3$.0.1 hexane: C, 70.48; H, 5.84. Found: C, 70.74; H, 5.69.

(c) 1SR,3RS,5RS,6SR-Ethyl-2-oxo-3-((4-fluoro)benzyl)bicyclo[3.1.0]hexane-6-carboxylate. The title compound was prepared by the method of Example 1(c) employing the product of step (b) (4.3 g, 15.7 mmol) and Raney Ni (1.0 g). The product was purified by HPLC (5% EtOAc/hexane to 50% EtOAc/hexane) yielding 2.6 g (60%) of the title compound. FDMS: M$^+$=276; Anal. calcd. for $C_{16}H_{17}FO_3$: C, 69.55; H, 6.20. Found: C, 69.31; H, 6.24.

(d) 1SR,3SR,5RS,6SR-Ethyl-2-oxo-3-((4-fluoro)benzyl)bicyclo[3.1.0]hexane-6-carboxylate. The title compound was prepared by the method of Example 3(c) employing the product of step (c) (2.3 g, 8.3 mmol) and Na (0.20 g, 8.7 g-atom). Work up yielded 1.9 g (83%) of the title compound. FDMS: M$^+$=276; Anal. calcd. for $C_{16}H_{17}FO_3$: C, 69.55; H, 6.20. Found: C, 69.69; H, 6.23.

(e) 1SR,2SR,3SR,5RS,6SR-Ethyl-2-aminoacetyl-2-cyano-3-((4-fluoro)benzyl)bicyclo[3.1.0]hexane-6-carboxylate and 1SR,2RS,3SR,5RS,6SR-Ethyl-2-aminoacetyl-2-cyano-3-((4-fluoro)benzyl)bicyclo[3.1.0]hexane-6-carboxylate. The title compounds were prepared by the method of Example 2(c) employing the product of step (d) (1.8 g, 6.5 mmol), NH$_4$Cl (3.5 g, 65 mmol), KCN (4.2 g, 65 mmol) and Al$_2$O$_3$ (40 g). The intermediate amino nitrile was acetylated with acetyl chloride (0.6 g, 7.5 mmol) and N,N-diisopropylethylamine (1.0 g, 7.5 mmol) in CH$_2$Cl$_2$. The crude product was purified by HPLC (10% EtOAc/hexane to 80% EtOAc/hexane) yielding 0.6 g (27%) of 1SR,2SR,3SR,5RS,6SR-ethyl-2-aminoacetyl-2-cyano-3-((4-fluoro)benzyl)bicyclo[3.1.0]hexane-6-carboxylate (A) and 0.31 g (14%) of 1SR,2RS,3SR,5RS,6SR-ethyl-2-aminoacetyl-2-cyano-3-((4-fluoro)benzyl)bicyclo[3.1.0]hexane-6-carboxylate (B). (A): mp=256–257° C., FDMS: M$^+$=344; Anal. calcd. for $C_{19}H_{21}N_2O_3$: C, 66.27; H, 6.15; N, 8.13. Found: 66.03; H, 6.16; N, 7.88. (B): mp=71–73° C.; FDMS: M$^+$=344; Anal. calcd. for $C_{19}H_{21}N_2O_3$: C, 66.27; H, 6.15; N, 8.13. Found: C, 66.16; H, 6.38; N, 7.90.

(f) The title compound was prepared by the method of Example 3(e) employing the 2SR isomer product of step (e) (0.3 g, 0.9 mmol). After work up, 0.17 g (66%) of the title compound was obtained. mp=256–257° C., FDMS: M$^+$+1= 294. Anal. calcd. for $C_{15}H_{16}FNO_4$.0.33CH$_3$CO$_2$H: C, 60.07; H, 5.58; N, 4.47. Found: C, 59.96; H, 5.33; N, 4.11.

EXAMPLE 16

1SR,2SR,3SR,5RS,6SR-2-Amino-3-((4-methyl)benzyl)bicyclo[3.1.0]hexane-2,6-dicarboxylic acid (a) 1SR,5RS,6SR-Ethyl-2-oxo-3-((4-methyl)benzylidenyl)bicyclo[3.1.0]hexane-6-carboxylate. A solution consisting of the product of Preparation 2 (4.0 g, 23.8 mmol), 4-methylbenzaldehyde (3.0 g, 24.9 mmol) and pyrrolidine (1.2 mL) in EtOH (50 mL) was stirred at room temperature for 18 h. The reaction mixture was concentrated to dryness and the residue was purified by HPLC (10% EtOAc/hexane to 50% EtOAc/hexane) yielding 5.9 g (92%) of the title compound. mp=127–129° C. FDMS: M$^+$=270. Anal. calcd. for $C_{17}H_{18}O_3$: C, 75.53; H, 6.71. Found: C, 75.59; H, 6.75.

(b) 1SR,3RS,5RS,6SR-Ethyl-2-oxo-3-((4-methyl)benzyl)bicyclo[3.1.0]hexane-6-carboxylate Title compound was prepared according to the method of Example 1 (c) employing the product of step (a) (5.1 g, 18.9 mmol) and Raney Ni (1.3 g). Crude product was purified by HPLC (5% EtOAc/hexane to 50% EtOAc/hexane) yielding 4.0 g (78%) of the title compound. FDMS: M$^+$=272. Anal. calcd. for $C_{17}H_{20}O_3$: C, 74.48; H, 7.43. Found: C, 74.12; H, 7.36.

(c) 1SR,3SR,5RS,6SR-Ethyl-2-oxo-3-((4-methyl)benzyl)bicyclo[3.1.0]hexane-6-carboxylate. The title compound was prepared according to the method of Example 3 (c) employing the product of step (b) (3.5 g, 12.8 mmol) and Na (0.34 g, 14.7 g-atom). The crude product was purified by HPLC (10% EtOAc/hexane to 50% EtOAc/hexane) yielding 3.3 g (94%) of the title compound. mp=82–83° C. FDMS: $M^+$=272; Anal. calcd. for $C_{17}H_{20}O_3$: C, 74.97; H, 7.40. Found: C, 74.71; H, 7.46.

(d) 1SR,2SR,3SR,5RS,6SR-Ethyl-2-aminoacetyl-2-cyano-3-((4-methyl)benzyl)-bicyclo[3.1.0]hexane-6-carboxylate and 1SR,2RS,3SR,5RS,6SR-Ethyl-2-aminoacetyl-2-cyano-3-((4-methyl)benzyl)bicyclo[3.1.0]hexane-6-carboxylate. The title compounds were prepared according to the method of Example 2 (c) employing the product of step (c) (2.5 g, 9.2 mmol), KCN (6.0 g, 92 mmol), $NH_4Cl$ (4.9 g, 92 mmol) and $Al_2O_3$ (30 g). The intermediate amino nitrile was acylated using acetyl chloride (1.1 g, 13.5 mmol) and N,N-diisopropylethylamine (1.8 g, 13.5 mmol). The crude product was purified by HPLC (10% EtOAc/hexane to 80% EtOAc/hexane) yielding 1.35 g (43%) of 1SR,2SR,3SR,5RS,6SR-ethyl-2-aminoacetyl-2-cyano-3-((4-methyl)benzyl)-bicyclo[3.1.0]hexane-6-carboxylate (A) and 0.66 g (21%) of 1SR,2RS,3SR,5RS,6SR-ethyl-2-aminoacetyl-2-cyano-3-((4-methyl)benzyl)bicyclo[3.1.0]hexane-6-carboxylate (B). (A): mp=216–218° C. FDMS: $M^+$=340. Anal. calcd. for $C_{20}H_{24}N_2O_3$: C, 70.56; H, 7.11; N, 8.23. Found: C, 70.82; H, 7.04; N, 8.17. (B): mp=205–207° C. FDMS: $M^+$+1=341. Anal. calcd. for $C_{20}H_{24}N_2O_3$: C, 70.56; H, 7.11; N, 8.23. Found: C, 70.83; H, 7.17; N, 8.44.

(e) The title compound prepared by the method of Example 3 (e) employing the 2SR product of step (d) (1.05 g, 3.1 mmol). The crude product was dissolved in $H_2O$ at pH 10 and filtered. The product was precipitated at pH 3, filtered and washed with H2O, IPA and EtOAc, yielding 0.47 g (52%) of the title compound. mp=248–249° C., FDMS: $M^+$=289. Anal. calcd. for $C_{16}H_{19}NO_4$.0.33 $H_2O$: C, 65.07; H, 6.62; N, 4.84. Found: C, 64.85; H, 6.55; N, 4.76.

EXAMPLE 17

1SR,2SR,3SR,5RS,6SR-2-Amino-3-((3-fluoro)benzyl)bicyclo[3.1.0]hexane-2,6-dicarboxylic acid (a) 1SR,5RS,6SR-2-oxo-3-((3-fluoro)benzylidenyl)bicyclo[3.1.0]hexane-6-carboxylate. The title compound was prepared by the method of Example 9 (a) employing the product of Preparation 2 (4.2 g, 25 mmol) and 3-fluorobenzaldehyde (3.4 g, 27.5 mmol). The product was isolated by filtering the precipitate which occurred on acidification of the aqueous phase, yielding 6.1 (100%) of the title compound. mp=180–181° C.; FDMS: $M^+$=246; Anal. calcd. for $C_{14}H_{11}FO_3$.0.75 $H_2O$: C, 64.74, H, 4.85. Found: C, .67.39; H, 4.38

(b) 1SR,5RS,6SR-Ethyl-2-oxo-3-((3-fluoro)benzylidenyl)bicyclo[3.1.0]hexane-6-carboxylate. The title compound prepared according to the method of Example 10 (b) employing the product of step (a) (6.1 g, 24.8 mmol) $Et_3N$ (2.8 g, 27.2 mmol), DMAP (0.30 g, 2.5 mmol) and ethyl chloroformate (2.7 g, 24.8 mmol), yielding 5.4 g (90%) of the title compound. FDMS: $M^+$=274; Anal. calcd. for $C_{16}H_{15}FO_3$: C, 70.06; H, 5.51. Found: C, 69.83; H, 5.47.

(c) 1SR,3RS,5RS,6SR-Ethyl-2-oxo-3-((3-fluoro)benzyl)bicyclo[3.1.0]hexane-6-carboxylate. The title compound was prepared according to the method of Example 1 (c) employing the product of step (b) (4.9 g, 17.9 mmol) and Raney Ni (1.3 g). Product was purified by HPLC (5% EtOAc/hexane to 50% EtOAc/hexane) yielding 4.6 g (93%) of the title compound. FDMS: $M^+$+1=277; Anal. calcd. for $C_{16}H_{17}FO_3$: C, 69.55; H, 6.20. Found: C, 69.67; H, 6.18.

(d) 1SR,3SR,5RS,6SR-Ethyl-2-oxo-3-((3-fluoro)benzyl)bicyclo[3.1.0]hexane-6-carboxylate. The title compound was prepared by the method of Example 3 (c) employing the product of step (c) (4.4 g, 16 mmol) and Na (0.37 g, 16 g-atom). Work up yielded 4.2 g (96%) of the title compound. mp=67–69° C. FDMS: $M^+$=276; Anal. calcd. for $C_{16}H_{17}FO_3$: C, 69.55; H, 6.20. Found: C, 69.71; H, 6.11.

(e) 1SR,2SR,3SR,5RS,6SR-Ethyl-2-aminoacetyl-2-cyano-3-((3-fluoro)benzyl)-bicyclo[3.1.0]hexane-6-carboxylate and 1SR,2RS,3SR,5RS,6SR-Ethyl-2-aminoacetyl-2-cyano-3-((3-fluoro)benzyl)bicyclo[3.1.0]hexane-6-carboxylate. The title compounds were prepared according to the method of Example 2 (c) employing the product of step (d) (3.7 g, 13.5 mmol), $NH_4Cl$ (7.2 g, 135 mmol), KCN (8.8 g, 135 mmol) and $Al_2O_3$ (34 g). The intermediate amino nitrile mixture was acetylated with acetyl chloride (1.67 g, 21.3 mmol) and N,N-diisopropylethylamine (2.75 g, 21.3 mmol) in $CH_2Cl_2$. The crude product was purified by HPLC (10% EtOAc/hexane to 80% EtOAc/hexane) yielding 1.8 g (37%) of 1SR,2SR,3SR,5RS,6SR-ethyl-2-aminoacetyl-2-cyano-3-((3-fluoro)benzyl)bicyclo[3.1.0]hexane-6-carboxylate (A) and 1.2 g (24%) of 1SR,2RS,3SR,5RS,6SR-ethyl-2-aminoacetyl-2-cyano-3-((3-fluoro)benzyl)bicyclo[3.1.0]hexane-6-carboxylate (B). (A): mp=202–204° C., FDMS: $M^+$=344; Anal. calcd. for $C_{19}H_{21}FN_2O_3$: C, 66.27; H, 6.15; N, 8.13. Found: C, 66.15; H, 6.15; N, 8.29.

(f) The title compound was prepared according to the method of Example 3 (e) employing the 2SR product of step (e) (1.0 g, 2.9 mmol). After work up, 0.67 g (79%) of the title compound was obtained. mp=247–248° C. FDMS: $M^+$+1= 294. Anal. calcd. for $C_{15}H_{16}FNO_4$: C, 61.43; H, 5.50; N, 4.78. Found: C, 61.13; H, 5.54; N, 4.70.

EXAMPLE 18

1SR,2SR,3SR,5RS,6SR-2-Amino-3-((3,5-difluoro)benzyl)bicyclo[3.1.0]hexane-2,6-dicarboxylic acid (a) 1SR,5RS,6SR-Ethyl-2-oxo-3-((3,5-difluoro)benzylidenyl)bicyclo[3.1.0]-hexane-6-carboxylate. The title compound was prepared by the method of Example 16 (a) employing the product of Preparation 2 (6.3 g, 37.4 mmol), 3,5-difluorobenzaldehyde (5.3 g, 37.3 mmol) and pyrrolidine (1.1 mL) in EtOH (150 mL). The precipitate which formed was filtered, washed with EtOH and dried to yield 8.8 g (81%) of the title compound. mp=127–128° C.; FDMS: $M^+$=292; Anal. calcd. for $C_{16}H_{14}F_2O_3$: C, 65.75; H, 4.83. Found: C, 66.00; H, 4.82.

(b) 1SR,3RS,5RS,6SR-Ethyl-2-oxo-3-((3,5-difluoro)benzyl)bicyclo[3.1.0]-hexane-6-carboxylate. The title compound was prepared according to the method of Example 1 (c) employing the product of step (a) (6.5 g, 22.3 mmol) and Raney Ni (1.6 g). Crude product was purified by HPLC (5% EtOAc/hexane to 50% EtOAc/hexane) yielding 5.9 g (90%) of the title compound. FDMS: $M^+$=294. Anal. calcd. for $C_{16}H_{16}F_2O_3$: C, 65.30; H, 5.48. Found: C, 65.32; H, 5.40.

(c) 1SR,3SR,5RS,6SR-Ethyl-2-oxo-3-((3,5-difluoro)benzyl)bicyclo[3.1.0]hexane-6-carboxylate. The title compound was prepared according to the method of Example 3 (c) employing the product of step (b) (5.4 g, 18.4 mmol) and Na (0.42 g, 18.4 g-atom), yielding after workup 4.9 g (91%) of the title compound. mp=95–97° C.; FDMS: $M^+$=294; Anal. calcd. for $C_{16}H_{16}F_2O_3$: C, 65.30; H, 5.48. Found: C, 65.56; H, 5.38.

(d) 1SR,2SR,3SR,5RS,6SR-Ethyl-2-aminoacetyl-2-cyano-3-((3,5-difluoro)benzyl)bicyclo[3.1.0]hexane-6- carboxylate and 1SR,2RS,3SR,5RS,6SR-Ethyl-2-aminoacetyl-2-cyano-3-((3,5-difluoro)benzyl)bicyclo[3.1.0]hexane-6-carboxylate. The title compounds were prepared according to the method of Example 2 (c) employing the product of step (c) (4.3 g, 14.6 mmol), KCN (9.5 g, 146 mmol), $NH_4Cl$ (7.8 g, 146 mmol) and $Al_2O_3$ (37 g). The intermediate amino nitriles were acylated using acetyl chloride (1.84 g, 23.4 mmol) and N,N-diisopropylethylamine (3.0 g, 23.4 mmol). The crude products were purified by HPLC (10% EtOAc/hexane to 80% EtOAc/hexane) yielding 2.2 g (40%) of 1SR,2SR,3SR,5RS,6SR-ethyl-2-aminoacetyl-2-cyano-3-((3,5-difluoro)benzyl)bicyclo[3.1.0]hexane-6-carboxylate (A) and 1.2 g (22%) of 1SR,2RS,3SR,5RS,6SR-ethyl-2-aminoacetyl-2-cyano-3-((3,5-difluoro)benzyl)bicyclo[3.1.0]hexane-6-carboxylate (B). (A): mp=196–198° C. FDMS: $M^+$=362. Anal. calcd. for $C_{19}H_{20}F_2N_2O_3$: C, 62.98; H, 5.56; N, 7.73. Found: C, 62.72; H, 5.50; N, 7.74.

(e) The title compound was prepared by the method of Example 3 (e) employing the 2SR product of step (d) (1.7 g, 4.7 mmol) and 2N HCl (100 mL). After work up 1.1 g (78%) of the title compound was obtained. mp>250° C., FDMS: $M^+$+1=312. Anal. calcd. for $C_{15}H_{15}F_2NO_4$: C, 57.88; H, 4.86; N, 4.50. Found: C, 57.93; H, 4.80; N, 4.21.

EXAMPLE 19

1SR,2SR,3SR,5RS,6SR-2-Amino-3-((3-phenoxy)benzyl)bicyclo[3.1.0]hexane-2,6-dicarboxylic acid (a) 1SR,5RS,6SR-Ethyl-2-oxo-3-((3-phenoxy)benzylidenyl)-bicyclo[3.1.0]hexane-6-carboxylate. The title compound was prepared according to the method of Example 16(a) employing the product of Preparation 2 (5.0 g, 29.7 mmol), 3-phenoxybenzaldehyde (5.0 g, 25.2 mmol) and pyrrolidine (1 mL) in EtOH (150 mL). The precipitate which formed was filtered, washed with EtOH and dried to yield 8.05 g (92%) of the title compound. mp=125–126° C.; FDMS: $M^+$=348; Anal. calcd. for $C_{22}H_{20}O_4$: C, 75.84; H, 5.79. Found: 76.07; H, 5.71.

(b) 1SR,3RS,5RS,6SR-Ethyl-2-oxo-3-((3-phenoxy)benzyl)bicyclo[3.1.0]hexane-6-carboxylate. The title compound was prepared according to the method of Example 1 (c) employing the product of step (a) (7.5 g, 21.8 mmol) and Raney Ni (1.9 g). Crude product was purified by HPLC (10% EtOAc/hexane to 50% EtOAc/hexane) yielding 7.5 g (99%) of the title compound. FDMS: $M^+$=350. Anal. calcd. for $C_{22}H_{22}O_4$·0.3 $H_2O$: C, 74.26; H, 6.40. Found: C, 73.90; H, 6.13.

(c) 1SR,3SR,5RS,6SR-Ethyl-2-oxo-3-((3-phenoxy)benzyl)bicyclo[3.1.0]hexane-6-carboxylate. The title compound was prepared according to the method of Example 3 (c) employing the product of step (b) (6.5 g, 18.5 mmol) and Na (0.43 g, 18.5 g-atom), yielding after workup 5.5 g (85%) of the title compound. FDMS: $M^+$=350; Anal. calcd. for $C_{22}H_{22}O_4$: C, 75.41; H, 6.34. Found: C, 75.26; H, 6.40.

(d) 1SR,2SR,3SR,5RS,6SR-Ethyl-2-aminoacetyl-2-cyano-3-((3-phenoxy)benzyl)-bicyclo[3.1.0]hexane-6-carboxylate and 1SR,2RS,3SR,5RS,6SR-Ethyl-2-aminoacetyl-2-cyano-3-((3-phenoxy)benzyl)bicyclo[3.1.0]hexane-6-carboxylate. The title compounds were prepared by the method of Example 2 (c) employing the product of step (c) (5.0 g, 14.3 mmol), KCN (9.3 g, 143 mmol), $NH_4Cl$ (7.6 g, 143 mmol) and $Al_2O_3$ (50 g). The intermediate amino nitriles were acylated using acetyl chloride (1.5 g, 19.1 mmol) and N,N-diisopropylethylamine (2.5 g, 19.1 mmol). The crude products were purified by HPLC (10% EtOAc/hexane to 80% EtOAc/hexane) yielding 2.4 g (45%) 1SR,2SR,3SR,5RS,6SR-ethyl-2-aminoacetyl-2-cyano-3-((3-phenoxy)benzyl)-bicyclo[3.1.0]hexane-6-carboxylate (A) and 1.5 g (28%) 1SR,2RS,3SR,5RS,6SR-ethyl-2-aminoacetyl-2-cyano-3-((3-phenoxy)benzyl)bicyclo[3.1.0]hexane-6-carboxylate (B). (A) mp=158–160° C.; FDMS: $M^+$=418; Anal. calcd. for $C_{25}H_{25}N_2O_4$·0.5 $H_2O$: C, 70.24; H, 6.37.; N, 6.55; Found: C, 70.16; H, 6.52; N, 6.25. (B) FDMS: $M^+$=418; Anal. calcd. for $C_{25}H_{25}N_2O_4$·0.6 $H_2O$: C, 69.95; H, 6.39.; N, 6.53; Found: C, 69.84 H, 6.65; N, 6.26.

(e) The title compound was prepared by the method of Example 3 (e) employing the 2SR product of step (d) (2.1 g, 5 mmol) and 2N HCl (100 mL). After work up and precipitation at pH 5, 0.98 g (53%) of the title compound was obtained. mp=241–242° C., FDMS: $M^+$-$CO_2H$=322. Anal. calcd. for $C_{21}H_{21}NO_5$: C, 68.65; H, 5.76; N, 3.81. Found: C, 68.91; H, 5.78; N, 3.65.

EXAMPLE 20

1SR,2SR,3SR,5RS,6SR-2-Amino-3-((3-trifluoromethoxy)benzyl)bicyclo[3.1.0]hexane-2,6-dicarboxylic acid (a) 1SR,5RS,6SR-Ethyl-2-oxo-3-((3-trifluoromethoxy)benzylidenyl)-bicyclo[3.1.0]hexane-6-carboxylate. The title compound was prepared by the method of Example 16(a) employing the product of Preparation 2 (4.1 g, 24.5 mmol), 3-trifluoromethoxybenzaldehyde (4.9 g, 24.5 mmol) and pyrrolidine (1 mL) in EtOH (150 mL). The precipitate which formed was filtered, washed with EtOH and dried to yield 6.55 g (79%) of the title compound. mp=96–97° C.; FDMS: $M^+$+1=341; Anal. calcd. for $C_{17}H_{15}F_3O_4$: C, 60.00; H, 4.44. Found: C, 60.27; H, 4.43.

(b) 1SR,3RS,5RS,6SR-Ethyl-2-oxo-3-((3-trifluoromethoxy)-benzyl)-bicyclo[3.1.0]hexane-6-carboxylate. The title compound was prepared according to the method of Example 1 (c) employing the product of step (a) (6.2 g, 18.2 mmol) and Raney Ni (1.5 g). Crude product was purified by HPLC (10% EtOAc/hexane to 50% EtOAc/hexane) yielding 5.5 g (88%) of the title compound. FDMS: $M^+$=342. Anal. calcd. for $C_{17}H_{17}F_3O_4$: C, 59.65; H, 5.01. Found: C, 59.47; H, 5.02.

(c) 1SR,3SR,5RS,6SR-Ethyl-2-oxo-3-((3-trifluoromethoxy)benzyl)-bicyclo[3.1.0]hexane-6-carboxylate. The title compound was prepared according to the method of Example 3 (c) employing the product of step (b) (4.9 g, 17.9 mmol) and Na (0.41 g, 17.9 g-atom), yielding after workup 4.6 g (94%) of the title compound. mp=65–66° C.; FDMS: $M^+$=342; Anal. calcd. for $C_{17}H_{17}F_3O_4$: C, 59.65; H, 5.01. Found: C, 59.29; H, 4.94.

(d) 1SR,2SR,3SR,5RS,6SR-Ethyl-2-aminoacetyl-2-cyano-3-((3-trifluoromethoxy)benzyl)bicyclo[3.1.0]hexane-6-carboxylate and 1SR,2RS,3SR,5RS,6SR-Ethyl-2-aminoacetyl-2-cyano-3-((3-trifluoromethoxy)benzyl)bicyclo[3.1.0]hexane-6-carboxylate. The title compounds were prepared by the method of Example 2 (c) employing the product of step (c) (4.2 g, 15.3 mmol), KCN (9.4 g, 144 mmol), $NH_4Cl$ (7.7 g, 144 mmol) and $Al_2O_3$ (50 g). The intermediate amino nitriles were acylated using acetyl chloride (1.6 g, 20.4 mmol) and N,N-diisopropylethylamine (2.6 g, 20.4 mmol). The crude products were purified by HPLC (10% EtOAc/hexane to 80% EtOAc/hexane) yielding 2.5 g (45%) of 1SR,2SR,3SR,5RS,6SR-Ethyl-2-aminoacetyl-2-cyano-3-((3-trifluoromethoxy)benzyl)bicyclo[3.1.0]-hexane-6-carboxylate (A) and 1.5 g (27%) of 1SR,2RS,3SR,5RS,6SR-ethyl-2-aminoacetyl-2-cyano-3-((3- trifluoromethoxy)benzyl)bicyclo[3.1.0]hexane-6-carboxylate (B). (A): mp=194–197° C. FDMS: M+=410. Anal. calcd. for $C_{20}H_{21}F_3N_2O_4$: C, 58.53; H, 5.16; N, 6.83. Found: C, 58.43; H, 5.24; N, 6.71.

(e) The title compound was prepared by the method of Example 3 (e) employing the 2SR product of step (d) (1.5 g, 1.86 mmol) and 2N HCl (100 mL). After work up and precipitation at pH 5, 0.34 g (26%) of the title compound was obtained. mp>250° C., FDMS: M++1=360. Anal. calcd. for $C_{16}H_{16}F_3NO_5$: C, 53.49; H, 4.49; N, 3.90. Found: C, 53.44; H, 4.40; N, 3.86.

EXAMPLE 21

1SR,2SR,3SR,5RS,6SR-2-Amino-3-((3-fluoro-4-methoxy)benzyl)bicyclo[3.1.0]hexane-2,6-dicarboxylic acid (a) 1SR,5RS,6SR-Ethyl-2-oxo-3-((3-fluoro-4-methoxy)benzylidenyl)-bicyclo[3.1.0]hexane-6-carboxylate. The title compound was prepared by the method of Example 16(a) employing the product of Preparation 2 (5.5 g, 32.4 mmol), 3-fluoro-4-methoxybenzaldehyde (5.0 g, 32.4 mmol) and pyrrolidine (1 mL) in EtOH (150 mL). The precipitate which formed was filtered, washed with EtOH (containing toluene) and dried to yield 7.75 g (79%) of the title compound. FDMS: M+=304; Anal. calcd. for $C_{17}H_{17}FO_4 \cdot 0.1$ toluene: C, 67.81; H, 5.72. Found: C, 68.01; H, 5.71.

(b) 1SR,3RS,5RS,6SR-Ethyl-2-oxo-3-((3-fluoro-4-methoxy)benzyl)-bicyclo[3.1.0]hexane-6-carboxylate. The title compound was prepared according to the method of Example 1 (c) employing the product of step (a) (7.0 g, 23.0 mmol) and Raney Ni (1.75 g). Crude product was purified by HPLC (5% EtOAc/hexane to 50% EtOAc/hexane) yielding 5.7 g (81%) of the title compound. FDMS: M+=306. Anal. calcd. for $C_{17}H_{19}FO_4$: C, 66.65; H, 6.25. Found: C, 66.87; H, 6.16.

(c) 1SR,3SR,5RS,6SR-Ethyl-2-oxo-3-((3-fluoro-4-methoxy)benzyl)-bicyclo[3.1.0]hexane-6-carboxylate. The title compound was prepared according to the method of Example 3 (c) employing the product of step (b) (5.3 g, 17.3 mmol) and Na (0.40 g, 17.3 g-atom), yielding after workup 4.9 g (92%) of the title compound. FDMS: M+=306; Anal. calcd. for $C_{17}H_{19}FO_4 \cdot 0.1H_2O$: C, 62.27; H, 6.17. Found: C, 66.03; H, 6.09.

(d) 1SR,2SR,3SR,5RS,6SR-Ethyl-2-oxo-3-((3-fluoro-4-methoxy)benzyl)-bicyclo[3.1.0]hexane-6-carboxylate and 1SR,2RS,3RS,5RS,6SR-Ethyl-2-oxo-3-((3-fluoro-4-methoxy)benzyl)-bicyclo[3.1.0]hexane-6-carboxylate. The title compounds were prepared by the method of Example 2 (c) employing the product of step (c) (4.5 g, 14.6 mmol), KCN (10 g, 154 mmol), NH$_4$Cl (8.5 g, 158 mmol) and Al$_2$O$_3$ (40 g). The intermediate amino nitriles were acylated using acetyl chloride (1.8 g, 22.6 mmol) and N,N-diisopropylethylamine (2.9 g, 22.6 mmol). The crude products were purified by HPLC (10% EtOAc/hexane to 80% EtOAc/hexane) yielding 1.3 g (23%) of 1SR,2SR,3SR,5RS,6SR-ethyl-2-oxo-3-((3-fluoro-4-methoxy)benzyl)-bicyclo[3.1.0]hexane-6-carboxylate (A) and 1.7 g (31%) of a mixture of (A) and 1SR,2RS,3RS,5RS,6SR-ethyl-2-oxo-3-((3-fluoro-4-methoxy)benzyl)bicyclo[3.1.0]hexane-6-carboxylate (B). (A) mp=194–196° C. FDMS: M+=374. Anal. calcd. for $C_{20}H_{23}FN_2O_4$: C, 64.16; H, 6.19; N, 7.48. Found: C, 64.22; H, 6.03; N, 7.48.

(e) The title compound was prepared by the method of Example 3 (e) employing the 2SR product of step (d) (0.7 g, 1.86 mmol) and 2N HCl (75 mL). After work up and precipitation at pH 5, yielded 0.5 g (86%) of the title compound was obtained. mp>250° C., FDMS: M+=323. Anal. calcd. for $C_{16}H_{18}FNO_5$: C, 59.44; H, 5.61; N, 4.33. Found: C, 59.42; H, 5.58; N, 4.44.

EXAMPLE 22

1SR,2SR,3SR,5RS,6SR-2-Amino-3-((3-chloro-4-fluoro)benzyl)bicyclo[3.1.0]hexane-2,6-dicarboxylic acid (a) 1SR,5RS,6SR-Ethyl-2-oxo-3-((3-chloro-4-fluoro)benzylidenyl)-bicyclo[3.1.0]hexane-6-carboxylate. The title compound was prepared according to the method of Example 16(a) employing the product of Preparation 2 (5.0 g, 30.3 mmol), 3-chloro-4-fluorobenzaldehyde (4.8 g, 30.3 mmol) and pyrrolidine (1.1 mL) in EtOH (150 mL). The precipitate which formed was filtered, washed with EtOH and dried to yield 7.2 g (77%) of the title compound. mp=123–124° C.; FDMS: M+=308; Anal. calcd. for $C_{16}H_{14}ClFO_3$: C, 62.25; H, 4.57. Found: C, 62.50; H, 4.49.

(b) 1SR,3SR,5RS,6SR-Ethyl-2-oxo-3-((3-chloro-4-fluoro)benzyl)-bicyclo[3.1.0]hexane-6-carboxylate. The title compound was prepared sequentially according to the method of Example 1 (c) and the method of Example 3 (c) employing in the first method the product of step (a) (6.7 g, 21.7 mmol) and Raney Ni (1.7 g). The crude product from this step was purified by HPLC (5% EtOAc/hexane to 50% EtOAc/hexane) yielding 5.8 g (86%) of the 3RS diastereomer which was subjected to the conditions of Example 3 (c) employing Na (0.44 g, 19.3 g-atom) in EtOH to afford 5.5 g (95%) of 1SR,3SR,5RS,6SR-Ethyl-2-oxo-3-((3-chloro-4-fluoro)benzyl)bicyclo[3.1.0]hexane-6-carboxylate. mp=86–89° C.; FDMS: M+=310; Anal. calcd. for $C_{16}H_{16}ClFO_3$: C, 61.84; H, 5.19. Found: C, 62.07; H, 5.16.

(c) 1SR,2SR,3SR,5RS,6SR-Ethyl-2-oxo-3-((3-chloro-4-fluoro)benzyl)-bicyclo[3.1.0]hexane-6-carboxylate. The title compound was prepared by the method of Example 2 (c) employing the product of step (b) (5.2 g, 16.7 mmol), KCN (10.9 g, 167 mmol), NH$_4$Cl (9.0 g, 167 mmol) and Al$_2$O$_3$ (53 g). The intermediate amino nitriles were acylated using acetyl chloride (1.7 g, 22.2 mmol) and N,N-diisopropylethylamine (2.8 g, 22.2 mmol). The crude products were purified by crystalization from CH$_2$Cl$_2$ which yieled 1.1 g (17%) of the title compound. mp=232–234° C. FDMS: M+=378. Anal. calcd. for $C_{19}H_{20}FClN_2O_3$: C, 60.24; H, 5.32; N, 7.39. Found: C, 60.26; H, 5.30; N, 7.44.

(d) The title compound was prepared by the method of Example 3 (e) employing the product of step (c) (0.75 g, 2 mmol) and 2N HCl (100 mL). After work up, 0.56 g (86%) of the title compound was obtained. mp=256–257° C., FDMS: M++1=328. Anal. calcd. for $C_{15}H_{15}FClNO_4 \cdot 0.2$ $C_4H_8O_2$: C, 54.95; H, 4.84; N, 4.06. Found: C, 54.61; H, 4.68; N, 3.69.

EXAMPLE 23

1SR,2SR,3SR,5RS,6SR-2-Amino-3-((3,4-difluoro)benzyl)bicyclo[3.1.0]hexane-2,6-dicarboxylic acid (a) 1SR,5RS,6SR-Ethyl-2-oxo-3-((3,4-difluoro)benzylidenyl)bicyclo[3.1.0]hexane-6-carboxylate. The title compound was prepared by the method of Example 16(a) employing the product of Preparation 2 (5.9 g, 35.2 mmol), 3,4-difluorobenzaldehyde (5.0 g, 35.2 mmol) and pyrrolidine (1 mL) in EtOH (150 mL). The precipitate which formed was filtered, washed with EtOH (containing toluene) and dried to yield 7.46 g (73%) of the title compound.

mp=120–121° C.; FDMS: M⁺+1=293; Anal. calcd. for $C_{16}H_{14}F_2O_3$·0.3 toluene: C, 67.95; H, 5.17. Found: C, 68.20; H, 5.09.

(b) 1SR,3RS,5RS,6SR-Ethyl-2-oxo-3-((3,4-difluoro) benzyl)bicyclo[3.1.0]hexane-6-carboxylate. The title compound was prepared by the method of Example 1 (c) employing the product of step (a) (6.4 g, 21.9 mmol) and Raney Ni (1.4 g). Crude product was purified by HPLC (5% EtOAc/hexane to 50% EtOAc/hexane) yielding 5.9 g (91%) of the title compound. FDMS: M⁺=294. Anal. calcd. for $C_{16}H_{16}F_2O_3$·0.1H₂O: C, 64.90; H, 5.52. Found: C, 64.75; H, 5.37.

(c) 1SR,3SR,5RS,6SR-Ethyl-2-oxo-3-((3,4-difluoro) benzyl)bicyclo[3.1.0]hexane-6-carboxylate. The title compound was prepared according to the melthod of Example 3 (c) employing the product of step (b) (5.5 g, 18.7 mmol) and Na (0.42 g, 18.7 g-atom), yielding after workup 5.0 g (91%) of the title compound. mp=91–93° C.; FDMS: M⁺=294.

(d) 1SR,2SR,3SR,5RS,6SR-Ethyl-2-aminoacetyl-2-cyano-3-((3,4-difluoro)benzyl)bicyclo[3.1.0]hexane-6-carboxylate and 1SR,2RS,3SR,5RS,6SR-Ethyl-2-aminoacetyl-2-cyano-3-((3,4-difluoro)benzyl)bicyclo [3.1.0]hexane-6-carboxylate. The title compounds were prepared by the method of Example 2 (c) employing the product of step (c) (4.5 g, 15.3 mmol), KCN (10 g, 153 mmol), NH₄Cl (8.2 g, 153 mmol) and Al₂O₃ (35 g). The intermediate amino nitriles were acylated using acetyl chloride (1.87 g, 23.9 mmol) and N,N-diisopropylethylamine (3.1 g, 23.9 mmol). Crystallization from CH₂Cl₂ yielded 1.3 g (23%) of 1SR,2SR,3SR,5RS,6SR-ethyl-2-aminoacetyl-2-cyano-3-((3,4-difluoro)benzyl)bicyclo[3.1.0]hexane-6-carboxylate (A). The remainder of the crude products were purified by HPLC (10% EtOAc/hexane to 80% EtOAc/hexane) yielding an additional 0.57 g (12%, combined yield=35%) of (A) and 1.2 g (21%) of a mixture of (A) and 1SR,2RS,3SR,5RS,6SR-ethyl-2-aminoacetyl-2-cyano-3-((3,4-difluoro)benzyl)bicyclo[3.1.0]hexane-6-carboxylate (B). (A): mp=238–239° C. FDMS: M⁺=362. Anal. calcd. for $C_{19}H_{20}F_2N_2O_3$: C, 62.98; H, 5.56; N, 7.73. Found: C, 62.75; H, 5.65; N, 7.81.

(e) The title compound was prepared by the method of Example 3 (e) employing the 2SR product of step (d) (0.37 g, 01 mmol) and 2N HCl (100 mL). After work up, 0.15 g (47%) of the title compound was obtained. mp=248–249° C., FDMS: M⁺+1=312. Anal. calcd. for $C_{15}H_{15}F_2NO_4$: C, 57.22; H, 4.93; N, 4.45. Found: C, 57.00; H, 4.85; N, 4.43.

EXAMPLE 24

1SR,2SR,3SR,5RS,6SR-2-Amino-3-((4-chloro) benzyl)bicyclo[3.1.0]hexane-2,6-dicarboxylic acid (a) 1SR,5RS,6SR-2-Oxo-3-((4-chloro)benzylidenyl) bicyclo[3.1.0]hexane-6-carboxylate. The title compound was prepared by the method of Example 9 (a) employing the product of Preparation 2 (8.41 g, 50.0 mmol) and 4-chlorobenzaldehyde (8.0 g, 57 mmol). The product was isolated by filtering the precipitate which occurred on acidification of the aqueous phase, yielding 13.1 g, 99%) of the title compound. mp=246–248° C.; FDMS: M⁺=262; Anal. calcd. for $C_{14}H_{11}ClO_3$: C, 64.01, H, 4.22. Found: C, 63.76; H, 4.19. ¹³C-NMR (DMSO): 25.54, 28.84, 31.02, 35.82, 129.79, 132.93, 134.44, 135.00, 135.13, 172.30, 201.38.

(b) 1SR,5RS,6SR-Ethyl-2-oxo-3-((4-chloro) benzylidenyl)bicyclo[3.1.0]hexane-6-carboxylate. The title compound was prepared according to the method of Example 10 (b) employing compound the product of step (a) (12.8 g, 48.7 mmol), Et₃N (5.42 g, 53.6 mmol), DMAP (0.59 g, 4.87 mmol) and ethyl chloroformate (8.62 g, 53.6 mmol), yielding 13.5 g (95%) the title compound. mp=151–152° C.; FDMS: M⁺=290; Anal. calcd. for $C_{16}H_{15}ClO_3$: C, 66.10, H, 5.20. Found: C, 65.82; H, 5.31.

(c) 1SR,3RS,5RS,6SR-Ethyl-2-oxo-3-((4-chloro)benzyl) bicyclo[3.1.0]hexane-6-carboxylate. The title compound was prepared by the method of Example 1 (c) employing the product of step (b) (7.0 g, 24.1 mmol) and Raney Ni (3.5 g). Crude product was purified by HPLC (5% EtOAc/hexane to 50% EtOAc/hexane) yielding 5.4 g (77%) of the title compound. FDMS: M⁺=292. Anal. calcd. for $C_{16}H_{17}ClO_3$: C, 65.64; H, 5.85; Cl, 12.11. Found: C, 65.87; H, 5.74; N, 12.16.

(d) 1SR,3SR,5RS,6SR-Ethyl-2-oxo-3-((4-chloro)benzyl) bicyclo[3.1.0]hexane-6-carboxylate. The title compound was prepared according to the method of Example 3 (c) employing the product of step (c) (2.4 g, 8.2 mmol) and Na (0.20 g, 8.7 g-atom). Work up yielded 2.1 g (88%) of the title compound. FDMS: M⁺=292. Anal. calcd. for $C_{16}H_{17}ClO_3$: C, 65.64; H, 5.85; Cl, 12.11. Found: C, 65.40; H, 5.95; N, 12.31.

(e) 1SR,2SR,3SR,5RS,6SR-Ethyl-2-aminoacetyl-2-cyano-3-((4-chloro)benzyl)bicyclo[3.1.0]hexane-6-carboxylate and 1SR,2RS,3SR,5RS,6SR-Ethyl-2-aminoacetyl-2-cyano-3-((4-chloro)benzyl)bicyclo[3.1.0] hexane-6-carboxylate. The title compounds were prepared according to the method of Example 2 (c) employing the product of step (d) (2.0 g, 6.8 mmol), NH₄Cl (3.7 g, 68 mmol), KCN (4.4 g, 68 mmol) and Al₂O₃ (40 g). The intermediate amino nitriles were acetylated with acetyl chloride (0.63 g, 8.0 mmol) and N,N-diisopropylethylamine (1.0 g, 8.0 mmol) in CH₂Cl₂. Crystalization from CH₂Cl₂ yielded 0.52 g (21%) of 1SR,2SR,3SR,5RS,6SR-ethyl-2-aminoacetyl-2-cyano-3-((4-chloro)benzyl)bicyclo[3.1.0] hexane-6-carboxylate (A). The remainder of the crude products were purified by HPLC (10% EtOAc/hexane to 80% EtOAc/hexane) yielding 0.32 g (13%) of (A) and 0.50 g (20%) of 1SR,2RS,3SR,5RS,6SR-ethyl-2-aminoacetyl-2-cyano-3-((4-chloro)benzyl)bicyclo[3.1.0]hexane-6-carboxylate (B). (A): mp=257–260° C.; FDMS: M⁺=360; Anal. calcd. for $C_{19}H_{21}ClN_2O_3$: C, 63.24; H, 5.87; N, 7.76. Found: C, 63.28; H, 5.91; N, 7.76. (B): mp=85–91° C.; FDMS: M⁺=360; Anal. calcd. for $C_{19}H_{21}ClN_2O_3$: C, 63.24; H, 5.87; N, 7.76. Found: C, 62.96; H, 5.83; N, 7.60.

(f) The title compound was prepared by the method of Example 3 (e) employing the 2SR product of step (e) (0.28 g, 0.78 mmol). After work up, 0.20 g (83%) of the title compound was obtained. mp=259–261° C., FDMS: M⁺=309. Anal. calcd. for $C_{15}H_{16}ClNO_4$: C, 58.16; H, 5.21; N, 4.52. Found: C, 57.94; H, 5.19; N, 4.63.

EXAMPLE 25

1SR,2SR,3SR,5RS,6SR-2-Amino-3-((2,3,4-trifluoro)benzyl)bicyclo[3.1.0]hexane-2,6-dicarboxylic acid (a) 1SR,5RS,6SR-Ethyl-2-oxo-3-((2,3,4-trifluoro) benzylidenyl)-bicyclo[3.1.0]hexane-6-carboxylate. The title compound was prepared according to the method of Example 16(a) employing the product of Preparation 2 (4.7 g, 27.9 mmol), 2,3,4-trifluorobenzaldehyde (4.7 g, 29.4 mmol) and pyrrolidine (1 mL) in EtOH (100 mL). The precipitate which formed was filtered, washed with hexane and dried to yield 5.6 g (64%) of the title compound. mp=130–131° C.; FDMS: M⁺=310; Anal. calcd. for $C_{16}H_{13}F_3O_3$: C, 61.93; H, 4.22. Found: C, 62.14; H, 4.18.

(b) 1SR,3SR,5RS,6SR-Ethyl-2-oxo-3-((2,3,4-trifluoro)benzyl)bicyclo[3.1.0]hexane-6-carboxylate. The title compound was prepared sequentially according to the method of Example 1 (c) and the method of Example 3 (c) employing in the first method the product of step (a) (5.2, 16.7 mmol) and Raney Ni (1.3 g). The crude product from this step was purified by HPLC (10% EtOAc/hexanes to 25% EtoAc/hexanes) yielding 4.8 g (92%) of the 3RS diastereomer which was subjected to the conditions of Example 3 (c) using Na (0.35 g, 15.3 g-atom) in ethanol to afford 4.2 g (88%) of the title compound. mp=83–85° C. FDMS: $M^+$=312. Anal. calcd. for $C_{16}H_{15}F_3O_3$-$C_6H_{14}$: C, 62.13; H, 5.15. Found: C, 62.44; H, 4.94.

(c) 1SR,2SR,3SR,5RS,6SR-Ethyl-2-aminoacetyl-2-cyano-3-((2,3,4-trifluoro)benzyl)-bicyclo[3.1.0]hexane-6-carboxylate. The title compounds were prepared according to the method of Example 2 (c) employing the product of step (c) (4.0 g, 12.8 mmol), KCN (8.3 g, 128 mmol), $NH_4Cl$ (6.9 g, 128 mmol) and $Al_2O_3$ (40 g). The intermediate amino nitrile was acylated using acetyl chloride (1.4 g, 18.2 mmol) and N,N-diisopropylethylamine (2.4 g, 18.2 mmol). The crude product was purified by crystallization from $CH_2Cl_2$ to give 2.2 g (47%) of the title compound. mp=246–249° C. FDMS: $M^+$=380. Anal. calcd. for $C_{19}H_{19}F_3N_2O_3$: C, 60.00; H, 5.03; N, 7.36. Found: C, 59.75; H, 4.96; N, 7.20.

(d) The title compound was prepared according to Example 3 (e) employing the 2SR product of step (c) (0.52 g, 1.4 mmol) and 2N HCl (100 mL). The product was isolated at pH 5 affording 0.3 g (68%) of the title compound. mp>250° C. FDMS: $M^+$=329. Anal. calcd. for $C_{15}H_{14}F_3N_1O_4$: C, 54.72; H, 4.29; N, 4.25. Found: C, 54.81; H, 4.42; N, 4.40.

EXAMPLE 26

1SR,2SR,3SR,5RS,6SR-2-Amino-3-methylbicyclo[3.1.0]hexane-2,6-dicarboxylic acid (a) (1SR,3RS,5RS,6SR)Ethyl-2-oxo-3-methylbicyclo[3.1.0]hexane-6-carboxylate. To a solution of the product of Preparation 2 (317 mg, 1.88 mmol) in anhydrous THF (30 ml) at −78° C. and under argon was added a 1M solution of lithium hexamethyldisilazide in THF (1.9 ml, 1.88 ml). The reaction mixture was stirred for 45 min at this temperature and then this solution was cannuled over a solution of methyl iodide (0.35 ml, 5.6 mmol) in THF (10 ml) at −78° C. The reaction mixture was stirred for 1 h at −78° C. and overnight at room temperature, quenched with saturated ammonium chloride solution (20 ml), and extracted with methylene chloride (3×50 ml). The combined organic phases were dried over $MgSO_4$, filtered, and evaporated to dryness. Purification of the crude by flash chromatography (Hexane/Ethyl Acetate 4:1) gave as a pale yellow oil the title compound. Yield: 70%. $^1$H NMR ($CDCL_3$),δ:4.0(q,2H,J=7.1 Hz),2.32–2.1(m,3H),1.98–1.85 (m,2H),1.75–1.6(m,1H), 1.15(t,3H,J=7.1 Hz),0.9(d,3H,J=6.9 Hz) $^{13}$C NMR (CDCL3),δ: 212,170.26,60.95,31.46,35.77,35.21,27.19, 27.07,13.95,13.79.

(b) (1SR,2SR,3SR,5RS,6SR)-Ethyl-2-Spiro-5-Hydantoin-3-methylbicyclo[3.1.0]hexane-6-carboxylate. To a solution of the product of step (a) (500 mg, 2.7 mmol) in ethanol (1.3 ml) and water (3.3 ml), potassium cyanide (195 mg, 3 mmol) and ammonium carbonate (782 mg, 8.1 mmol) were added. The mixture was heated at 55° C. overnight and the resulting solid was filtered and washed with EtOH—$H_2O$ to afford the title compound. Yield: 40%.$^1$H NMR (DMSO),δ:10.65(s,1H),7.9 (s,1H),4.05(q,2H,J=7.1 Hz), 2.05–1.6(m,5H),1.2(t,3H,J=7.1 Hz), 0.8 (d,3H,J=5.9)$^{13}$C NMR(DMSO),δ: 175.86,172.02,156.75,71.86, 60.40,35.76, 33.12,32.00,25.97,20.48,14.27,12.18.

(c) A mixture of the product of step (b) and 12N HCl solution (10 ml) was refluxed in a reactor overnight. The resulting solution was evaporated to dryness yielding a white solid. The title compound was isolated as a zwitterion after ion exchange chromatography on Dowex 50×8 50–100 Mesh using pyridine-water 10% as eluent. Yield: 40%.$^1$H NMR ($D_2O$-Pyr-$d_5$),δ:2.0–1.7(m,6H),0.9(d,3H)$^{13}$C NMR ($D_2O$)-Pyr-$d_5$),δ:179.95,173.37,70.08,36.46,33.69,31.79, 26.44,23.75,12.18 IR (KBr)1697.57,1678.28 $cm^{-1}$.

EXAMPLE 27

1SR,2SR,3SR,5RS,6SR-2-Amino-3-((4-fluoro-3-methyl)benzyl)bicyclo[3.1.0]hexane-2,6-dicarboxylic acid a) 1SR,5RS,6SR-Ethyl-2-oxo-3-((4-fluoro-3-methyl)benzylidenyl)bicyclo[3.1.0]hexane-6-carboxylate. The title compound was prepared according to the method of Example 18 (a) employing the product of Preparation 2 (17.0 g, 101 mmol), 4-fluoro-3-methylbenzaldehyde (15 g, 108 mmol) and pyrrolidine (2 mL) in EtOH (200 mL). The precipitate which formed was filtered and dried to yield 16.5 g (57%) of the title compound. mp=147–149° C.

(b) 1SR,3RS,5RS,6SR-Ethyl-2-oxo-3-((4-fluoro-3-methyl)benzyl)bicyclo[3.1.0]hexane-6-carboxylate. The title compound was prepared according to the method of Example 1 (c) employing the product of step (a) (15.3 g, 53.1 mmol) and Raney Ni (3.8 g). The crude product was purified by HPLC (10% EtOAc/hexane to 50% EtOAc/hexane) yielding 14.1 g (91%) of the title compound.

(c) 1SR,2SR,3SR,5RS,6SR-Ethyl-2-oxo-3-((4-fluoro-3-methyl)benzyl)bicyclo[3.1.0]hexane-6-carboxylate. The title compound was prepared according to the method of Example 3 (c) employing the product of step (b) (14.0 g, 48.2 mmol) and Na (1.11 g, 48.2 g-atom). The reaction was concentrated to yield 12.6 g (90%) of the title compound. mp=72–74° C. FDMS: $M^+$=290. Anal. calcd. for $C_{17}H_{19}FO_3$: C, 70.33; H, 6.60. Found: C, 70.58; H, 6.57.

d) 1SR,2SR,3SR,5RS,6SR-Ethyl-2-aminoacetyl-2-cyano-3-((4-fluoro-3-methyl)benzyl)bicyclo[3.1.0]hexane-6-carboxylate and 1SR,2RS,3SR,5RS,6SR-Ethyl-2-aminoacetyl-2-cyano-3-((4-fluoro-3-methyl)benzyl)bicyclo[3.1.0]hexane-6-carboxylate. The title compounds were prepared according to the method of Example 2 (c) employing the product of step (c) (12.0 g, 41.3 mmol), KCN (26.9 g, 413 mmol), $NH_4Cl$ (22.1 g, 413 mmol) and $Al_2O_3$ (100 g). The intermediate amino nitrile was acylated using acetyl chloride (4.7 g, 59.7 mmol) and N,N-diisopropylethylamine (7.7 g, 59.7 mmol). The crude product was purified by HPLC (20% EtOAc/hexane to 60% EtOAc/hexane) yielding 4.3 g (29%) of 1SR,2SR,3SR,5RS,6SR-ethyl-2-aminoacetyl-2-cyano-3-((4-fluoro-3-methyl)benzyl)bicyclo [3.1.0]hexane-6-carboxylate (A) and 2.8 g (19%) of 1SR, 2RS,3SR,5RS,6SR-ethyl-2-aminoacetyl-2-cyano-3-((4-fluoro-3-methyl)benzyl)bicyclo[3.1.0]hexane-6-carboxylate (B).

(e) 1SR,2SR,3SR,5RS,6SR-2-Amino-3-((4-fluoro-3-methyl)benzyl)bicyclo[3.1.0]hexane-2,6-dicarboxylic acid. The title compound prepared by the method of Example 3 (e) employing the 2SR product of step (d) (3.6 g, 10.0 mmol). The crude product was dissolved in $H_2O$ at pH 10 and filtered. The product was precipitated at pH 3, filtered and washed with $H_2O$, IPA and EtOAc, yielding 2.48 g (81%) of the title compound. mp=243–246° C. FDMS: M+−45(CO$_2$H)=262. Anal. calcd. for C$_{16}$H$_{18}$FNO$_4$: C, 60.80; H, 5.74; N, 4.43. Found: C, 61.03; H, 5.48; N, 4.67.

EXAMPLE 28

1SR,2SR,3SR,5RS,6SR-2-Amino-3-((3-fluoro-5-(trifluoromethyl))benzyl)bicyclo[3.1.0]hexane-2,6-dicarboxylic acid (a) 1SR,5RS,6SR-Ethyl-2-oxo-3-((3-fluoro-5-(trifluoromethyl))benzylidenyl)bicyclo[3.1.0]hexane-6-carboxylate. The title compound was prepared according to the method of Example 18 (a) employing the product of Preparation 2 (4.4 g, 26.0 mmol), 3-fluoro-5-(trifluoromethyl)benzaldehyde (5.0 g, 26.0 mmol) and pyrrolidine (1.0 mL) in EtOH (150 mL). The product precipitated from solution and was filtered yielding 7.1 g (80%) of the title compound. mp=131–133° C. FDMS: M+=342. Anal. calcd. for C$_{17}$H$_{14}$F$_4$O$_3$: C, 59.65; H, 4.12. Found: C, 59.79; H, 4.25.

(b) 1SR,3RS,5RS,6SR-Ethyl-2-oxo-3-((3-fluoro-5-(trifluoromethyl))benzyl)bicyclo[3.1.0]hexane-6-carboxylate. The title compound was prepared according to the method of Example 1 (c) employing the product of step (a) (6.4 g, 18.6 mmol), Raney Ni (1.6 g) with H$_2$ at 50 psi. The crude product was purified by HPLC (10% EtOAc/hexane to 50% EtOAc/hexane) yielding 5.8 g (89%) of the title compound.

(c) 1SR,3SR,5RS,6SR-Ethyl-2-oxo-3-((3-fluoro-5-(trifluoromethyl))benzyl)bicyclo[3.1.0]hexane-6-carboxylate. The title compound was prepared according to the method of Example 3 (c) employing the product of step (b) (5.8 g, 16.9 mmol) and Na (0.39 g, 16.9 g-atom). The reaction was concentrated to yield 4.6 g (80%) of the title compound. mp=105–107° C. FDMS: M+=344; Anal. calcd. for C$_{17}$H$_{16}$F$_4$O$_3$: C, 59.30; H, 4.68. Found: C, 59.56; H, 4.79.

d) 1SR,2SR,3SR,5RS,6SR-Ethyl-2-aminoacetyl-2-cyano-3-((3-fluoro-5-(trifluoromethyl))benzyl)bicyclo[3.1.0]hexane-6-carboxylate and 1SR,2RS,3SR,5RS,6SR-Ethyl-2-aminoacetyl-2-cyano-3-((3-fluoro-5-(trifluoromethyl))benzyl)bicyclo[3.1.0]hexane-6-carboxylate. The title compounds were prepared according to the method of Example 2 (c) employing the product of step (c) (4.0 g, 11.6 mmol), KCN (7.5 g, 116 mmol), NH$_4$Cl (6.2 g, 116 mmol) and Al$_2$O$_3$ (40 g). The intermediate amino nitrile was acylated using acetyl chloride (1.4 g, 18.2 mmol) and N,N-diisopropylethylamine (2.3 g, 18.2 mmol). The crude product was purified by HPLC (10% EtOAc/hexane to 80% EtOAc/hexane) yielding 2.3 g (48%) of 1SR,2SR,3SR,5RS,6SR-ethyl-2-aminoacetyl-2-cyano-3-((3-fluoro-5-(trifluoromethyl))benzyl)bicyclo[3.1.0]hexane-6-carboxylate (A) and 1.0 g (21%) of 1SR,2RS,3SR,5RS,6SR-ethyl-2-aminoacetyl-2-cyano-3-((3-fluoro-5-(trifluoromethyl))benzyl)bicyclo[3.1.0]hexane-6-carboxylate (B). (A): mp=136–138° C. FDMS: M+=412. Anal. calcd. for C$_{20}$H$_{20}$F$_4$N$_2$O$_3$: C, 58.25; H, 4.89; N, 6.79. Found: C, 58.53; H, 5.01; N, 6.82. (B): mp=65–85° C. (glass). FDMS: M+=412. Anal. calcd. for C$_{20}$H$_{20}$F$_4$N$_2$O$_3$: C, 58.25; H, 4.89; N, 6.79. Found: C, 58.15; H, 4.87; N, 6.72.

(e) 1SR,2SR,3SR,5RS,6SR-2-Amino-3-((3-fluoro-5-(trifluoromethyl))benzyl)bicyclo[3.1.0]hexane-2,6-dicarboxylic acid. The title compound was prepared by the method of Example 3 (e) employing the 2SR product of step (d) (1.7 g, 4.3 mmol). The crude product was dissolved in H$_2$O at pH 10 and filtered. The product was precipitated at pH 3, filtered and washed with H$_2$O, IPA and EtOAc, yielding 1.07 g (69%) of the title compound. mp>250° C. FDMS: M++1=362. Anal. calcd. for C$_{16}$H$_{15}$F$_4$NO$_4$: C, 53.19; H, 4.18; N, 3.88. Found: C, 53.46; H, 4.08; N, 3.86.

EXAMPLE 29

1SR,2SR,3SR,5RS,6SR-2-Amino-3-((2-chloro-5-(trifluoromethyl))benzyl)bicyclo[3.1.0]hexane-2,6-dicarboxylic acid (a) 1SR,5RS,6SR-Ethyl-2-oxo-3-((2-chloro-5-(trifluoromethyl))benzylidenyl)bicyclo[3.1.0]hexane-6-carboxylate. The title compound was prepared according to the method of Example 18 (a) employing the product of Preparation 2 (4.0 g, 24.0 mmol), 2-chloro-5-(trifluoromethyl)benzaldehyde (5.1 g, 24.0 mmol) and pyrrolidine (1.0 mL) in EtOH (150 mL). Isolated 4.2 g (49%) of the title compound. mp=87–89° C. FDMS: M+=358. Anal. calcd. for C$_{17}$H$_{14}$ClF$_3$O$_3$: C, 56.92; H, 3.93. Found: C, 57.16; H, 4.07.

(b) 1SR,3RS,5RS,6SR-Ethyl-2-oxo-3-((2-chloro-5-(trifluoromethyl))benzyl)bicyclo[3.1.0]hexane-6-carboxylate. The title compound was prepared according to the method of Example 1 (c) employing the product of step (a) (4.1 g, 11.4 mmol), Raney Ni (1.0 g) with H$_2$ at 40 psi. The crude product was purified by HPLC (10% EtOAc/hexane to 50% EtOAc/hexane) yielding 3.9 g (95%) of the title compound.

(c) 1SR,3SR,5RS,6SR-Ethyl-2-oxo-3-((2-chloro-5-(trifluoromethyl))benzyl)bicyclo[3.1.0]hexane-6-carboxylate. The title compound was prepared according to the method of Example 3 (c) employing the product of step (b) (3.8 g, 10.5 mmol) and Na (0.24 g, 10.4 g-atom). The reaction was concentrated to yield 3.5 g (92%) of the title compound. mp=69–71° C. FDMS: M+=360; Anal. calcd. for C$_{17}$H$_{16}$ClF$_3$O$_3$: C, 56.60; H, 4.47. Found: C, 56.43; H, 4.52.

d) 1SR,2SR,3SR,5RS,6SR-Ethyl-2-aminoacetyl-2-cyano-3-((2-chloro-5-(trifluoromethyl))benzyl)bicyclo[3.1.0]hexane-6-carboxylate and 1SR,2RS,3SR,5RS,6SR-Ethyl-2-aminoacetyl-2-cyano-3-((2-chloro-5-(trifluoromethyl))benzyl)bicyclo[3.1.0]hexane-6-carboxylate. The title compounds were prepared according to the method of Example 2 (c) employing the product of step (c) (3.4 g, 9.4 mmol), KCN (6.1 g, 94 mmol), NH$_4$Cl (5.0 g, 94 mmol) and Al$_2$O$_3$ (44 g). The intermediate amino nitrile was acylated using acetyl chloride (1.0 g, 12.7 mmol) and N,N-diisopropylethylamine (1.7 g, 12.7 mmol). The crude product was purified by HPLC (10% EtOAc/hexane to 80% EtOAc/hexane) yielding 1.5 g (37%) of 1SR,2SR,3SR,5RS,6SR-ethyl-2-aminoacetyl-2-cyano-3-((2-chloro-5-(trifluoromethyl))benzyl)bicyclo[3.1.0]hexane-6-carboxylate (A) and 1.0 g (25%) of 1SR,2RS,3SR,5RS,6SR-ethyl-2-aminoacetyl-2-cyano-3-((2-chloro-5-(trifluoromethyl))benzyl)bicyclo[3.1.0]hexane-6-carboxylate (B). (A): mp=144–145° C. FDMS: M+=428. Anal. calcd. for C$_{20}$H$_{20}$ClF$_3$N$_2$O$_3$: C, 56.02; H, 4.70; N, 6.53. Found: C, 56.27; H, 4.99; N, 6.44. (B): mp=124–126° C. FDMS: M+=428. Anal. calcd. for C$_{20}$H$_{20}$ClF$_3$N$_2$O$_3$: C, 56.02; H, 4.70; N, 6.53. Found: C, 55.93; H, 4.67; N, 6.24.

(e) 1SR,2SR,3SR,5RS,6SR-2-Amino-3-((2-chloro-5-(trifluoromethyl))benzyl)bicyclo[3.1.0]hexane-2,6-dicarboxylic acid. The title compound prepared by the method of Example 3 (e) employing the 2SR product of step (d) (1.2 g, 2.8 mmol). The crude product was dissolved in H$_2$O at pH 10 and filtered. The product was precipitated at pH 3, filtered and washed with H$_2$O, IPA and EtOAc, yielding 0.9 g (85%) of the title compound. mp=252–254° C. FDMS: M$^+$+1=378. Anal. calcd. for $C_{16}H_{15}ClF_3NO_4$: C, 50.87; H, 4.00; N, 3.71. Found: C, 50.94; H, 4.22; N, 3.68.

EXAMPLE 30

1SR,2SR,3SR,5RS,6SR-2-Amino-3-((3-fluoro-2-methyl)benzyl)bicyclo[3.1.0]hexane-2,6-dicarboxylic acid (a) 1SR,5RS,6SR-Ethyl-2-oxo-3-((3-fluoro-2-methyl)benzylidenyl)bicyclo[3.1.0]hexane-6-carboxylate. The title compound was prepared according to the method of Example 18 (a) employing the product of Preparation 2 (6.0 g, 36.0 mmol), 3-fluoro-2-methylbenzaldehyde (5.0 g, 36.2 mmol) and pyrrolidine (1.0 mL) in EtOH (150 mL). Isolated 6.2 g (60%) of the title compound. mp=96–98° C. FDMS: M$^+$=288. Anal. calcd. for $C_{17}H_{17}F_1O_3$: C, 70.82; H, 5.94. Found: C, 71.07; H, 5.98.

(b) 1SR,3RS,5RS,6SR-Ethyl-2-oxo-3-((3-fluoro-2-methyl)benzyl)bicyclo[3.1.0]hexane-6-carboxylate. The title compound was prepared according to the method of Example 1 (c) employing the product of step (a) (6.1 g, 21.1 mmol), Raney Ni (1.5 g) with H$_2$ at 40 psi. The crude product was purified by HPLC (5% EtOAc/hexane to 50% EtOAc/hexane) yielding 5.4 g (89%) of the title compound.

(c) 1SR,3RS,5RS,6SR-Ethyl-2-oxo-3-((3-fluoro-2-methyl)benzyl)bicyclo[3.1.0]hexane-6-carboxylate. The title compound was prepared according to the method of Example 3 (c) employing the product of step (b) (5.4 g, 18.6 mmol) and Na (0.43 g, 18.6 g-atom). The reaction was concentrated to yield 5.0 g (93%) of the title compound. mp=77–79° C. FDMS: M$^+$=290; Anal. calcd. for $C_{17}H_{19}F_1O_3$: C, 70.33; H, 6.60. Found: C, 70.58; H, 6.63.

d) 1SR,2SR,3SR,5RS,6SR-Ethyl-2-aminoacetyl-2-cyano-3-((3-fluoro-2-methyl)benzyl)bicyclo[3.1.0]hexane-6-carboxylate. The title compound was prepared according to the method of Example 2 (c) employing the product of step (c) (4.7 g, 16.2 mmol), KCN (10.5 g, 162 mmol), NH$_4$Cl (8.7 g, 162 mmol) and Al$_2$O$_3$ (50 g). The intermediate amino nitrile was acylated using acetyl chloride (1.86 g, 23.7 mmol) and N,N-diisopropylethylamine (3.06 g, 23.7 mmol). The crude product was purified by crystallization from CH$_2$Cl$_2$ and recrystallized a second time from EtOAc, yielding 1.3 g (22%) of 1SR,2SR,3SR,5RS,6SR-ethyl-2-aminoacetyl-2-cyano-3-((3-fluoro-2-methyl)benzyl)bicyclo[3.1.0]hexane-6-carboxylate (A). (A): mp=240–242° C. FDMS: M$^+$=358. Anal. calcd. for $C_{20}H_{23}F_1N_2O_3$: C, 67.02; H, 6.47; N, 7.82. Found: C, 66.90; H, 6.19; N, 7.76.

(e) 1SR,2SR,3SR,5RS,6SR-2-Amino-3-((3-fluoro-2-methyl)benzyl)bicyclo[3.1.0]hexane-2,6-dicarboxylic acid. The title compound was prepared by the method of Example 3 (e) employing the product of step (d) (1.0 g, 2.8 mmol). The crude product was dissolved in H$_2$O at pH 10 and filtered. The product was precipitated at pH 3, filtered and washed with H$_2$O, IPA and EtOAc, yielding 0.38 g (45%) of the title compound. mp=247–248° C., FDMS: M$^+$=307. Anal. calcd. for $C_{16}H_{18}FNO_4$.0.3 H$_2$O: C, 61.45; H, 5.99; N, 4.48. Found: C, 61.45; H, 5.89; N, 4.66.

EXAMPLE 31

1SR,2SR,3SR,5RS,6SR-2-Amino-3-((3-(1,1,2,2-tetrafluoroethoxy))benzyl)bicyclo[3.1.0]hexane-2,6-dicarboxylic acid (a) 1SR,5RS,6SR-Ethyl-2-oxo-3-((3-(1,1,2,2-tetrafluoroethoxy))benzylidenyl)bicyclo[3.1.0]hexane-6-carboxylate. The title compound was prepared according to the method of Example 18 (a) employing the product of Preparation 2 (3.6 g, 21.4 mmol), 3-(1,1,2,2-tetrafluoroethoxy)benzaldehyde (5.0 g, 21.5 mmol) and pyrrolidine (1.0 mL) in EtOH (150 mL). The crude product was purified by HPLC (5% EtOAc/hexane to 50% EtOAc/hexane) yielding 6.4 g (80%) of the title compound. mp=84–86° C. FDMS: M$^+$+1=373. Anal. calcd. for $C_{18}H_{16}F_4O_4$.0.25 toluene(from EtOH): C, 60.00; H, 4.59. Found: C, 60.17; H, 4.39.

(b) 1SR,3RS,5RS,6SR-Ethyl-2-oxo-3-((3-(1,1,2,2-tetrafluoroethoxy))benzyl)bicyclo[3.1.0]hexane-6-carboxylate. The title compound was prepared according to the method of Example 1 (c) employing the product of step (a) (5.6 g, 15.0 mmol) and Raney Ni (1.4 g). The crude product was purified by HPLC (5% EtOAc/hexane to 50% EtOAc/hexane) yielding 4.8 g (85%) of the title compound.

(c) 1SR,3RS,5RS,6SR-Ethyl-2-oxo-3-((3-(1,1,2,2-tetrafluoroethoxy))benzyl)bicyclo[3.1.0]hexane-6-carboxylate. The title compound was prepared according to the method of Example 3 (c) employing the product of step (b) (4.8 g, 12.8 mmol) and Na (0.29 g, 12.8 g-atom). The reaction was concentrated to yield 4.3 g (90%) of the title compound. mp=56–58° C. FDMS: M$^+$=374; Anal. calcd. for $C_{18}H_{18}F_4O_4$: C, 57.76; H, 4.85. Found: C, 57.21; H, 4.82.

d) 1SR,2SR,3SR,5RS,6SR-Ethyl-2-aminoacetyl-2-cyano-3-((3-(1,1,2,2-tetrafluoroethoxy))benzyl)bicyclo[3.1.0]hexane-6-carboxylate. The title compound was prepared according to the method of Example 2 (c) employing the product of step (c) (3.8 g, 10.1 mmol), KCN (6.6 g, 101 mmol), NH$_4$Cl (5.4 g, 101 mmol) and Al$_2$O$_3$ (40 g). The intermediate amino nitrile was acylated using acetyl chloride (1.1 g, 14.3 mmol) and N,N-diisopropylethylamine (1.8 g, 14.3 mmol). The crude product was purified by HPLC (10% EtOAc/hexane to 80% EtOAc/hexane) yielding 1.8 g (40%) of 1SR,2SR,3SR,5RS,6SR-ethyl-2-aminoacetyl-2-cyano-3-((3-(1,1,2,2-tetrafluoroethoxy))benzyl)bicyclo[3.1.0]hexane-6-carboxylate. mp=165–168° C. FDMS: M$^+$=442. Anal. calcd. for $C_{21}H_{22}F_4N_2O_4$: C, 57.01; H, 5.01; N, 6.41. Found: C, 56.77; H, 4.83; N, 6.41.

(e) 1SR,2SR,3SR,5RS,6SR-2-Amino-3-((3-(1,1,2,2-tetrafluoroethoxy))benzyl)bicyclo[3.1.0]hexane-2,6-dicarboxylic acid. The title compound was prepared by the method of Example 3 (e) employing the product of step (d) (1.8 g, 3.8 mmol). The crude product was dissolved in H$_2$O at pH 10 and filtered. The product was precipitated at pH 3, filtered and washed with H$_2$O, IPA and EtOAc, yielding 0.89 g (59%) of the title compound. mp>250° C. FDMS: M$^+$-45 (CO$_2$H)=346. Anal. calcd. for $C_{17}H_{17}F_4NO_5$.0.25 EtOAc: C, 52.30; H, 4.63; N, 3.38. Found: C, 52.57; H, 4.38; N, 2.98.

EXAMPLE 32

1SR,2SR,3SR,5RS,6SR-2-Amino-3-((1,1-diphenyl)methyl)bicyclo[3.1.0]hexane-2,6-dicarboxylic acid (a) 1SR,3RS,5RS,6SR-Ethyl-2-oxo-3-((1,1-diphenyl)methyl)bicyclo[3.1.0]hexane-6-carboxylate. A mixture of phenyl bromide (7.5 g, 46.8 mmol), ZnBr$_2$ (5.4 g, 23.9 mmol), and lithium wire (0.65 g, 93 g-atom) in Et$_2$O were sonicated under N$_2$ using a Branson 3200 ultrasonic bath for 1 hour at ambient temperature. The reaction was cooled to 0° C. and a mixture of 1SR,5RS,6SR-Ethyl-2-oxo-3-(benzylidenyl)bicyclo[3.1.0]hexane-6-carboxylate (6.0 g, 23.4 mmol), NiAcAc (0.1 g, 0.4 mmol) was added dropwise over 1.5 h. The reaction was then stirred at ambient temperature for 3 h and quenched with saturated aqueous NH$_4$Cl. The reaction mixture was partitioned between aqueous NH$_4$Cl and Et$_2$O. The organic layer was washed with brine, dried with MgSO$_4$, filtered and concentrated under reduced pressure. The crude product was purified by HPLC (10% EtOAc/hexane to 50% EtOAc/hexane) affording 1.8 g (23%) of the title compound. mp=110–114° C. FDMS: M$^+$=334; Anal. calcd. for C$_{22}$H$_{22}$O$_3$C: 79.02; H, 6.63. Found: C, 79.15; H, 6.72.

(b) 1SR,2SR,3SR,5RS,6SR-Ethyl-2-aminoacetyl-2-cyano-3-((1,1-diphenyl)methyl)bicyclo[3.1.0]hexane-6-carboxylate. The title compound was prepared according to the method of Example 2 (c) employing the product of step (a) (1.7 g, 5.0 mmol), KCN (3.2 g, 50 mmol), NH$_4$Cl (2.6 g, 50 mmol) and Al$_2$O$_3$ (28 g). The intermediate amino nitrile was acylated using acetyl chloride (1.0 g, 7.5 mmol) and N,N-diisopropylethylamine (0.6 g, 7.5 mmol). The crude product was purified by HPLC (10% EtOAc/hexane to 80% EtOAc/hexane) yielding 0.85 g (42%) of 1SR,2SR,3SR,5RS,6SR-ethyl-2-aminoacetyl-2-cyano-3-((1,1-diphenyl)methyl)bicyclo[3.1.0]hexane-6-carboxylate. mp=95–105° C. (glass). FDMS: M$^+$=402. Anal. calcd. for C$_{25}$H$_{26}$N$_2$O$_3$: C, 74.60; H, 6.51; N, 6.96. Found: C, 74.87; H, 6.41; N, 6.68.

(c) 1SR,2SR,3SR,5RS,6SR-2-Amino-3-((1,1-diphenyl)methyl)bicyclo[3.1.0]hexane-2,6-dicarboxylic acid. The title compound prepared by the method of Example 3 (e) employing the product of step (b) (0.42 g, 1.0 mmol). The crude product was dissolved in H$_2$O at pH 10 and filtered. The product was precipitated at pH 3, filtered and washed with H$_2$O, IPA and EtOAc, yielding 0.26 g (70%) of the title compound. mp=238–240° C., FDMS: M$^+$-45(CO$_2$H)=306. Anal. calcd. for C$_{21}$H$_{21}$NO$_4$: C, 71.78; H, 6.02; N, 3.98. Found: C, 71.50; H, 5.94; N, 3.92.

EXAMPLE 33

1SR,2SR,3SR,5RS,6SR-2-Amino-3-((2,5-difluoro)benzyl)bicyclo[3.1.0]hexane-2,6-dicarboxylic acid (a) 1SR,5RS,6SR-Ethyl-2-oxo-3-((2,5-difluoro)benzylidenyl)bicyclo[3.1.0]hexane-6-carboxylate. The title compound was prepared according to the method of Example 18 (a) employing the product of Preparation 2 (5.8 g, 34.5 mmol), 2,5-difluorobenzaldehyde (4.9 g, 34.5 mmol) and pyrrolidine (1.0 mL) in EtOH (150 mL). The crude product was purified by HPLC (5% EtOAc/hexane to %50 EtOAc/hexane) yielding 8.5 g (84%) of the title compound. mp=84–85° C. FDMS: M$^+$=292. Anal. calcd. for C$_{16}$H$_{14}$F$_2$O$_3$: C, 65.75; H, 4.83. Found: C, 66.05; H, 4.93.

(b) 1SR,3RS,5RS,6SR-Ethyl-2-oxo-3-((2,5-difluoro)benzyl)bicyclo[3.1.0]hexane-6-carboxylate. The title compound was prepared according to the method of Example 1 (c) employing the product of step (a) (8.3 g, 28.4 mmol) and Raney Ni (2.0 g). The crude product was purified by HPLC (10% EtOAc/hexane to 50% EtOAc/hexane) yielding 8.3 g (99%) of the title compound.

(c) 1SR,3SR,5RS,6SR-Ethyl-2-oxo-3-((2,5-difluoro)benzyl)bicyclo[3.1.0]hexane-6-carboxylate. The title compound was prepared according to the method of Example 3 (c) employing the product of step (b) (8.0 g, 27.2 mmol) and Na (0.63 g, 27.2 g-atom). The reaction was concentrated to yield 7.2 g (90%) of the title compound. mp=65–68° C. FDMS: M$^+$=294; Anal. calcd. for C$_{16}$H$_{16}$F$_2$O$_3$: C, 65.30; H, 5.48. Found: C, 65.49; H, 5.56.

d) 1SR,2SR,3SR,5RS,6SR-Ethyl-2-aminoacetyl-2-cyano-3-((2,5-difluoro)benzyl)bicyclo[3.1.0]hexane-6-carboxylate. The title compound was prepared according to the method of Example 2 (c) employing the product of step (c) (6.9 g, 23.5 mmol), KCN (15.3 g, 235 mmol), NH$_4$Cl (12.5 g, 235 mmol) and Al$_2$O$_3$ (50 g). The intermediate amino nitrile was acylated using acetyl chloride (2.7 g, 34 mmol) and N,N-diisopropylethylamine (4.4 g, 34 mmol). The crude product was purified by crystallization from CH$_2$Cl$_2$ yielding 1.65 g (19%) of 1SR,2SR,3SR,5RS,6SR-ethyl-2-aminoacetyl-2-cyano-3-((2,5-difluoro)benzyl)bicyclo[3.1.0]hexane-6-carboxylate. mp=192–196° C. FDMS: M$^+$=362. Anal. calcd. for C$_{19}$H$_{20}$F$_2$N$_2$O$_3$: C, 61.86; H, 5.49; N, 7.55. Found: C, 61.84; H, 5.49; N, 8.90.

(e) 1SR,2SR,3SR,5RS,6SR-2-Amino-3-((2,5-difluoro)benzyl)bicyclo[3.1.0]hexane-2,6-dicarboxylic acid. The title compound was prepared by the method of Example 3 (e) employing the 2SR product of step (d) (1.3 g, 3.6 mmol). The crude product was dissolved in H$_2$O at pH 10 and filtered. The product was precipitated at pH 3, filtered and washed with H$_2$O, IPA and EtOAc, yielding 0.84 g (71%) of the title compound. mp=243–245° C. FDMS: M$^+$+1=312. Anal. calcd. for C$_{15}$H$_{15}$F$_2$NO$_4$: C, 57.88; H, 4.86; N, 4.50. Found: C, 57.88; H, 5.02; N, 4.61.

EXAMPLE 34

1SR,2SR,3SR,5RS,6SR-2-Amino-3-((3,5-dimethyl)benzyl)bicyclo[3.1.0]hexane-2,6-dicarboxylic acid (a) 1SR,5RS,6SR-Ethyl-2-oxo-3-((3,5-dimethyl)benzylidenyl)bicyclo[3.1.0]hexane-6-carboxylate. The title compound was prepared according to the method of Example 18 (a) employing the product of Preparation 2 (5.6 g, 34.3 mmol), 3,5-dimethylbenzaldehyde (4.6 g, 34.3 mmol) and pyrrolidine (1.1 mL) in EtOH (150 mL). Isolated 7.2 g (77%) of the title compound by filtration. mp=104–105° C. FDMS: M$^+$=284. Anal. calcd. for C$_{18}$H$_{20}$O$_3$: C, 76.03; H, 7.09. Found: C, 76.12; H, 6.92.

(b) 1SR,3RS,5RS,6SR-Ethyl-2-oxo-3-((3,5-dimethyl)benzyl)bicyclo[3.1.0]hexane-6-carboxylate. The title compound was prepared according to the method of Example 1 (c) employing the product of step (a) (6.3 g, 22.2 mmol) and Raney Ni (1.6 g). The crude product was purified by HPLC (10% EtOAc/hexane to 50% EtOAc/hexane) yielding 6.0 g (95%) of the title compound.

(c) 1SR,3SR,5RS,6SR-Ethyl-2-oxo-3-((3,5-dimethyl)benzyl)bicyclo[3.1.0]hexane-6-carboxylate . The title compound was prepared according to the method of Example 3 (c) employing the product of step (b) (5.8 g, 20.3 mmol) and Na (0.47 g, 20.3 g-atom). The reaction was concentrated to yield 5.0 g (86%) of the title compound. FDMS: M$^+$=286; Anal. calcd. for C$_{18}$H$_{22}$O$_3$: C, 75.50; H, 7.74. Found: C, 75.72; H, 8.02.

d) 1SR,2SR,3SR,5RS,6SR-Ethyl-2-aminoacetyl-2-cyano-3-((3,5-dimethyl)benzyl)bicyclo[3.1.0]hexane-6-carboxylate. The title compound was prepared according to the method of Example 2 (c) employing the product of step (c) (4.5 g, 15.7 mmol), KCN (10.2 g, 157 mmol), NH$_4$Cl (8.4 g, 157 mmol) and Al$_2$O$_3$ (45 g). The intermediate amino nitrile was acylated using acetyl chloride (1.9 g, 24.5 mmol) and N,N-diisopropylethylamine (3.2 g, 24.5 mmol). The crude product was purified by crystallization from EtOAc/hexane yielding 1.48 g (26%) of 1SR,2SR,3SR,5RS,6SR-ethyl-2-aminoacetyl-2-cyano-3-((3,5-dimethyl)benzyl)bicyclo[3.1.0]hexane-6-carboxylate. mp=190–191° C. FDMS: M$^+$=354. Anal. calcd. for C$_{21}$H$_{26}$N$_2$O$_3$: C, 71.16; H, 7.39; N, 7.90. Found: C, 71.03; H, 7.45; N, 8.20.

(e) 1SR,2SR,3SR,5RS,6SR-2-Amino-3-((3,5-dimethyl)benzyl)bicyclo[3.1.0]hexane-2,6-dicarboxylic acid. The title compound was prepared by the method of Example 3 (e) employing the product of step (d) (1.1 g, 3.1 mmol). The crude product was dissolved in $H_2O$ at pH 10 and filtered. The product was precipitated at pH 3, filtered and washed with $H_2O$, IPA and EtOAc, yielding 0.74 g (78%) of the title compound. mp>260° C. FDMS: $M^++1$=304. Anal. calcd. for $C_{17}H_{21}NO_4$.0.22 EtOAc: C, 66.54; H, 7.11; N, 4.34. Found: C, 66.94; H, 6.79; N, 3.85.

EXAMPLE 35

1SR,2SR,3SR,5RS,6SR-2-Amino-3-((3-(3-(trifluoromethyl)phenoxy))benzyl)bicyclo[3.1.0]hexane-2,6-dicarboxylic acid (a) 1SR,5RS,6SR-Ethyl-2-oxo-3-((3-(3-(trifluoromethyl))phenoxy)benzylidenyl)bicyclo[3.1.0]hexane-6-carboxylate. The title compound was prepared according to the method of Example 18 (a) employing the product of Preparation 2 (3.1 g, 18.8 mmol), 3-(3-(trifluoromethyl)phenoxy)benzaldehyde (5.0 g, 18.8 mmol) and pyrrolidine (1.0 mL) in EtOH (150 mL). Isolated 6.1 g (78%) of the title compound by filtration. mp=98–100° C. FDMS: $M^+$=416. Anal. calcd. for $C_{23}H_{19}F_3O_4$: C, 66.34; H, 4.60. Found: C, 66.53; H, 4.67.

(b) 1SR,3RS,5RS,6SR-Ethyl-2-oxo-3-((3-(3-(trifluoromethyl)phenoxy))benzyl)bicyclo[3.1.0]hexane-6-carboxylate. The title compound was prepared according to the method of Example 1 (c) employing the product of step (a) (5.6 g, 13.5 mmol) and Raney Ni (1.4 g). The crude product was purified by HPLC (10% EtOAc/hexane to 50% EtOAc/hexane) yielding 5.3 g (94%) of the title compound.

(c) 1SR,3SR,5RS,6SR-Ethyl-2-oxo-3-((3-(3-(trifluoromethyl)phenoxy))benzyl)bicyclo[3.1.0]hexane-6-carboxylate. The title compound was prepared according to the method of Example 3 (c) employing the product of step (b) (5.2 g, 12.4 mmol) and Na (0.29 g, 12.4 g-atom). The reaction was concentrated to yield 4.7 g (90%) of the title compound. FDMS: $M^+$=418; Anal. calcd. for $C_{23}H_{21}F_3O_4$.0.1 $CH_2Cl_2$: C, 65.00; H, 5.00. Found: C, 65.06; H, 5.05.

(d) 1SR,2SR,3SR,5RS,6SR-Ethyl-2-aminoacetyl-2-cyano-3-((3-(3-(trifluoromethyl)phenoxy))benzyl)bicyclo[3.1.0]hexane-6-carboxylate and 1SR,2RS,3SR,5RS,6SR-Ethyl-2-aminoacetyl-2-cyano-3-((3-(3-(trifluoromethyl)phenoxy))benzyl)bicyclo[3.1.0]hexane-6-carboxylate. The title compounds were prepared according to the method of Example 2 (c) employing the product of step (c) (4.3 g, 10.3 mmol), KCN (6.7 g, 103 mmol), $NH_4Cl$ (5.5 g, 103 mmol) and $Al_2O_3$ (40 g). The intermediate amino nitrile was acylated using acetyl chloride (1.1 g, 13.4 mmol) and N,N-diisopropylethylamine (1.7 g, 13.4 mmol). The crude product was purified by HPLC yielding 1.9 g (38%) of 1SR,2SR,3SR,5RS,6SR-ethyl-2-aminoacetyl-2-cyano-3-((3-(3-(trifluoromethyl)phenoxy))benzyl)bicyclo[3.1.0]hexane-6-carboxylate (A) and 0.6 g (12%) of the diastereomer, 1SR,2RS,3SR,5RS,6SR-ethyl-2-aminoacetyl-2-cyano-3-((3-(3-(trifluoromethyl)phenoxy))benzyl)bicyclo[3.1.0]hexane-6-carboxylate (B). (A): mp=164–166° C. FDMS: $M^+$=486. Anal. calcd. for $C_{26}H_{25}F_3N_2O_4$: C, 64.19; H, 5.18; N, 5.76; Found: C, 64.28; H, 5.04; N, 5.78. (B): FDMS: $M^+$=486. Anal. calcd. for $C_{26}H_{25}F_3N_2O_4$: C, 64.19; H, 5.18; N, 5.76. Found: C, 64.26; H, 5.30; N, 5.59.

(e) 1SR,2SR,3SR,5RS,6SR-2-Amino-3-((3-(3-(trifluoromethyl)phenoxy))benzyl)bicyclo[3.1.0]hexane-2,6-dicarboxylic acid. The title compound was prepared by the method of Example 3 (e) employing the 2SR product of step (d) (1.4 g, 2.9 mmol). The crude product was dissolved in $H_2O$ at pH 10 and filtered. The product was precipitated at pH 3, filtered and washed with $H_2O$, IPA and EtOAc, yielding 0.75 g (59%) of the title compound. mp=231–232° C. FDMS: $M^+$=435.

EXAMPLE 36

1SR,2SR,3SR,5RS,6SR-2-Amino-3-((3-(4-chloro)phenoxy)benzyl)bicyclo[3.1.0]hexane-2,6-dicarboxylic acid (a) 1SR,5RS,6SR-Ethyl-2-oxo-3-((3-(4-chloro)phenoxy)benzylidenyl)bicyclo[3.1.0]hexane-6-carboxylate. The title compound was prepared according to the method of Example 18 (a) employing the product of Preparation 2 (4.2 g, 25.0 mmol), 3-(4-chlorophenoxy)benzaldehyde (5.8 g, 25.0 mmol) and pyrrolidine (1.0 mL) in EtOH (150 mL). Isolated 8.9 g (93%) of the title compound by filtration. mp=137–138° C. FDMS: $M^+$=382. Anal. calcd. for $C_{22}H_{19}ClO_4$: C, 69.02; H, 5.00. Found: C, 69.12; H, 5.02.

(b) 1SR,3RS,5RS,6SR-Ethyl-2-oxo-3-((3-(4-chloro)phenoxy)benzyl)bicyclo[3.1.0]hexane-6-carboxylate. The title compound was prepared according to the method of Example 1 (c) employing the product of step (a) (8.3 g, 21.7 mmol) and Raney Ni (2.0 g). The crude product was purified by HPLC (10% EtOAc/hexane to 50% EtOAc/hexane) yielding 7.8 g (93%) of the title compound.

(c) 1SR,3SR,5RS,6SR-Ethyl-2-oxo-3-((3-(4-chloro)phenoxy)benzyl)bicyclo[3.1.0]hexane-6-carboxylate. The title compound was prepared according to the method of Example 3 (c) employing the product of step (b) (7.7 g, 20.0 mmol) and Na (0.46 g, 20.0 g-atom). The reaction was concentrated to yield 6.5 g (84%) of the title compound. FDMS: $M^+$=384; Anal. calcd. for $C_{22}H_{21}Cl_1O_4$.0.3 EtOH: C, 68.09; H, 5.76. Found: C, 67.83; H, 5.44.

d) 1SR,2SR,3SR,5RS,6SR-Ethyl-2-aminoacetyl-2-cyano-3-((3-(4-chloro)phenoxy)benzyl)bicyclo[3.1.0]hexane-6-carboxylate and 1SR,2RS,3SR,5RS,6SR-Ethyl-2-aminoacetyl-2-cyano-3-((3-(4-chloro)phenoxy)benzyl)bicyclo[3.1.0]hexane-6-carboxylate. The title compounds were prepared according to the method of Example 2 (c) employing the product of step (c) (6.0 g, 15.6 mmol), KCN (10.1 g, 156 mmol), $NH_4Cl$ (8.3 g, 156 mmol) and $Al_2O_3$ (50 g). The intermediate amino nitrile was acylated using acetyl chloride (2.2 g, 28.0 mmol) and N,N-diisopropylethylamine (3.3 g, 25.5 mmol). The crude products were purified by HPLC (10% EtOAc/hexane to 80% EtOAc/hexane) yielding 2.6 g (37%) of 1SR,2SR,3SR,5RS,6SR-ethyl-2-aminoacetyl-2-cyano-3-((3-(4-chloro)phenoxy)benzyl)bicyclo[3.1.0]hexane-6-carboxylate (A) and 1.0 g (14%) of the diastereomer, 1SR,2RS,3SR,5RS,6SR-ethyl-2-aminoacetyl-2-cyano-3-((3-(4-chloro)phenoxy)benzyl)bicyclo[3.1.0]hexane-6-carboxylate (B). (A): mp=176–178° C. FDMS: $M^+$=452. Anal. calcd. for $C_{25}H_{25}ClN_2O_4$: C, 66.30; H, 5.56; N, 6.19. Found: C, 66.42; H, 5.55; N, 6.10. (B): FDMS: $M^+$=452. Anal. calcd. for $C_{25}H_{25}ClN_2O_4$: C, 66.30; H, 5.56; N, 6.19. Found: C, 66.04; H, 5.74; N, 5.99.

(e) 1SR,2SR,3SR,5RS,6SR-2-Amino-3-((3-(4-chloro)phenoxy)benzyl)bicyclo[3.1.0]hexane-2,6-dicarboxylic acid. The title compound was prepared by the method of Example 3 (e) employing the 2SR product of step (d) (2.4 g, 5.3 mmol). The crude product was dissolved in $H_2O$ at pH 10 and filtered. The product was precipitated at pH 3, filtered and washed with $H_2O$, IPA and EtOAc, yielding 0.97 g (46%) of the title compound. mp=250–253° C. FDMS: $M^+$=401. Anal. calcd. for $C_{21}H_{20}ClNO_5$: C, 62.77; H, 5.02; N, 3.49. Found: C, 62.70; H, 5.13; N, 3.26.

EXAMPLE 37

1SR,2SR,3SR,5RS,6SR-2-Amino-3-((4-(trifluoromethyl)benzyl)bicyclo[3.1.0]hexane-2,6-dicarboxylic acid (a) 1SR,5RS,6SR-Ethyl-2-oxo-3-((4-(trifluoromethyl)benzylidenyl)bicyclo[3.1.0]hexane-6-carboxylate. The title compound was prepared according to the method of Example 18 (a) employing the product of Preparation 2 (4.8 g, 28.5 mmol), 4-(trifluoromethyl)benzaldehyde (5.0 g, 28.7 mmol) and pyrrolidine (1.0 mL) in EtOH (150 mL). Isolated 7.9 g (85%) of the title compound by filtration. mp=131–133° C. FDMS: M$^+$+1=325. Anal. calcd. for $C_{17}H_{15}F_3O_3$.0.2 toluene(from EtOH): C, 64.48; H, 4.88. Found: C, 64.57; H, 4.96.

(b) 1SR,3RS,5RS,6SR-Ethyl-2-oxo-3-((4-(trifluoromethyl)benzyl)bicyclo[3.1.0]hexane-6-carboxylate. The title compound was prepared according to the method of Example 1 (c) employing the product of step (a) (7.7 g, 23.7 mmol) and Raney Ni (1.9 g). The crude product was purified by HPLC (10% EtOAc/hexane to 50% EtOAc/hexane) yielding 6.7 g (87%) of the title compound.

(c) 1SR,3SR,5RS,6SR-Ethyl-2-oxo-3-((4-(trifluoromethyl)benzyl)bicyclo[3.1.0]hexane-6-carboxylate. The title compound was prepared according to the method of Example 3 (c) employing the product of step (b) (6.3 g, 19.3 mmol) and Na (0.44 g, 19.1 g-atom). The reaction was concentrated to yield 6.0 g (95%) of the title compound. FDMS: M$^+$-2=326. Anal. calcd. for $C_{17}H_{17}F_3O_3$: C, 62.57; H, 5.25. Found: C, 62.74; H, 5.11.

d) 1SR,2SR,3SR,5RS,6SR-Ethyl-2-aminoacetyl-2-cyano-3-((4-(trifluoromethyl)benzyl)bicyclo[3.1.0]hexane-6-carboxylate. The title compound was prepared according to the method of Example 2 (c) employing the product of step (c) (5.4 g, 16.4 mmol), KCN (10.7 g, 164 mmol), NH$_4$Cl (8.8 g, 164 mmol) and Al$_2$O$_3$ (50 g). The intermediate amino nitrile was acylated using acetyl chloride (1.9 g, 24.7 mmol) and N,N-diisopropylethylamine (3.2 g, 24.7 mmol). The crude product was purified by crystallization from EtOAc yielding 1.0 g (16%) of 1SR,2SR,3SR,5RS,6SR-ethyl-2-aminoacetyl-2-cyano-3-((4-(trifluoromethyl)benzyl)bicyclo[3.1.0]hexane-6-carboxylate. mp>250° C. FDMS: M$^+$=394. Anal. calcd. for $C_{20}H_{21}F_3N_2O_3$: C, 60.91; H, 5.37; N, 7.10. Found: C, 61.12; H, 5.11; N, 7.10. 10 (e) 1SR,2SR,3SR,5RS,6SR-2-Amino-3-((4-(trifluoromethyl)benzyl)bicyclo[3.1.0]hexane-2,6-dicarboxylic acid. The title compound was prepared by the method of Example 3 (e) employing the product of step (d) (0.73 g, 1.9 mmol). The crude product was dissolved in H$_2$O at pH 10 and filtered. The product was precipitated at pH 3, filtered and washed with H$_2$O, IPA and EtOAc, yielding 0.28 g (43%) of the title compound. mp=247–249° C. FDMS: M$^+$+1=344. Anal. calcd. for $C_{16}H_{16}F_3NO_4$: C, 55.98; H, 4.70; N, 4.08. Found: C, 55.86; H, 4.74; N, 3.85.

EXAMPLE 38

1SR,2SR,3SR,5RS,6SR-2-Amino-3-((2,4-difluoro)benzyl)bicyclo[3.1.0]hexane-2,6-dicarboxylic acid (a) 1SR,5RS,6SR-Ethyl-2-oxo-3-((2,4-difluoro)benzylidenyl)bicyclo[3.1.0]hexane-6-carboxylate. The title compound was prepared according to the method of Example 18 (a) employing the product of Preparation 2 (5.2 g, 31.0 mmol), 2,4-difluorobenzaldehyde (4.4 g, 31.0 mmol) and pyrrolidine (1.0 30 mL) in EtOH (150 mL). Isolated 6.4 g (71%) of the title compound by filtration. mp=151–152° C. FDMS: M$^+$=292. Anal. calcd. for $C_{16}H_{14}F_2O_3$: C, 65.75; H, 4.83. Found: C, 65.50; H, 4.87.

(b) 1SR,3RS,5RS,6SR-Ethyl-2-oxo-3-((2,4-difluoro)benzyl)bicyclo[3.1.0]hexane-6-carboxylate. The title compound was prepared according to the method of Example 1 (c) employing the product of step (a) (6.1 g, 20.8 mmol), Raney Ni (1.5 g) with H$_2$ at 40 psi. The crude product was purified by HPLC (10% EtOAc/hexane to 50% EtOAc/hexane) yielding 5.7 g (93%) of the title compound. FDMS: M$^+$=294. Anal. calcd. for $C_{16}H_{16}F_2O_3$: C, 65.30; H, 5.48. Found: C, 65.73; H, 6.07.

(c) 1SR,3SR,5RS,6SR-Ethyl-2-oxo-3-((2,4-difluoro)benzyl)bicyclo[3.1.0]hexane-6-carboxylate. The title compound was prepared according to the method of Example 3 (c) employing the product of step (b) (5.7 g, 19.4 mmol) and Na (0.44 g, 19.1 g-atom). The reaction was concentrated to yield 4.8 g (84%) of the title compound. FDMS: M$^+$=294; Anal. calcd. for $C_{16}H_{16}F_2O_3$: C, 65.30; H, 5.48. Found: C, 65.43; H, 5.50.

d) 1SR,2SR,3SR,5RS,6SR-Ethyl-2-aminoacetyl-2-cyano-3-((2,4-difluoro)benzyl)bicyclo[3.1.0]hexane-6-carboxylate. The title compound was prepared according to the method of Example 2 (c) employing the product of step (c) (4.5 g, 15.3 mmol), KCN (10.0 g, 153 mmol), NH$_4$Cl (8.2 g, 153 mmol) and Al$_2$O$_3$ (45 g). The intermediate amino nitrile was acylated using acetyl chloride (1.7 g, 21.6 mmol) and N,N-diisopropylethylamine (2.8 g, 21.6 mmol). The crude product was purified by crystallization from EtOAc yielding 1.34 g (24%) of 1SR,2SR,3SR,5RS,6SR-ethyl-2-aminoacetyl-2-cyano-3-((2,4-difluoro)benzyl)bicyclo [3.1.0]hexane-6-carboxylate. mp=259–261° C. FDMS: M$^+$=362. Anal. calcd. for $C_{19}H_{20}F_2N_2O_3$: C, 62.98; H, 5.56; N, 7.73. Found: C, 63.24; H, 5.62; N, 7.71.

(e) 1SR,2SR,3SR,5RS,6SR-2-Amino-3-((2,4-difluoro)benzyl)bicyclo[3.1.0]hexane-2,6-dicarboxylic acid. The title compound was prepared by the method of Example 3 (e) employing the product of step (d) (1.0 g, 2.8 mmol). The crude product was dissolved in H$_2$O at pH 10 and filtered. The product was precipitated at pH 3, filtered and washed with H$_2$O, IPA and EtOAc, yielding 0.56 g (64%) of the title compound. mp=248–250° C. FDMS: M$^+$+1=312. Anal. calcd. for $C_{15}H_{15}F_2NO_4$.0.2 H$_2$O: C, 57.22; H, 4.93; N, 4.45. Found: C, 56.95; H, 4.95; N, 4.44.

EXAMPLE 39

1SR,2SR,3SR,5RS,6SR-2-Amino-3-((2-fluoro)benzyl)bicyclo[3.1.0]hexane-2,6-dicarboxylic acid (a) 1SR,5RS,6SR-2-Oxo-3-((2-fluoro)benzylidenyl)bicyclo[3.1.0]hexane-6-carboxylic acid. The title compound was prepared by the method of Example 9(a) employing the product of Preparation 2 (4.2 g, 25.0 mmol) and 2-fluorobenzaldehyde (3.4 g, 27.5 mmol). The product was isolated by filtering the precipitate obtained after acidification of the aqueous phase, yielding 6.1 g (100%) of the title compound. mp=208–209° C. FDMS: M$^+$=246. Anal. calcd. for $C_{14}H_{11}FO_3$: C, 67.30, H, 4.60. Found: C, 67.39; H, 4.52.

(b) 1SR,5RS,6SR-Ethyl-2-oxo-3-((2-fluoro)benzylidenyl)bicyclo[3.1.0]hexane-6-carboxylate. The title compound was prepared according to the method of Example 10 (b) employing the product of step (a) (5.4 g, 21.9 mmol), Et$_3$N (2.4 g, 24.1 mmol) and DMAP (0.3 g, 2.5 mmol) and ethyl chloroformate (2.6 g, 24.1 mmol) to give 5.4 g (90%) of the title compound. FDMS: M$^+$=274. Anal. calcd. for $C_{16}H_{15}FO_3$: C, 70.06, H, 5.51. Found: C, 69.80; H, 5.44.

(b) 1SR,3RS,5RS,6SR-Ethyl-2-oxo-3-((2-fluoro)benzyl) bicyclo[3.1.0]hexane-6-carboxylate. The title compound was prepared according to the method of Example 1 (c) employing the product of step (a) (5.1 g, 18.6 mmol), Raney Ni (1.3 g) with hydrogen at 40 psi. The crude product was purified by HPLC (10% EtOAc/hexane to 50% EtOAc/hexane) yielding 3.3 g (64%) of the title compound. FDMS: M$^+$+1=277. Anal. calcd. for $C_{16}H_{17}FO_3 \cdot 0.1$ hexane: C, 69.98; H, 6.51. Found: C, 70.13; H, 6.11.

(c) 1SR,3SR,5RS,6SR-Ethyl-2-oxo-3-((2-fluoro)benzyl) bicyclo[3.1.0]hexane-6-carboxylate. The title compound was prepared according to the method of Example 3 (c) employing the product of step (b) (3.0g, 10.9 mmol) and Na (0.25 g, 10.9 g-atom). The reaction was concentrated to yield 2.7 g (86%) of the title compound. mp=66–69° C. FDMS: M$^+$=276. Anal. calcd. for $C_{16}H_{17}F_1O_3$: C, 69.55; H, 6.20. Found: C, 69.63; H, 6.17.

d) 1SR,2SR,3SR,5RS,6SR-Ethyl-2-aminoacetyl-2-cyano-3-((2-fluoro)benzyl)bicyclo[3.1.0]hexane-6-carboxylate. The title compound was prepared according to the method of Example 2 (c) employing the product of step (c) (2.5 g, 9.1 mmol), KCN (5.9 g, 91 mmol), NH$_4$Cl (4.8 g, 91 mmol) and Al$_2$O$_3$ (30 g). The intermediate amino nitrile was acylated using acetyl chloride (1.05 g, 13.4 mmol) and N,N-diisopropylethylamine (1.7 g, 13.4 mmol). The crude product was purified by crystallization from EtOAc yielding 0.7 g (22%) of 1SR,2SR,3SR,5RS,6SR-ethyl-2-aminoacetyl-2-cyano-3-((2-fluoro)benzyl)bicyclo[3.1.0] hexane-6-carboxylate. FDMS: M$^+$=344. Anal. calcd. for $C_{19}H_{21}FN_2O_3$: C, 66.27; H, 6.15; N, 8.13. Found: C, 66.52; H, 6.15; N, 8.29.

(e) 1SR,2SR,3SR,5RS,6SR-2-Amino-3-((2-fluoro) benzyl)bicyclo[3.1.0]hexane-2,6-dicarboxylic acid. The title compound was prepared by the method of Example 3 (e) employing the product of step (d) (0.35 g, 1.0 mmol). The crude product was dissolved in H$_2$O at pH 10 and filtered. The product was precipitated at pH 3, filtered and washed with H$_2$O, IPA and EtOAc, yielding 0.24 g (81%) of the title compound. mp=250–252° C. FDMS: M$^+$+1=294. Anal. calcd. for $C_{15}H_{16}F_1NO_4 \cdot 0.2$ H$_2$O: C, 60.32; H, 5.60; N, 4.69. Found: C, 60.14; H, 5.35; N, 4.36.

EXAMPLE 40

1SR,2SR,3SR,5RS,6SR-2-Amino-3-((2,3-dichloro) benzyl)bicyclo[3.1.0]hexane-2,6-dicarboxylic acid (a) 1SR,5RS,6SR-Ethyl-2-oxo-3-((2,3-dichloro) benzylidenyl)bicyclo[3.1.0]hexane-6-carboxylate. The title compound was prepared according to the method of Example 18 (a) employing the product of Preparation 2 (6.0 g, 35.7 mmol), 2,3-dichlorobenzaldehyde (6.2 g, 35.4 mmol) and pyrrolidine (1.0 mL) in EtOH (150 mL). Isolated 8.3 g (71%) of the title compound by filtration. mp=136–138° C. FDMS: M$^+$=325. Anal. calcd. for $C_{16}H_{14}Cl_2O_3$: C, 59.10; H, 4.34. Found: C, 59.35; H, 4.39.

(b) 1SR,3RS,5RS,6SR-Ethyl-2-oxo-3-((2,3-dichloro) benzyl)bicyclo[3.1.0]hexane-6-carboxylate. The title compound was prepared according to the method of Example 1 (c) employing the product of step (a) (7.2 g, 22.1 mmol), Raney Ni (2.0 g) with hydogen at 40 psi. The crude product was purified by HPLC (10% EtOAc/hexane to 50% EtOAc/hexane) yielding 2.6 g (35%) of the title compound. mp=79–81° C. FDMS: M$^+$=327. Anal. calcd. for $C_{16}H_{16}Cl_2O_3$: C, 58.73; H, 4.93. Found: C, 58.94; H, 4.78.

(c) 1SR,3SR,5RS,6SR-Ethyl-2-oxo-3-((2,3-dichloro) benzyl)bicyclo[3.1.0]hexane-6-carboxylate. The title compound was prepared according to the method of Example 3 (c) employing the product of step (b) (2.6 g, 7.9 mmol) and Na (0.18 g, 7.8 g-atom). The reaction was concentrated to yield 2.4 g (92%) of the title compound.

d) 1SR,2SR,3SR,5RS,6SR-Ethyl-2-aminoacetyl-2-cyano-3-((2,3-dichloro)benzyl)bicyclo[3.1.0]hexane-6-carboxylate. The title compound was prepared according to the method of Example 2 (c) employing the product of step (c) (2.4 g, 7.3 mmol), KCN (4.8 g, 73 mmol), NH$_4$Cl (3.9 g, 73 mmol) and Al$_2$O$_3$ (25 g). The intermediate amino nitrile was acylated using acetyl chloride (0.6 g, 7.6 mmol) and N,N-diisopropylethylamine (1.0 g, 7.6 mmol). The crude product was purified by crystallization from EtOAc yielding 0.73 g (25%) of 1SR,2SR,3SR,5RS,6SR-ethyl-2-aminoacetyl-2-cyano-3-((2,3-dichloro)benzyl)bicyclo [3.1.0]hexane-6-carboxylate. FDMS: M$^+$=395. Anal. calcd. for $C_{19}H_{20}Cl_2N_2O_3$: C, 57.73; H, 5.10; N, 7.09. Found: C, 57.48; H, 5.15; N, 6.91.

(e) 1SR,2SR,3SR,5RS,6SR-2-Amino-3-((2,3-dichloro) benzyl)bicyclo[3.1.0]hexane-2,6-dicarboxylic acid. The title compound was prepared by the method of Example 3 (e) employing the product of step (d) (0.65 g, 1.6 mmol). The crude product was dissolved in H$_2$O at pH 10 and filtered. The product was precipitated at pH 3, filtered and washed with H$_2$O, IPA and EtOAc, yielding 0.42 g (93%) of the title compound. mp=259–260° C. Anal. calcd. for $C_{15}H_{15}Cl_2NO_4$: C, 52.34; H, 4.39; N, 4.07. Found: C, 52.13; H, 4.30; N, 3.77.

EXAMPLE 41

1SR,2SR,3SR,5RS,6SR-2-Amino-3-((2,3-difluoro) benzyl)bicyclo[3.1.0]hexane-2,6-dicarboxylic acid The title compound was prepared by the method of Example 40 originating from the starting material, 1SR,5RS, 6SR Ethyl-2-oxabicyclo[3.1.0]hexane-6-carboxylate. The intermediate, 1SR,2SR,3SR,5RS,6SR-ethyl-2-aminoacetyl-2-cyano-3-((2,3-difluoro)benzyl)bicyclo[3.1.0]hexane-6-carboxylate (0.2 g, 0.6 mmol) was hydrolyzed employing method of Example 3(e). The crude product was dissolved in H$_2$O at pH 10 and filtered. The product was precipitated at pH 3, filtered and washed with H$_2$O, IPA and EtOAc, yielding 0.12 g (75%) of the title compound. mp>250° C. FDMS: M$^+$+1=312. Anal. calcd. for $C_{16}H_{19}NO_4 \cdot 0.1$ NaCl: C, 56.81; H, 4.77; N, 4.29. Found: C, 56.56; H, 4.90; N, 4.29.

EXAMPLE 42

1S,2S,3S,5R,6S-2-Amino-3-((3-chloro-4-fluoro) benzyl)bicyclo[3.1.0]hexane-2,6-dicarboxylic acid (a) 1S,5R,6S-2-Oxo-3-((3-chloro-4-fluoro)benzylidenyl) bicyclo[3.1.0]hexane-6-carboxylic acid. The title compound was prepared by the method of Example 9(a) employing 1S,5R,6S-(+)-2-oxobicyclo[3.1.0]hexane-6-carboxylic acid (preparation described in Example 19 of European Patent Application Publication No. 696577A1) (7.0 g, 50 mmol) and 3-chloro-4-fluorobenzaldehyde (9.0 g, 56 mmol). The product was isolated by filtering the precipitate obtained after acidification of the aqueous phase, yielding 14.0 g (99%) of the title compound. mp=171–172° C. FDMS: M$^+$=280; Optical rotation: $\alpha_D$=209.49° (c=0.01, MeOH). Anal. calcd. for $C_{14}H_{10}ClFO_3$: C, 59.91; H, 3.59. Found: C, 59.88; H, 3.79.

(b) 1S,5R,6S-Ethyl-2-oxo-3-((3-chloro-4-fluoro) benzylidenyl)bicyclo[3.1.0]hexane-6-carboxylate. The title compound was prepared by the method of Example 10 (b) employing the product of step (a) (12.4 g, 44.2 mmol) and DMAP (0.5 g, 4.1 mmol), $Et_3N$ (4.9 g, 48.6 mmol) and ethyl chloroformate (4.8 g, 44.2 mmol). The crude product (10.8 g) was purified by recrystallization (EtOAc/hexane) yielding 7.3 g (53%) of the title compound. FDMS: $M^+$=308. Optical rotation: $\alpha_D$=82.77° (c=0.01, $CH_2Cl_2$); Anal. calcd. for $C_{16}H_{14}ClFO_3$: C, 62.25; H, 4.57. Found: C, 62.54; H, 4.65.

(c) 1S,3S,5R,6S-Ethyl-2-oxo-3-((3-chloro-4-fluoro) benzyl)bicyclo[3.1.0]hexane-6-carboxylate and 1S,3R,5R, 6S-Ethyl-2-oxo-3-((3-chloro-4-fluoro)benzyl)bicyclo[3.1.0] hexane-6-carboxylate. The title compounds were prepared according to the method of Example 1 (c) employing the product of step (b) (8.5 g, 27.5 mmol), Raney Ni (2.2 g) with hydogen at 40 psi. The crude products were purified by HPLC (10% EtOAc/hexane to 50% EtOAc/hexane) yielding 4.2 g (49%) of the 1S,3S,5R,6S-Ethyl-2-oxo-3-((3-chloro-4-fluoro)benzyl)bicyclo[3.1.0]hexane-6-carboxylate and 4.0 g (47%) of a mixture of the over reduced carbinol products. The carbinol products were oxidized using pyridinium chlorochromate and powdered sieves, yielding 2.9 g of 1S,3S, 5R,6S-Ethyl-2-oxo-3-((3-chloro-4-fluoro)benzyl)bicyclo [3.1.0]hexane-6-carboxylate and 1S,3R,5R,6S-Ethyl-2-oxo-3-((3-chloro-4-fluoro)benzyl)bicyclo[3.1.0]hexane-6-carboxylate products. The combined isolated yield for the title compounds is 7.1 g (83%). FDMS: $M^+$=312. Optical rotation: $\alpha_D$=82.77° (c=0.01, $CH_2Cl_2$); Anal. calcd. for $C_{16}H_{14}ClFO_3 \cdot 0.1\ CH_2CL_2$: C, 60.86; H, 5.77. Found: C, 60.74; H, 6.01.

(d) 1S,3S,5R,6R-Ethyl-2-oxo-3-((3-chloro-4-fluoro) benzyl)bicyclo[3.1.0]hexane-6-carboxylate. The title compound was prepared according to the method of Example 3 (c) employing the product of step (c) (6.7 g, 21.5 mmol) and Na (0.52 g, 22.6 g-atom). Isolated 6.0 g (89%) of the title compound. Optical rotation: $\alpha_D$=7.70° (c=0.01, $CH_2Cl_2$); Anal. calcd. for $C_{16}H_{16}ClFO_3$: C, 61.84; H, 5.19. Found: C, 61.75; H, 5.26.

e) 1S,2S,3S,5R,6S-Ethyl-2-aminoacetyl-2-cyano-3-((3-chloro-4-fluoro)benzyl)bicyclo[3.1.0]hexane-6-carboxylate and 1S,2R,3S,5R,6S-ethyl-2-aminoacetyl-2-cyano-3-((3-chloro-4-fluoro)benzyl)bicyclo[3.1.0]hexane-6-carboxylate. The title compounds were prepared according to the method of Example 2 (c) employing the product of step (d) (6.0 g, 19.3 mmol), KCN (12.6 g, 193 mmol), $NH_4Cl$ (10.4 g, 193 mmol) and $Al_2O_3$ (60 g). The intermediate amino nitrile was acylated using acetyl chloride (1.7 g, 21.7 mmol) and N,N-diisopropylethylamine (2.8 g, 21.7 mmol). The diastereomer 1S,2S,3s,5R,6S-ethyl-2-aminoacetyl-2-cyano-3-((3-chloro-4-fluoro)benzyl)bicyclo[3.1.0]hexane-6-carboxylate (A) was purified by crystallization from EtOAc yielding 2.4 g (32%). The diastereomer, 1S,2R,3S,5R,6S-ethyl-2-aminoacetyl-2-cyano-3-((3-chloro-4-fluoro)benzyl)bicyclo [3.1.0]hexane-6-carboxylate (B) was isolated by HPLC (20% EtOAc/hexane to 80% EtOAc/hexane) yielding 1.4 g (19%). (A): FDMS: $M^+$=378. Optical rotation: $\alpha_D$=27.03° (c=0.01, $CH_2Cl_2$) . Anal. calcd. for $C_{19}H_{20}ClFN_2O_3$: C, 60.24; H, 5.32; N, 7.40. Found: C, 60.04; H, 5.45; N, 7.22. (B): FDMS: $M^+$=378. Optical rotation: $\alpha_D$=33.31° (c=0.01, $CH_2Cl_2$). Anal. calcd. for $C_{19}H_{20}ClFN_2O_3$: C, 60.24; H, 5.32; N, 7.40. Found: C, 60.09; H, 5.19; N, 7.30.

(f) 1S,2S,3S,5R,6S-2-Amino-3-((3-chloro-4-fluoro) benzyl)bicyclo[3.1.0]hexane-2,6-dicarboxylic acid. The title compound was prepared by the method of Example 3 (e) employing the product (A) of step (e) (1.9 g, 5.0 mmol). The crude product was dissolved in $H_2O$ at pH 10 and filtered. The product was precipitated at pH 3, filtered and washed with $H_2O$, IPA and EtOAc, yielding 1.4 g (85%) of the title compound. mp=253° C. FDMS: $M^+$-45($CO2H$)=282. Anal. calcd. for $C_{15}H_{15}FClNO_4 \cdot 0.11$ NaCl: C, 53.91; H, 4.52; N, 4.19. Found: C, 54.24; H, 4.64; N, 3.79.

EXAMPLE 43

1S,2S,3S,5R,6S-2-Amino-3-((3-methyl)benzyl) bicyclo[3.1.0]hexane-2,6-dicarboxylic acid (a) The title compound was prepared by the method of Example 42 originating from the chiral starting material, 1S,5R,6S-2-oxobicyclo[3.1.0]-hexane-6-carboxylic acid. The intermediate, 1S,2S,3S,5R,6S-ethyl-2-aminoacetyl-2-cyano-3-((3-methyl)benzyl)bicyclo-[3.1.0]hexane-6-carboxylate (1.4 g, 4.1 mmol) was hydrolyzed employing method of Example 3(e). The crude product was dissolved in $H_2O$ at pH 10 and filtered. The product was precipitated at pH 3, filtered and washed with $H_2O$, Acetone and EtOAc, yielding 1.11 g (94%) of the title compound. mp=244–245° C. FDMS: $M^+$-45($CO2H$)=244. Anal. calcd. for $C_{16}H_{19}NO_4 \cdot 0.25$ NaCl: C, 63.22; H, 6.30; N, 4.61. Found: C, 63.53; H, 6.36; N, 4.56.

EXAMPLE 44

1S,2S,3S,5R,6S-2-Amino-3-((4-fluoro-3-methyl) benzyl)bicyclo[3.1.0]hexane-2,6-dicarboxylic acid The title compound prepared was by the method of Example 42 originating from the chiral starting material, 1S,5R,6S-2-oxabicyclo-[3.1.0]hexane-6-carboxylic acid. The intermediate, 1S,2S,3S,5R,6S-ethyl-2-aminoacetyl-2-cyano-3-((4-fluoro-3-methyl)benzyl)bicyclo[3.1.0]hexane-6-carboxylate (0.85 g, 2.4 mmol) was hydrolyzed employing method of Example 3 (e). The crude product was dissolved in $H_2O$ at pH 10 and filtered. The product was precipitated at pH 3, filtered and washed with $H_2O$, Acetone and EtOAc, yielding 0.73 g (99%) of the title compound. mp=246–247° C. FDMS: $M^+$-35(F,$NH_2$)=272. Anal. calcd. for $C_{16}H_{18}FNO_4 \cdot 0.25$ NaCl: C, 59.69; H, 5.64; N, 4.35. Found: C, 59.70; H, 5.81; N, 4.45.

We claim:

1. A compound of the formula

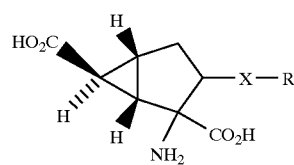

I in which X represents a bond, S, O or $NR^a$; and R represents a (1–6C) alkyl group; a (2–6C)alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C)alkenyl or (2–6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_n R^b$; n is 0 or 1; and $R^b$ is as defined for R; or a non-toxic metabolically labile ester or amide thereof; or a pharmaceutically acceptable salt thereof.

2. A compound as claimed in claim 1, in which R represents a (1–4C) alkyl group, a (2–4C) alkenyl group, a (2–4C) alkynyl group or a phenyl (1–4C) alkyl group which is unsubstituted or substituted on phenyl by one, two or three substituents selected independently from halogen, (1–4C) alkyl, (1–4C) alkoxy, (1–4C)fluoroalkyl, (1–4C) fluoroalkoxy, phenyl and phenoxy.

3. A compound as claimed in claim 2, in which R represents a phenyl (1–4C)alkyl group in which the phenyl ring is unsubstituted or substituted by one, two or three substituents selected independently from fluoro, chloro, methyl, isopropyl, methoxy, trifluoromethyl, trifluoromethoxy, phenyl and phenoxy.

4. A compound as claimed in claim 1, in which R represents a phenyl(1–4C)alkyl or diphenyl(1–4C)alkyl group in which any phenyl ring is unsubstituted or substituted by one, two or three substituents selected independently from fluoro, chloro, methyl, isopropyl, methoxy, trifluoromethyl, trifluoromethoxy, tetrafluoroethoxy, phenyl, phenoxy, 3-trifluoromethylphenoxy, and 4-chlorophenoxy.

5. A compound as claimed in claim 4, in which R represents a benzyl or diphenylmethyl group in which any phenyl ring is unsubstituted or substituted as defined in claim 4.

6. A compound as claimed in claim 1, in which R is methyl, phenylpropyl, benzyl, 2-fluorobenzyl, 3-fluorobenzyl, 4-fluorobenzyl, 2,3-difluorobenzyl, 2,4-difluorobenzyl, 2,5-difluorobenzyl, 3,5-difluorobenzyl, 3,4-difluorobenzyl, 2,3,4-trifluorobenzyl, 2-chlorobenzyl, 3-dichlorobenzyl, 4-chlorobenzyl, 2,3-dichlorobenzyl, 2-chloro-5-trifluoromethylbenzyl, 3-chloro-4-fluorobenzyl, 2-methylbenzyl, 3-methylbenzyl, 4-methylbenzyl, 4-fluoro-3-methylbenzyl, 3-fluoro-2-methylbenzyl, 3,5-dimethylbenzyl, 4-isopropylbenzyl, 2,4-dimethylbenzyl, 2,5-dimethylbenzyl, 2-methoxybenzyl, 3-methoxybenzyl, 4-methoxybenzyl, 3-fluoro-4-methoxybenzyl, 3-methyl-4-methoxybenzyl, 4-trifluoromethylbenzyl, 3-fluoro-5-trifluoromethylbenzyl, 3-trifluoromethoxybenzyl, 3-tetrafluoroethoxybenzyl, 4-phenylbenzyl, 3-phenoxybenzyl, 3-(3-trifluoromethylphenoxy)benzyl, 3-(4-chlorophenoxy)benzyl, or diphenylmethyl.

7. A compound as claimed in claim 1, in which X represents a bond.

8. A compound as claimed in claim 1, which has the stereochemistry shown below.

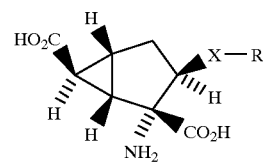

9. A compound of formula

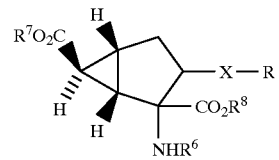

IV in which X represents a bond, S, O or $NR^a$; and R represents a (1–6C) alkyl group; a (2–6C)alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups: or a (1–6C) alkyl, (2–6C)alkenyl or (2–6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups: $R^a$ represents hydrogen or a group of formula $(CO)_n R^b$; n is 0 or 1; and $R^b$ is as defined for R; $R^6$ represents a hydrogen atom or a nitrogen protecting group and each of $R^7$ and $R^8$ independently represent a hydrogen atom or a carboxyl protecting group, or a salt thereof.

10. A pharmaceutical formulation, which comprises a compound as claimed in claim 1 and a pharmaceutically acceptable carrier, diluent or excipient.

11. A method of modulating one or more of the functions of metabotropic glutamate receptors in a warm blooded mammal requiring such treatment, which comprises administering an effective amount of a compound as claimed in claim 1.

12. A method of treating psychosis in a warm blooded mammal requiring such treatment, which comprises administering an effective amount of a compound as claimed in claim 1.

13. A method of treating anxiety in a warm blooded mammal requiring such treatment, which comprises administering an effective amount of a compound as claimed in claim 1.

* * * * *